United States Patent
Morozov et al.

(10) Patent No.: US 11,453,717 B2
(45) Date of Patent: Sep. 27, 2022

(54) TRISPECIFIC ANTIBODIES AGAINST IL-17A, IL-17F AND OTHER PRO-INFLAMMATORY MOLECULE

(71) Applicant: JOINT STOCK COMPANY "BIOCAD", St.Petersburg (RU)

(72) Inventors: Dmitry Valentinovich Morozov, Moscow (RU); Andrei Borisovich Ulitin, Puschino (RU); Ekaterina Sergeevna Zubareva, Kirov (RU); Iakov Iurevich Ustiugov, Berezniki (RU); Aleksandr Vladimirovich Karabelskii, Gatchina (RU); Dmitry Valeryevich Korzhavin, St.Petersburg (RU); Tatiana Veniaminovna Chernovskaya, Lyubuchany (RU); Aleksandr Valerevich Grachev, St.Petersburg (RU); Yury Ivanovich Basovskiy, Moscow (RU); Ekaterina Aleksandrovna Lomkova, St.Petersburg (RU); Veronika Sergeevna Usatova, Borovichi (RU); Aleksei Aleksandrovich Aleksandrov, Perm (RU); Elena Leonidovna Morozova, Moscow (RU); Roman Alekseevich Ivanov, Moscow (RU); Pavel Andreevich Iakovlev, St.Petersburg (RU)

( * ) Notice: Subject to any disclaimer, the term of this patent is extended or adjusted under 35 U.S.C. 154(b) by 332 days.

(21) Appl. No.: 16/097,562

(22) PCT Filed: Dec. 2, 2016

(86) PCT No.: PCT/RU2016/050073
§ 371 (c)(1),
(2) Date: Oct. 29, 2018

(87) PCT Pub. No.: WO2017/188850
PCT Pub. Date: Nov. 2, 2017

(65) Prior Publication Data
US 2021/0332120 A1   Oct. 28, 2021

(30) Foreign Application Priority Data

Apr. 29, 2016  (RU) .......................... RU2016117140

(51) Int. Cl.
*C07K 16/24* (2006.01)
*A61K 39/395* (2006.01)
*A61P 19/02* (2006.01)
*A61K 45/06* (2006.01)
*A61K 39/00* (2006.01)

(52) U.S. Cl.
CPC ........ *C07K 16/244* (2013.01); *A61K 39/3955* (2013.01); *A61K 45/06* (2013.01); *A61P 19/02* (2018.01); *C07K 16/241* (2013.01); *A61K 2039/505* (2013.01); *C07K 2317/22* (2013.01); *C07K 2317/24* (2013.01); *C07K 2317/31* (2013.01); *C07K 2317/55* (2013.01); *C07K 2317/565* (2013.01); *C07K 2317/569* (2013.01); *C07K 2317/732* (2013.01); *C07K 2317/734* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,634,665 A | 1/1987 | Axel et al. |
| 4,740,461 A | 4/1988 | Kaufman |
| 4,912,040 A | 3/1990 | Kaufman et al. |
| 4,959,455 A | 9/1990 | Clark et al. |
| 4,968,615 A | 11/1990 | Koszinowski et al. |
| 5,168,062 A | 12/1992 | Stinski |
| 5,179,017 A | 1/1993 | Axel et al. |
| 6,517,529 B1 | 2/2003 | Quinn |
| 8,496,936 B2 | 7/2013 | Lewis et al. |
| 2002/0151682 A1 | 10/2002 | Athwal et al. |
| 2002/0177188 A1 | 11/2002 | Chen et al. |
| 2003/0166862 A1 | 9/2003 | Golstein et al. |
| 2005/0244874 A1 | 11/2005 | Kastelein et al. |

(Continued)

FOREIGN PATENT DOCUMENTS

| | | |
|---|---|---|
| EP | 3181147 A1 | 6/2017 |
| EP | 3199550 A1 | 8/2017 |

(Continued)

OTHER PUBLICATIONS

Schroeder et al. (J Allergy Clin Immunol 2010, 125:S41-S52 (Year: 2010).*
Lloyd et al. (Protein Engineering, Design & Selection 2009, 22:159-168) (Year: 2009).*
Rudikoff et al. (Proc Natl Acad Sci USA 1982 vol. 79 p. 1979) (Year: 1979).*

(Continued)

*Primary Examiner* — Sharon X Wen
(74) *Attorney, Agent, or Firm* — Anglehart et al.

(57) ABSTRACT

The present invention relates to the field of biotechnology and provides monoclonal tri-specific binding molecules that specifically bind to human IL-17A, human IL-17F, and a human pro-inflammatory molecule (in particular, TNFα) with high affinity. The invention also relates to DNA constructs encoding said binding molecules, related expression vectors and methods of production, and methods of treatment using said binding molecules.

23 Claims, 23 Drawing Sheets
Specification includes a Sequence Listing.

(56) References Cited

U.S. PATENT DOCUMENTS

| | | |
|---|---|---|
| 2007/0269428 A1 | 11/2007 | Christie et al. |
| 2009/0004199 A1 | 1/2009 | Jaspers et al. |
| 2009/0280131 A1 | 11/2009 | Di Padova et al. |
| 2010/0266531 A1 | 10/2010 | Hsieh et al. |
| 2012/0183558 A1 | 7/2012 | Adams et al. |
| 2014/0255406 A1 | 9/2014 | Allan et al. |
| 2016/0326241 A1 | 11/2016 | Auer et al. |

FOREIGN PATENT DOCUMENTS

| | | |
|---|---|---|
| WO | 00/09560 A2 | 2/2000 |
| WO | WO 2005/051422 A1 | 6/2005 |
| WO | WO 2005/108616 A1 | 11/2005 |
| WO | WO 2006/013107 A1 | 2/2006 |
| WO | 2009/136286 A2 | 11/2009 |
| WO | WO 2010/102251 A2 | 9/2010 |
| WO | WO 2012/095662 A1 | 7/2012 |
| WO | 2012/156219 A1 | 11/2012 |
| WO | 2013/063110 A1 | 5/2013 |
| WO | WO 2014/137961 A1 | 9/2014 |
| WO | WO 2015/014979 A1 | 2/2015 |
| WO | 2016/048188 A1 | 3/2016 |
| WO | 2017/102830 A1 | 6/2017 |

OTHER PUBLICATIONS

MacCallum et al. (J. Mol. Biol. 1996 262, 732-745) (Year: 1996).*
Pascalis et al. (The Journal of Immunology (2002) 169, 3076-3084) (Year: 2002).*
Casset et al. (BBRC 2003, 307:198-205) (Year: 2003).*
Vajdos et al. (J. Mol. Biol. (2002) 320, 415-428) (Year: 2002).*
Chen et al. (J. Mol. Bio. (1999) 293, 865-881) (Year: 1999).*
Wu et al. (J. Mol. Biol. (1999) 294, 151-162) (Year: 1999).*
Padlan et al. (PNAS 1989, 86:5938-5942) (Year: 1989).*
Lamminmaki et al. (JBC 2001, 276:36687-36694) (Year: 2001).*
Piche-Nicholas et al. MABS 2018, 10:81-94 (Year: 2018).*
Piche-Nicholas et al. MABS 2018, 10:81-94.*
Aggarwal et al., IL-17: prototype member of an emerging cytokine family, J Leukoc Biol. Jan. 2002;71(1):1-8.
Aggarwal et al., Interleukin-23 promotes a distinct CD4 T cell activation state characterized by the production of interleukin-17, J Biol Chem. Jan. 17, 2003;278(3):1910-4. Epub Nov. 3, 2002.
Chabaud et al., Enhancing effect of IL-1, IL-17, and TNF-alpha on macrophage inflammatory protein-3alpha production in rheumatoid arthritis: regulation by soluble receptors and Th2 cytokines, J Immunol. Nov. 15, 2001;167(10):6015-20.
Davidson et al., Autoimmune diseases, N Engl J Med. Aug. 2, 2001;345(5):340-50.
Hymowitz et al., IL-17s adopt a cystine knot fold: structure and activity of a novel cytokine, IL-17F, and implications for receptor binding, Embo J. Oct. 1, 2001;20(19):5332-41.
LeGrand et al., Interleukin-1, tumor necrosis factor α, and interleukin-17 synergistically up-regulate nitric oxide and prostaglandin E2 production in explants of human osteoarthritic knee menisci, Arthritis Rheum. Sep. 2001;44(9):2078-83.
PCT/RU2016/050073 ISR.
PCT/RU2016/050073 written opinion translated.
R L van Bezooijen et al., Interleukin 17 synergises with tumour necrosis factor alpha to induce cartilage destruction in vitro. Ann Rheum Dis. Oct. 2002: 61(10): 870-876.
Starnes et al., Cutting edge: IL-17F, a novel cytokine selectively expressed in activated T cells and monocytes, regulates angiogenesis and endothelial cell cytokine production, J Immunol. Oct. 15, 2001;167(8):4137-40.
von Andrian et al,, T-cell function and migration. Two sides of the same coin. N Engl J Med. Oct. 5, 2000;343(14):1020-34.
Wim B van den Berg, Anti-cytokine therapy in chronic destructive arthritis, Arthritis Res. 2001: 3(1): 18-26.
Wright JF et al., The human IL-17F/IL-17A heterodimeric cytokine signals through the IL-17RA/IL-17RC receptor complex, J Immunol. Aug. 15, 2008;181(4):2799-805.

Corresponding European patent application No. 16900649.1 extended search report dated Apr. 12, 2019.
Jens A. A. Fischer et al., Combined Inhibition of Tumor Necrosis Factor α and Interleukin-17 As a Therapeutic Opportunity in Rheumatoid Arthritis: Development and Characterization of a Novel Bispecific Antibody. Arthritis & Rheumatology. vol. 67, Issue 1. Jan. 2015. pp. 51-62.
Michela Silacci et al., Discovery and characterization of COVA322, a clinical-stage bispecific TNF/IL-17A inhibitor for the treatment of inflammatory diseases. mAbs, vol. 8, 2016—Issue 1, pp. 141-149 | Received Jul. 1, 2015, Accepted Sep. 4, 2015, Accepted author version posted online: Sep. 22, 2015, Published online: Oct. 13, 2015.
Roland E. Kontermann et al., Bispecific antibodies. Drug Discovery Today. vol. 20, Issue 7, Jul. 2015, pp. 838-847.
Hilary S. Bartlett et al., Targeting the IL-17-TH17 pathway. Nature Reviews. Drug Discovery, vol. 14, No. 1, Dec. 31, 2014 (Dec. 31, 2014), pp. 11-12.
Almagro et al., Humanization of antibodies. Front Biosci. 13:1619-1633 (2008).
Magdelaine-Beuzelin et al., Structure-function relationships of the variable domains of monoclonal antibodies approved for cancer treatment. Critical Reviews in Oncology/Hematology. vol. 64, Issue 3, Dec. 2007, pp. 210-225.
Burks et al., In vitro scanning saturation mutagenesis of an antibody binding pocket, roc Natl Acad Sci USA, 94:412-417 (1997).
Kipriyanov et al., Recombinant single-chain Fv fragments carrying C-terminal cysteine residues: Production of bivalent and biotinylated miniantibodies. Molecular Immunology. vol. 31, Issue 14, Oct. 1994, pp. 1047-1058.
Ill et al., Design and construction of a hybrid immunoglobulin domain with properties of both heavy and light chain variable regions. Protein Engineering, Design and Selection, vol. 10, Issue 8, Aug. 1997, pp. 949-957.
Martin et al., The affinity-selection of a minibody polypeptide inhibitor of human interleukin-6.. Embo J. 13:5303-5309 (1994).
Ahmad et al., scFv Antibody: Principles and Clinical Application. Clinical and Developmental Immunology 2012, Article ID 980250 (2012).
Pearson, Empirical statistical estimates for sequence similarity searches. Journal of Molecular Biology. vol. 276, Issue 1, Feb. 13, 1998, pp. 71-84.
De Genst et al., Antibody repertoire development in camelids. Developmental & Comparative Immunology. vol. 30, Issues 1-2, 2006, pp. 187-198.
Bond et al., Contributions of CDR3 to VHH Domain Stability and the Design of Monobody Scaffolds for Naive Antibody Libraries. Journal of Molecular Biology. vol. 332, Issue 3, Sep. 19, 2003, pp. 643-655.
Woodie et al., Phase I Trial of a Humanized, Fc Receptor Nonbinding OKT3 Antibody, huOKT3γ1 (Ala-Ala) In the Treatment of Acute Renal Allograft Rejection. Transplantation 68(5):608-616 (1999).
Bird et al., Single-chain antigen-binding proteins. Science 242:423 426 (1988).
Lefranc et al., IMGT unique numbering for immunoglobulin and T cell receptor variable domains and Ig superfamily V-like domains Developmental & Comparative Immunology. vol. 27, Issue 1, Jan. 2003, pp. 55-77.
Huston et al., Protein engineering of antibody binding sites: recovery of specific activity in an anti-digoxin single-chain Fv analogue produced in *Escherichia coli*. Proc. Natl. Acad. Sci. USA 85:5879 5883 (1988).
Holliger et al., "Diabodies": small bivalent and bispecific antibody fragments. Proc. Natl. Acad. Sci. USA 90:6444-6448 (1993).
Kipriyanov et al., Single-chain antibody streptavidin fusions: Tetrameric bifunctional scFv-complexes with biotin binding activity and enhanced affinity to antigen. Human Antibodies and Hybridomas 6:93-101 (1995).
Wu et al., Stepwise in vitro affinity maturation of Vitaxin, an αvβ3-specific humanized mAb. Proc Natl Acad Sci USA 95:6037-6042 (1998).

(56) References Cited

OTHER PUBLICATIONS

HJ de Haard et al., A large non-immunized human Fab fragment phage library that permits rapid isolation and kinetic analysis of high affinity antibodies. J Biol Chem 274(26):18218-18230 (1999).
Pearson, [5] Rapid and sensitive sequence comparison with FASTP and FASTA. Methods Enzymol. 183:63-98 (1990).
Pearson, Flexible Sequence Similarity Searching with the FASTA3 Program Package. Methods Mol. Biol. 132:185-219 (2000).
Traunecker et al., Bispecific single chain molecules (Janusins) target cytotoxic lymphocytes on HIV infected cells. EMBO J. 10:3655-3659(1991).
McCafferty et al., Phage antibodies: filamentous phage displaying antibody variable domains. Nature 348:552 554 (1990).
Chothia et al., Canonical structures for the hypervariable regions of immunoglobulins. J. Mol. Biol. 196:901-917 (1987).
Chothia et al., Conformations of immunoglobulin hypervariable regions. Nature 342:878-883 (1989).
Traunecker et al., Janusin: new molecular design for bispecific reagents. International Journal of cancer. Supplement = Journal International du cancer. Supplement, Jan. 1, 1992, 7:51-52 (Abstract).
Pearson, [15] Effective protein sequence comparison. Methods Enzymol. 266:227-258 (1996) (Abstract).
Corresponding Japanese patent application No. 2019-509457 Notice of Reasons for Refusal dated Nov. 27, 2020 (translation provided).

\* cited by examiner

```
         10         20         30         40         50         60
DIVKAGITIP RNPGCPNSED KNFPRTVMVN LNIHNRNTNT NPKRSSDYYN RSTSPWNLHR 70         80         90        100        110        120
NEDPERYPSV IWEAKCRHLG CINADGNVDY HMNSVPIQQE ILVLRREPPH CPNSFRLEKI 130        140        150        160
LVSVGCTCVT PIVHHVAAAG GGESHHHHHH GDILDYKDDD DKV
```

Fig. 2

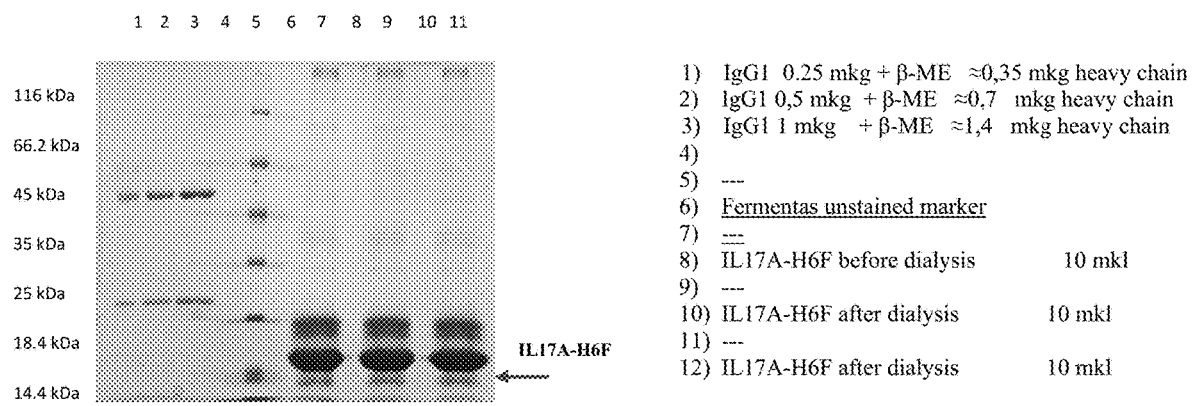

1) IgG1 0.25 mkg + β-ME ≈0,35 mkg heavy chain
2) IgG1 0,5 mkg + β-ME ≈0,7 mkg heavy chain
3) IgG1 1 mkg + β-ME ≈1,4 mkg heavy chain
4)
5) ---
6) Fermentas unstained marker
7) ---
8) IL17A-H6F before dialysis          10 mkl
9) ---
10) IL17A-H6F after dialysis          10 mkl
11) ---
12) IL17A-H6F after dialysis          10 mkl

Fig. 3

Anti-IL17A / IL17F VHH sequences

```
              10         20         30         40         50         60         70
VHH    QVQLQQSGGG SVQAGGSLRL SCAASGGTFA TSPMGWLRQA PGKEREFVAA ISPSGGDRIY DDSVKGRFTI
VHH17  EVQLQQSGGG LVQAGGSLRL SCAASGGTFA TSPMGWLRQA PGKGTEFVAA ISPSGGDRIY ADSVKGRFTI 80         90        100        110        120
VHH    SRDNAGYFIY LQMNSLKPED TARYYCAVRR RFDGTSYYTG DYDSWGQGTL VTVSS
VHH17  SRDNAGNFIY LQMNSLKPED TAVYYCAVRR RFDGTSYYTG DYDSWGQGTL VTVSS
```

Anti- TNFα variable domains of patent [RU 2303604]

VH gh3hTNF40.4

```
         10         20         30         40         50         60
EVQLVESGGG LVQPGGSLRL SCAASGYVFT DYGMNWVRQA PGKGLEWMGW INTYIGEPIY
         70         80         90        100        110
ADSVKGRFTF SLDTSKSTAY LQMNSLRAED TAVYYCARGY RSYAMDYWGQ GTLVTVSS
```

VK hTNF40-gL1

```
         10         20         30         40         50         60
DIQMTQSPSS LSASVGDRVT ITCKASQNVG TNVAWYQQKP GKAPKALIYS ASFLYSGVPY
         70         80         90        100
RFSGSGSGTD FTLTISSLQP EDFATYYCQQ YNIYPLTFGQ GTKVEIK
```

Fig.9

| Mutant name | Mutation | Oligo Pairs name | The final sequence of mutants in the variable domains of anti-TNF antibodies (replacements in CDRs are marked in gray) |
|---|---|---|---|
| VKY92F | Y92F | 1bcertL3/2fcertL392F | DIQMTQSPSSLSASVGDRVTITC KASQNVGTNVA WYQQKPGKAPKALIY SASFLYS GVPYRFSGSGSGTDFTLTISSLQPEDFATYYC QQFNIYPLT FGQGTKVEIK |
| VKY94F | Y94F | 3bcertL3/4fcertL394F | DIQMTQSPSSLSASVGDRVTITC KASQNVGTNVA WYQQKPGKAPKALIY SASFLYS GVPYRFSGSGSGTDFTLTISSLQPEDFATYYC QQYNIFPLT FGQGTKVEIK |
| VKS50A | S50A | 5bcertL2/6fcertL250A | DIQMTQSPSSLSASVGDRVTITC KASQNVGTNVA WYQQKPGKAPKALIY AASFLYS GVPYRFSGSGSGTDFTLTISSLQPEDFATYYC QQYNIYPLT FGQGTKVEIK |
| VKS50D | S50D | 5bcertL2/7fcertL250D | DIQMTQSPSSLSASVGDRVTITC KASQNVGTNVA WYQQKPGKAPKALIY DASFLYS GVPYRFSGSGSGTDFTLTISSLQPEDFATYYC QQYNIYPLT FGQGTKVEIK |
| VKS50G | S50G | 5bcertL2/8fcertL250G | DIQMTQSPSSLSASVGDRVTITC KASQNVGTNVA WYQQKPGKAPKALIY GASFLYS GVPYRFSGSGSGTDFTLTISSLQPEDFATYYC QQYNIYPLT FGQGTKVEIK |
| VKN33D | N33G | 9bcertL1/10fcertL133D | DIQMTQSPSSLSASVGDRVTITC KASQNVGTDVA WYQQKPGKAPKALIY SASFLYS GVPYRFSGSGSGTDFTLTISSLQPEDFATYYC QQYNIYPLT FGQGTKVEIK |
| VKN33A | N33A | 9bcertL1/11fcertL133A | DIQMTQSPSSLSASVGDRVTITC KASQNVGTAVA WYQQKPGKAPKALIY SASFLYS GVPYRFSGSGSGTDFTLTISSLQPEDFATYYC QQYNIYPLT FGQGTKVEIK |
| VHG33A | G33A | 12bcertH11/13fcertH133A | EVQLVESGGGLVQPGGSLRLSCAASGYVFT DYAMN WVRQAPGKGLEWMG WINTYIGEPIYADSVKG RFTFSLDTSKSTAYLQMNSLRAEDTAVYYCAR GYRSYAMDY WGQGTLVTVSS |
| VHG33S | G33S | 12bcertH11/14fcertH133S | EVQLVESGGGLVQPGGSLRLSCAASGYVFT DYSMN WVRQAPGKGLEWMG WINTYIGEPIYADSVKG RFTFSLDTSKSTAYLQMNSLRAEDTAVYYCAR GYRSYAMDY WGQGTLVTVSS |
| VHN35A | N35A | 15bcertH12/16fcertH135A | EVQLVESGGGLVQPGGSLRLSCAASGYVFT DYGMA WVRQAPGKGLEWMG WINTYIGEPIYADSVKG RFTFSLDTSKSTAYLQMNSLRAEDTAVYYCAR GYRSYAMDY WGQGTLVTVSS |
| VHN35H | N35H | 15bcertH12/17fcertH135H | EVQLVESGGGLVQPGGSLRLSCAASGYVFT DYGMH WVRQAPGKGLEWMG WINTYIGEPIYADSVKG RFTFSLDTSKSTAYLQMNSLRAEDTAVYYCAR GYRSYAMDY WGQGTLVTVSS |
| VHN52T | N52T | 18bcertH2/19fcertH252T | EVQLVESGGGLVQPGGSLRLSCAASGYVFT DYGMN WVRQAPGKGLEWMG WITTYIGEPIYADSVKG RFTFSLDTSKSTAYLQMNSLRAEDTAVYYCAR GYRSYAMDY WGQGTLVTVSS |
| VHN52Q | N52Q | 18bcertH2/19fcertH252T | EVQLVESGGGLVQPGGSLRLSCAASGYVFT DYGMN WVRQAPGKGLEWMG WIQTYIGEPIYADSVKG RFTFSLDTSKSTAYLQMNSLRAEDTAVYYCAR GYRSYAMDY WGQGTLVTVSS |

Fig.10

| Name | Plasmids combination for transient expression (with mutations in the CDRs anti-TNF IgG) | Expression level (mg/l) | Ab concentration | Sample Volume |
|---|---|---|---|---|
| MabC | pEE-aTNF-IgG1HcLALA + pEE-VHH17-77N-aTNFLc | 120,5 | 1132,4 мкг/мл | ~500 мкл |
| Mab 1 | pEE-aTNF-IgG1HcLALA-G33A + pEE-VHH17-77N-aTNFLc-Y92F | 110,5 | 680,1 мкг/мл | ~500 мкл |
| Mab 2 | pEE-aTNF-IgG1HcLALA-G33A + pEE-VHH17-77N-aTNFLc-Y94F | 100,3 | 656,5 мкг/мл | ~500 мкл |
| Mab 3 | pEE-aTNF-IgG1HcLALA-G33A + pEE-VHH17-77N-aTNFLc-S50A | 121,6 | 947 мкг/мл | ~500 мкл |
| Mab 4 | pEE-aTNF-IgG1HcLALA-G33A + pEE-VHH17-77N-aTNFLc-S50D | 116,1 | 886,2 мкг/мл | ~500 мкл |
| Mab 5 | pEE-aTNF-IgG1HcLALA-G33A + pEE-VHH17-77N-aTNFLc-S50G | 123,2 | 893,6 мкг/мл | ~500 мкл |
| Mab 6 | pEE-aTNF-IgG1HcLALA-G33S + pEE-VHH17-77N-aTNFLc-Y92F | 127,7 | 869,2 мкг/мл | ~500 мкл |
| Mab 7 | pEE-aTNF-IgG1HcLALA-G33S + pEE-VHH17-77N-aTNFLc-Y94F | 126,7 | 852,5 мкг/мл | ~500 мкл |
| Mab 8 | pEE-aTNF-IgG1HcLALA-G33S + pEE-VHH17-77N-aTNFLc-S50A | 139,9 | 827,1 мкг/мл | ~500 мкл |
| Mab 9 | pEE-aTNF-IgG1HcLALA-G33S + pEE-VHH17-77N-aTNFLc-S50D | 82.4 | 970,7 мкг/мл | ~850 мкл |
| Mab 10 | pEE-aTNF-IgG1HcLALA-G33S + pEE-VHH17-77N-aTNFLc-S50G | 100.1 | 1126,6 мкг/мл | ~850 мкл |
| Mab 11 | pEE-aTNF-IgG1HcLALA-N35S + pEE-VHH17-77N-aTNFLc-Y92F | 106.2 | 1221,5 мкг/мл | ~850 мкл |
| Mab 12 | pEE-aTNF-IgG1HcLALA-N35S + pEE-VHH17-77N-aTNFLc-Y94F | 104.9 | 998,4 мкг/мл | ~850 мкл |
| Mab 13 | pEE-aTNF-IgG1HcLALA-N35S + pEE-VHH17-77N-aTNFLc-S50A | 106.3 | 998,4 мкг/мл | ~850 мкл |
| Mab 14 | pEE-aTNF-IgG1HcLALA-N35S + pEE-VHH17-77N-aTNFLc-S50D | 94.3 | 857,1 мкг/мл | ~850 мкл |
| Mab 15 | pEE-aTNF-IgG1HcLALA-N35S + pEE-VHH17-77N-aTNFLc-S50G | 102.6 | 1004,4 мкг/мл | ~850 мкл |
| Mab 16 | pEE-aTNF-IgG1HcLALA-N35H + pEE-VHH17-77N-aTNFLc-Y92F | 110.0 | 1240,7 мкг/мл | ~850 мкл |
| Mab 17 | pEE-aTNF-IgG1HcLALA-N35H + pEE-VHH17-77N-aTNFLc-Y94F | 113,4 | 1228,2 мкг/мл | ~500 мкл |
| Mab 18 | pEE-aTNF-IgG1HcLALA-N35H + pEE-VHH17-77N-aTNFLc-S50A | 155,3 | 1853,6 мкг/мл | ~500 мкл |
| Mab 19 | pEE-aTNF-IgG1HcLALA-N35H + pEE-VHH17-77N-aTNFLc-S50D | 138,1 | 1664,9 мкг/мл | ~500 мкл |
| Mab 20 | pEE-aTNF-IgG1HcLALA-N35H + pEE-VHH17-77N-aTNFLc-S50G | 151,0 | 1932,5 мкг/мл | ~500 мкл |
| Mab 21 | pEE-aTNF-IgG1HcLALA-N52T + pEE-VHH17-77N-aTNFLc-Y92F | 141,2 | 1706,9 мкг/мл | ~500 мкл |
| Mab 22 | pEE-aTNF-IgG1HcLALA-N52T + pEE-VHH17-77N-aTNFLc-Y94F | 148,1 | 1542,3 мкг/мл | ~500 мкл |
| Mab 23 | pEE-aTNF-IgG1HcLALA-N52T + pEE-VHH17-77N-aTNFLc- S50A | 168,4 | 1593,2 мкг/мл | ~500 мкл |
| Mab 24 | pEE-aTNF-IgG1HcLALA-N52T + pEE-VHH17-77N-aTNFLc- S50D | 155,0 | 1422,4 мкг/мл | ~500 мкл |
| Mab 25 | pEE-aTNF-IgG1HcLALA-N52T + pEE-VHH17-77N-aTNFLc- S50G | 105,8 | 1123,2 мкг/мл | ~500 мкл |
| Mab 26 | pEE-aTNF-IgG1HcLALA-N52Q + pEE-VHH17-77N-aTNFLc-Y92F | 110,6 | 1264,3 мкг/мл | ~500 мкл |
| Mab 27 | pEE-aTNF-IgG1HcLALA-N52Q + pEE-VHH17-77N-aTNFLc-Y94F | 111,4 | 1343,1 мкг/мл | ~500 мкл |
| Mab 28 | pEE-aTNF-IgG1HcLALA-N52Q + pEE-VHH17-77N-aTNFLc- S50A | 119,5 | 1445,8 мкг/мл | ~500 мкл |
| Mab 29 | pEE-aTNF-IgG1HcLALA-N52Q + pEE-VHH17-77N-aTNFLc- S50D | 104,5 | 1296 мкг/мл | ~500 мкл |
| Mab 30 | pEE-aTNF-IgG1HcLALA-N52Q + pEE-VHH17-77N-aTNFLc- S50G | 130,5 | 1427,5 мкг/мл | ~500 мкл |
| Mab 31 | pEE-aTNF-IgG1HcLALA-N35S + pEE-VHH17-77N-aTNFLc- N33D | 123,0 | 1006 мкг/мл | ~500 мкл |
| Mab 32 | pEE-aTNF-IgG1HcLALA- N35S + pEE-VHH17-77N-aTNFLc- N33A | 111,5 | 930,5 мкг/мл | ~500 мкл |

Fig. 11

| Name | Plasmids combination for transient expression (with mutations in the CDRs anti-TNF IgG) | ED50 Mabi/ ED50 MabC | ED50 Mabi/ ED50 adaMab |
|---|---|---|---|
| MabC | pEE-aTNF-IgG1HcLALA + pEE-VHH17-77N-aTNFLc | 1 | 0,1 |
| Mab 1 | pEE-aTNF-IgG1HcLALA-G33A + pEE-VHH17-77N-aTNFLc-Y92F | 50 | 5 |
| Mab 2 | pEE-aTNF-IgG1HcLALA-G33A + pEE-VHH17-77N-aTNFLc-Y94F | 300 | 30 |
| Mab 3 | pEE-aTNF-IgG1HcLALA-G33A + pEE-VHH17-77N-aTNFLc-S50A | 50 | 5 |
| Mab 4 | pEE-aTNF-IgG1HcLALA-G33A + pEE-VHH17-77N-aTNFLc-S50D | 200 | 20 |
| Mab 5 | pEE-aTNF-IgG1HcLALA-G33A + pEE-VHH17-77N-aTNFLc-S50G | 100 | 10 |
| Mab 6 | pEE-aTNF-IgG1HcLALA-G33S + pEE-VHH17-77N-aTNFLc-Y92F | 20 | 2 |
| Mab 7 | pEE-aTNF-IgG1HcLALA-G33S + pEE-VHH17-77N-aTNFLc-Y94F | 70 | 7 |
| Mab 8 | pEE-aTNF-IgG1HcLALA-G33S + pEE-VHH17-77N-aTNFLc-S50A | 20 | 2 |
| Mab 9 | pEE-aTNF-IgG1HcLALA-G33S + pEE-VHH17-77N-aTNFLc-S50D | 100 | 10 |
| Mab 10 | pEE-aTNF-IgG1HcLALA-G33S + pEE-VHH17-77N-aTNFLc-S50G | 70 | 7 |
| Mab 11 | pEE-aTNF-IgG1HcLALA-N35S + pEE-VHH17-77N-aTNFLc-Y92F | 7 | 0,7 |
| Mab 12 | pEE-aTNF-IgG1HcLALA-N35S + pEE-VHH17-77N-aTNFLc-Y94F | 3 | 0,3 |
| Mab 13 | pEE-aTNF-IgG1HcLALA-N35S + pEE-VHH17-77N-aTNFLc-S50A | 5 | 0,5 |
| Mab 14 | pEE-aTNF-IgG1HcLALA-N35S + pEE-VHH17-77N-aTNFLc-S50D | 20 | 2 |
| Mab 15 | pEE-aTNF-IgG1HcLALA-N35S + pEE-VHH17-77N-aTNFLc-S50G | 9 | 0,9 |
| Mab 16 | pEE-aTNF-IgG1HcLALA-N35H + pEE-VHH17-77N-aTNFLc-Y92F | 15 | 1,5 |
| Mab 17 | pEE-aTNF-IgG1HcLALA-N35H + pEE-VHH17-77N-aTNFLc-Y94F | 12 | 1,2 |
| Mab 18 | pEE-aTNF-IgG1HcLALA-N35H + pEE-VHH17-77N-aTNFLc-S50A | 5 | 0,5 |
| Mab 19 | pEE-aTNF-IgG1HcLALA-N35H + pEE-VHH17-77N-aTNFLc-S50D | 15 | 1,5 |
| Mab 20 | pEE-aTNF-IgG1HcLALA-N35H + pEE-VHH17-77N-aTNFLc-S50G | 15 | 1,5 |
| Mab

TRISPECIFIC ANTIBODIES AGAINST IL-17A, IL-17F AND OTHER PRO-INFLAMMATORY MOLECULE

REFERENCE TO A SEQUENCE LISTING SUBMITTED VIA EFS-WEB

The content of the ASCII text file of the sequence listing named "P1947US00-SEQ-US_BCD-121_PCTRU2016050073_SL_amend" which is 31.4 kb in size was created on May 2, 2022 and electronically submitted herewith via EFS-Web is incorporated herein by reference.

BACKGROUND OF THE INVENTION

The main function of the immune system is to protect body against infections, such as bacteria or viruses, as well as from cancer lesion. The immune response includes inflammation, i.e., accumulation of immune cells systematically or in a particular part of the body. Cells of the immune system include several types of myeloid and lymphoid cells, such as monocytes, macrophages, dendritic cells, eosinophils, T cells, B cells and neutrophils. In response to an infection or foreign substance, immune cells secrete signaling proteins known as cytokines which, in turn, modulate the proliferation, development, differentiation, and/or migration of immune cells. In some cases, the immune response can result in pathological processes, such as autoimmune diseases (see e.g., Abbas et al. (eds.) (2000) Cellular and Molecular Immunology, W.B. Saunders Co., Philadelphia, Pa.; Oppenheim and Feldmann (eds.) (2001) Cytokine Reference, Academic Press, San Diego, Calif.; von Andrian and Mackay, *New Engl J Med* 343:1020-1034 (2000); Davidson and Diamond, *New Engl J Med* 345:340-350 (2001)).

CD4+ T-cells play a central role in immune responses, aiding other cells of the adaptive or innate immune system. Early research identified two classes of CD4+ T-cells (Th1 and Th2). Recently, a new subset of CD4+ T cells has been identified: Th17 cells. Th17 cells have emerged as an offshoot of the adaptive immune system, specializing in strengthening the protection of the host against extracellular bacteria and some fungi and bacteria from which Th1 and Th2 cells do not provide protection.

Th17 cells have been identified in the context of discovery of a new family of cytokines, the IL-17 family, which consists of six members at present (IL-17A-F). IL-17 (previously called CTLA-8) is substantially expressed by Th17-cells and has been designated as IL-17A, as the original molecule in the IL-17 cytokine family. The sequences of IL-17 family members do not have homology with other currently known mammalian proteins; thus, the IL-17 family constitutes a separate family of cytokines. The structural features of IL-17 family members, established on the basis of the crystal structure of IL-17F, are similar to many cytokines; each of the family members is likely produced as a homodimer, although structural analyses imply that heterodimers may be present as well. More recently, it has been found that heterodimeric IL-17A and IL-17F, expressed by activated CD4+ T cells, transmits a signal through a complex of IL-17R/IL-17RC (Wright J. F. et al., *J Immunol* 181: 2799-2805 (2001)).

The gene encoding human IL-17F is located adjacent to the gene encoding human IL-17A (Hymowitz et al., *Embo J* 20(19):5332-41 (2001)). IL-17A and IL-17F have 44% amino acid sequence identity, while other members of the IL-17 family have lower sequence identity (15-27%). This suggests that IL-17A and IL-17F form a special subgroup of the IL-17 family (Starnes et al., *J Immunol* 167(8):4137-40 (2001); Aggarwal and Gurney, *J. Leukoc Biol* 71(1): 1-8 (2002)). It has been found that the biological effects of IL-17F are similar to those of IL-17A, e.g., the ability to stimulate the production of IL-6, IL-8 and G-CSF in a wide variety of cells. Like IL-17A, IL-17F is able to induce the secretion of cartilage matrix and inhibit the synthesis of new cartilage matrix (see US 2002/0177188). Thus, like IL-17A, IL-17F may contribute to the pathology of inflammatory diseases. Recently, the authors observed that both IL-17A and IL-17F are induced in T-cells exposed to interleukin 23 (IL-23) (Aggarwal et al., *J Biol Chem* 278(3): 1910-4 (2003)). The observation that IL-17A and IL-17F have similar chromosomal localization and significant sequence similarity, and the fact that IL-17A and IL-17F are induced in the same cell populations in response to specific stimuli, led to the identification of a new human cytokine that contains a covalent heterodimer of IL-17A and IL-17F.

Further, IL-17A acts synergistically with tumor necrosis factor alpha (TNFα) and interleukin-1 beta (IL-1β) to achieve a significant pro-inflammatory state. To treat a variety of inflammatory, immune, and proliferative conditions, including rheumatoid arthritis (RA), osteoarthritis, rheumatoid arthritis osteoporosis, inflammatory fibrosis (e.g., scleroderma, pulmonary fibrosis and cirrhosis), gingivitis, periodontosis or periodontal diseases, inflammatory bowel diseases (e.g., Crohn's disease, ulcerative colitis and inflammatory bowel disease), asthma (including allergic asthma), allergies, chronic obstructive pulmonary disease (COPD), multiple sclerosis, psoriasis, cancer and others, it was proposed to reduce the activity of IL-17A with antibodies or antigen-binding antibody fragments that are antagonists of these molecules (see, e.g., US 2003/0166862, WO 2005/108616, WO 2005/051422, and WO 2006/013107).

TNFα antagonists are known to treat arthritis by reducing inflammation and inhibiting the progression of cartilage and bone destruction (van den Berg, *Arthritis Res* 3: 18-26 (2001)). However, a significant percentage of patients have an inadequate response to TNFα antagonist-containing drugs. Preclinical research shows that TNFα and IL-17A exhibit the same properties in the pathophysiology of arthritis. While singly TNFα and IL-17A have a negligible effect on the expression of inflammatory genes, their combination leads to a strong synergistic response. The interaction of TNFα and IL-17A increases the expression of cytokines (LeGrand et al., *Arthritis Rheum* 44:2078-2083 (2001)) and pro-inflammatory chemokines (Chabaud et al., *J. Immunol* 167:6015-6020 (2001)), and also induces cartilage and bone destruction (Van Bczooijen et al., *Ann Rheum Pis* 61:870-876 (2002)).

Currently there is a number of IL-17A bispecific antibodies and other pro-inflammatory molecules, e.g., DVD (Abbott) and COVA322 (Covagen-Janssen).

International Patent Publication No. WO 2015/014979 describes IL-17A and TNFα tetravalent bispecific antibodies, which contain two binding sites for IL-17A and two binding sites for TNFα. These antibodies demonstrated a synergistic effect in inhibiting inflammation and tissue destruction in rheumatoid arthritis.

International Patent Application WO 2014/137961 describes IL-17A and TNFα bispecific antibodies that comprise two polypeptides. These bispecific antibodies are thermally and chemically stable, exhibit low aggregation ability, and can simultaneously bind to IL-17A and TNFα.

U.S. Pat. No. 8,496,936 describes IL-17A, IL-17F and IL-23p19 tri-specific antibodies that exhibit different activities against various ligands in cellular assays and in vivo animal models, but did not show any physical-chemical characteristics necessary to create stable formulation candidates.

The production of antibodies that can effectively neutralize IL-17A, IL-17F, and TNFα activity in the context of inflammatory reactions and autoimmune disease, especially antibodies that remain stable in formulation, remains relevant. The content of this section does not constitute an admission of prior art.

SUMMARY OF THE INVENTION

The present invention provides tri-specific binding molecules directed against IL-17A, IL-17F and a pro-inflammatory molecule such as TNFα. Such antibodies may be used for treatment of autoimmune and/or inflammatory disorders such as rheumatoid arthritis, psoriasis, and psoriatic arthritis. Compared to currently available treatments for such disorders, including antibody treatments, it is contemplated that the tri-specific binding molecules of the invention may provide a superior clinical response either alone or in combination with other anti-inflammatory and/or immunosuppressive therapies.

In one aspect, the invention provides a tri-specific binding molecule comprising a first binding domain that binds to human IL-17A and human IL-17-F and a second binding domain that binds to a human pro-inflammatory molecule. In certain embodiments, the human pro-inflammatory molecule is human TNFα. In a particular embodiment, the binding molecule is an antibody or an antigen-binding portion thereof.

In some embodiments, the first binding domain comprises the amino acid sequence of SEQ ID NO: 3. In some embodiments, the first binding domain comprises the amino acid sequences of SEQ ID NOs: 1-3. In some embodiments, the first binding domain competes for binding with or binds to the same epitope as a binding domain comprising the amino acid sequence of SEQ ID NO: 4. In some embodiments, the first binding domain is at least 90% identical in sequence to the amino acid sequence of SEQ ID NO: 4. In certain embodiments, the first binding domain comprises the amino acid sequence of SEQ ID NO: 4. In a particular embodiment, the first binding domain consists of the amino acid sequence of SEQ ID NO: 4.

In some embodiments, the first binding domain is humanized. In certain embodiments, the first binding domain is a humanized VHH.

In some embodiments, the second binding domain competes for binding with or binds to the same epitope as a binding domain comprising:

a heavy chain comprising the amino acid sequences of SEQ ID NOs: 10-12 and a light chain comprising the amino acid sequences of SEQ ID NOs: 13-15;

a heavy chain variable domain comprising the amino acid sequence of SEQ ID NO: 8 and a light chain variable domain comprising the amino acid sequence of SEQ ID NO: 9; or a heavy chain comprising the amino acid sequence of SEQ ID NO: 5 and a light chain comprising the amino acid sequence of SEQ ID NO: 6.

In some embodiments, the second binding domain comprises a heavy chain comprising the amino acid sequence of SEQ ID NO: 12 and a light chain comprising the amino acid sequence of SEQ ID NO: 15. In some embodiments, the second binding domain comprises a heavy chain comprising the amino acid sequences of SEQ ID NOs: 10-12 and a light chain comprising the amino acid sequences of SEQ ID NOs: 13-15. In some embodiments, the second binding domain comprises a heavy chain variable domain at least 90% identical in sequence to the amino acid sequence of SEQ ID NO: 8, a variable domain at least 90% identical to the amino acid sequence of SEQ ID NO: 9, or both. In some embodiments, the second binding domain comprises a heavy chain variable domain comprising the amino acid sequence of SEQ ID NO: 8, a light chain variable domain comprising the amino acid sequence of SEQ ID NO: 9, or both. In a particular embodiment, the second binding domain comprises a heavy chain variable domain consisting of the amino acid sequence of SEQ ID NO: 8 and a light chain variable domain consisting of the amino acid sequence of SEQ ID NO: 9.

In some embodiments, the second binding domain is a chimeric antibody, a humanized antibody, a human antibody, a single chain antibody, Fv, Fab, F(ab')$_2$, Fd, single chain Fv molecule (scFv), diabody, or single domain antibody (dAb). In some embodiments, the second binding domain is a humanized Fab.

In some embodiments, the second binding domain comprises a heavy chain at least 90% identical in sequence to the amino acid sequence of SEQ ID NO: 5, a light chain at least 90% identical in sequence to the amino acid sequence of SEQ ID NO: 6, or both. In some embodiments, the second binding domain comprises a heavy chain comprising the amino acid sequence of SEQ ID NO: 5, a light chain comprising the amino acid sequence of SEQ ID NO: 6, or both. In a particular embodiment, the second binding domain comprises a heavy chain consisting of the amino acid sequence of SEQ ID NO: 5 and a light chain consisting of the amino acid sequence of SEQ ID NO: 6.

In one embodiment, the invention provides a tri-specific binding molecule comprising any of the first binding domains described herein in combination with any of the second binding domains described herein.

In one embodiment, the invention provides a tri-specific binding molecule comprising a first binding domain that binds to human IL-17A and human IL-17F and a second binding domain that binds to human TNFα, wherein said first binding domain comprises the amino acid sequence of SEQ ID NO: 4 and said second binding domain comprises a heavy chain comprising the amino acid sequence of SEQ ID NO: 5 and a light chain comprising the amino acid sequence of SEQ ID NO: 6.

In one embodiment, the invention provides a tri-specific binding molecule comprising a first binding domain that binds to human IL-17A and human IL-17F and a second binding domain that binds to human TNFα, wherein said first binding domain comprises the amino acid sequence of SEQ ID NO: 4 and said second binding domain comprises a heavy chain comprising the amino acid sequence of SEQ ID NO: 8 and a light chain comprising the amino acid sequence of SEQ ID NO: 9.

In one embodiment, the invention provides a tri-specific binding molecule that binds to human IL-17A, human IL-17F, and human TNFα, wherein said binding molecule comprises the amino acid sequences of SEQ ID NOs: 5 and 7.

In some embodiments, the first binding domain and the second binding domain are joined by a peptide linker of greater than five amino acids. In certain embodiments, the amino acid residues of the peptide linker are selected from G, A, S, P, E, T, D, and K. In a particular embodiment, the peptide linker comprises the amino acid sequence of SEQ ID NO: 16. The first binding domain may be joined to the N-terminus or the C-terminus of either the heavy or light chain of the second binding domain via the peptide linker.

In some embodiments, the binding molecule is an antibody of isotype IgG or an antigen-binding portion thereof. The antibody may be, e.g., of isotype subtype IgG1.

In some embodiments, the binding molecule comprises an $F_C$ region with at least one mutation that reduces ADCC and/or CDC in comparison to the same binding molecule without the mutation.

In some embodiments, the binding molecule has at least one of the following properties:
a $K_D$ for IL-17A of $10^{-11}$ M or less;
a $K_D$ for IL-17F of $10^{-7}$ M or less;
a $K_D$ for TNFα of $10^{-11}$ M or less;
inhibits the activity of IL-17A and/or IL-17A/TNFα by at least 50% (e.g., 60%, 70%, 80%, or 90%) at concentrations below 200 ng/mL in an IL-6 assay in HT1080 cells;
inhibits IL-17A-dependent IL-6 release by HT080 cells;
inhibits production of IL-6 in HT1080 cells;
inhibits TNFα-dependent cytotoxicity by at least 50% (e.g., 60%, 70%, 80%, or 90%) at concentrations below 100 ng/mL in WEHI-13VAR cells;
does not bind to rabbit, mouse, or guinea pig TNFα;
simultaneously binds to IL-17A and TNFα;
binds to cynomolgus IL-17A and TNFα;
remains stable after at least three, four, five, six, or seven days of incubation (e.g., after seven days of incubation) at 37° C. in human serum;
has a half-life of over 5, 6, 7, 8, 9, 10, 11, 12, 13, 14, or 15 days in vivo (e.g., 12 days);
has an anti-inflammatory effect in an in vivo arthritis model; and
inhibits the activity of IL-17 and TNFα in vivo.

In one aspect, the invention provides a pharmaceutical composition comprising any of the tri-specific binding molecules described herein and a pharmaceutically acceptable excipient.

In one aspect, the invention provides an isolated nucleic acid molecule comprising a nucleotide sequence that encodes the first binding domain of any of the tri-specific binding molecules described herein.

The invention also provides an isolated nucleic acid molecule comprising a nucleotide sequence that encodes the heavy chain, the light chain, or both, of the second binding domain of any of the tri-specific binding molecules described herein.

In some aspects, the invention provides an isolated nucleic acid molecule comprising:
a nucleotide sequence that encodes the first binding domain of any of the tri-specific binding molecules described herein;
a nucleotide sequence that encodes the heavy chain of the second binding domain of any of the tri-specific binding molecules described herein;
a nucleotide sequence that encodes the first binding domain of any of the tri-specific binding molecules described herein; or
any combination of the above.

In some embodiments, the isolated nucleic acid molecule comprises a nucleotide sequence that encodes the first binding domain, and a nucleotide sequence that encodes the light chain of the second binding domain, of any of the tri-specific binding molecules described herein, optionally further comprising a nucleotide sequence encoding a peptide linker. The isolated nucleic acid molecule may comprise, for example, a nucleotide sequence encoding SEQ ID NO: 4 and a nucleotide sequence encoding SEQ ID NO: 6, optionally further comprising a nucleotide sequence encoding a peptide linker. In one embodiment, the amino acid sequence of the peptide linker is SEQ ID NO: 16. In one embodiment, the isolated nucleic acid molecule encodes SEQ ID NO: 7.

In some embodiments, the isolated nucleic acid molecule encodes the amino acid sequence of any one of SEQ ID NOs: 1-15.

The invention also provides a vector comprising any of the isolated nucleic acid molecules described above, wherein said vector further comprises an expression control sequence.

The invention also provides a host cell comprising:
a nucleotide sequence that encodes the first binding domain of any of the tri-specific binding molecules described herein;
a nucleotide sequence that encodes the heavy chain of the second binding domain of any of the tri-specific binding molecules described herein; and
a nucleotide sequence that encodes the first binding domain of any of the tri-specific binding molecules described herein.

In a particular embodiment, the host cell comprises a nucleotide sequence that encodes SEQ ID NO: 5 and a nucleotide sequence that encodes SEQ ID NO: 7.

In one aspect, the invention provides a method for producing any of the tri-specific binding molecules described herein, comprising providing a host cell as described above, cultivating said host cell under conditions suitable for expression of the binding molecule, and isolating the resulting binding molecule.

In one aspect, the invention provides a method for treating a patient in need thereof, comprising administering to the patient any of the tri-specific binding molecules or pharmaceutical compositions described herein. In some embodiments, the patient has a disorder mediated by IL-17A, IL-17F, or TNFα. In a particular embodiment, the invention provides a method for treating rheumatoid arthritis, psoriasis, or psoriatic arthritis in a patient, comprising administering to the patient any of the tri-specific binding molecules or pharmaceutical compositions described herein. In some embodiments, the method further comprises administering an anti-inflammatory or immunosuppressive agent. In any of the above methods of treatment, the patient may be a human.

BRIEF DESCRIPTION OF THE FIGURES

FIG. 2 shows the protein sequence of IL-17A-His6-FLAG.

FIG. 3 is a gel showing purified IL-17A-His6-FLAG protein.

FIG. 9 shows the amino acid sequence of a high affinity VHH domain (VHH17; SEQ ID NO: 4) and its parent VHH domain (VHH; SEQ ID NO: 17) specific for human IL-17A and IL-17F. Amino acids substituted during the humanization process are shown in bold. CDRs are highlighted in gray. FIG. 9 also shows the heavy and light chain variable domain amino acid sequences (SEQ ID NOs: 18 and 9, respectively) of an anti-human TNFα antibody (RU 2303604).

FIG. 10 shows a table of mutations in the CDRs of anti-TNFα antibody variants used as part of anti-IL-17A/anti-IL-17F/anti-TNFα tri-specific antibodies (from top to bottom, SEQ ID NOs: 19-32).

FIG. 11 shows the results of transient development of different anti-IL-17A/anti-IL-17F/anti-TNFα tri-specific antibody variants.

FIG. 12 shows a comparative analysis of the anti-TNFα activity of different anti-IL-17A/anti-IL-17F/anti-TNFα tri-specific antibody variants in a cytotoxic TNFα-dependent assay using WEHI-13VAR cells. Variants with maximum inhibitory activity are marked in grey.

DETAILED DESCRIPTION OF THE INVENTION

Definitions and General Techniques

Figure 1:
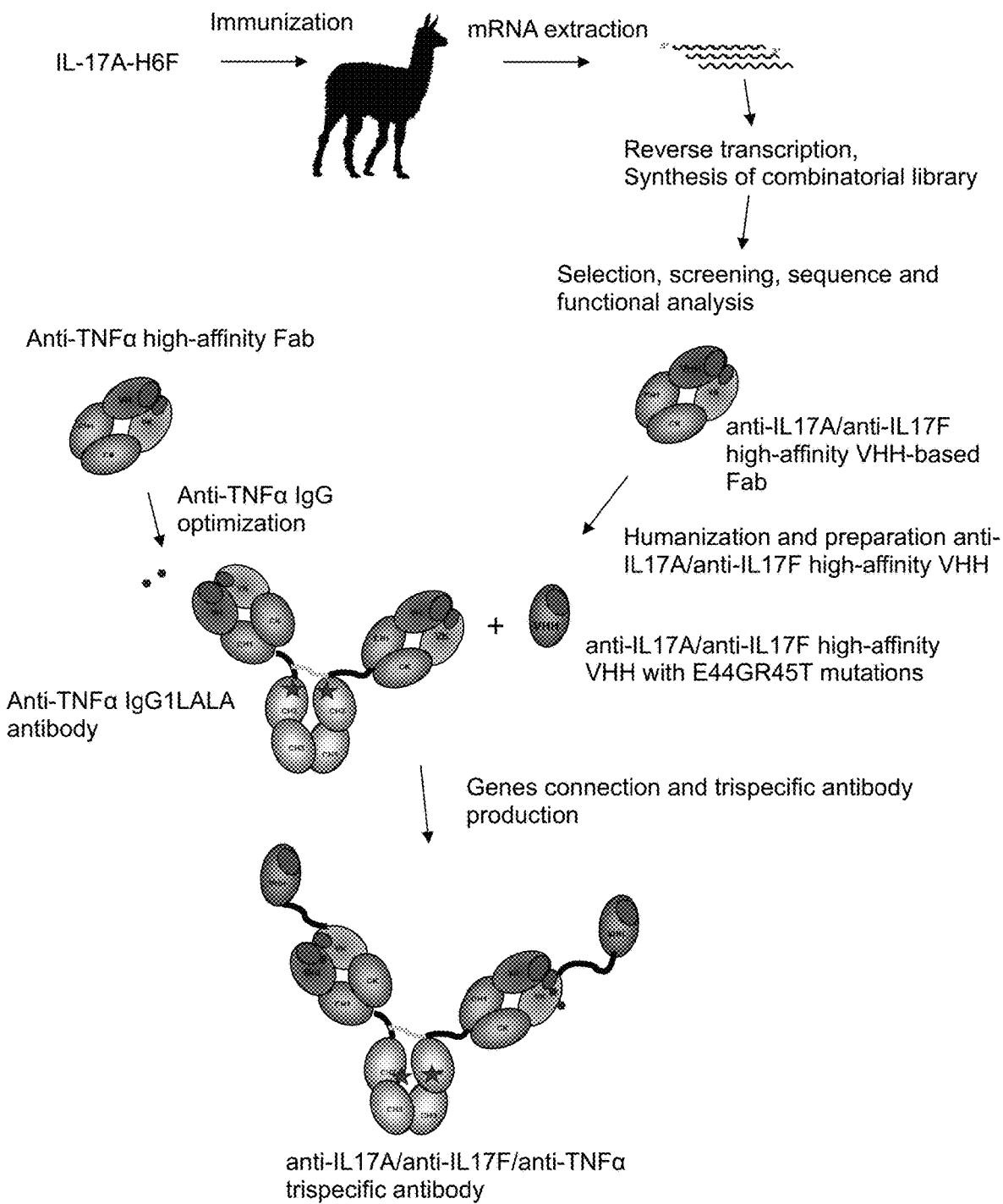
FIG. 1 shows a schematic of production of the tri-specific anti-IL-17A/anti-IL-17F/anti-TNFα antibody.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art.

Further, unless otherwise required by context, singular terms shall include pluralities and plural terms shall include the singular. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Throughout this specification and embodiments, the words "have" and "comprise," or variations such as "has," "having," "comprises," or "comprising," will be understood to imply the inclusion of a stated integer or group of integers but not the exclusion of any other integer or group of integers.

Antibody-Related Definitions

Unless otherwise stated, as used herein, "IL-17A," "IL-17F," and "TNFα" refer to human IL-17A, IL-17F, and TNFα, respectively.

Interleukin-17 ("IL-17") is a 20-30 kD glycosylated homodimeric protein. The IL-17A human gene encodes a 155 amino acid protein, which has a 19 amino acid signal sequence and a 136 amino acid mature segment. The IL-17F human gene encodes a 163 amino acid protein, which has a 30 amino acid signal sequence and a 133 amino acid mature segment. A human IL-17A polypeptide sequence is available under Uniprot Accession No. Q16552. A human IL-17F polypeptide sequence is available under Uniprot Accession No. Q96PD4.

The term "Tumor Necrosis Factor alpha" or "TNFα," as used herein, refers to a human TNFα molecule having the polypeptide sequence described in Pennica et al., *Nature* 312:721 (1984) or in Aggarwal et al., *JBC* 260:2345 (1985).

The terms "immune response," "autoimmune reaction," and "autoimmune inflammation" refer to, for example, the action of lymphocytes, antigen presenting cells, phagocytic cells, granulocytes, and soluble macromolecules produced by the above cells or the liver (including antibodies, cytokines, and complement that result in selective damage, destruction, or elimination from the human body of invading pathogens, cells or tissues infected with pathogens, cancerous cells, or, in cases of autoimmunity or pathological inflammation, normal human cells or tissues).

The term "binding molecule" encompasses antibodies and immunoglobulins. The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acids to each region may be in accordance with IMGT® definitions (Lefranc et al., *Dev Comp Immunol* 27(1):55-77 (2003); or the definitions of Kabat, *Sequences of Proteins of Immunological Interest* (National Institutes of Health, Bethesda, Md. (1987 and 1991)); Chothia & Lesk, *J. Mol. Biol.* 196:901-917 (1987); or Chothia et al., *Nature* 342:878-883 (1989).

In some embodiments, an antibody or immunoglobulin as described herein may comprise in addition to the heavy and light chains a VHH domain, or "nanobody." These single domains are the antigen-binding parts of heavy chain antibodies (hcAb), which are devoid of light chains and are typically found in camelid species such as llamas and alpacas.

The term "antigen-binding portion" of an antibody (or simply "antibody portion"), as used herein, refers to one or more portions or fragments of an antibody that retain the ability to specifically bind to an antigen (e.g., human IL-17A, human IL-17F, TNFα, or portions thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the $V_L$, $V_H$, $C_L$ and $C_H1$ domains; (ii) a F(ab')$_2$ fragment: a bivalent fragment comprising two Fab fragments linked by a disulfide bridge at the hinge region; (iii) an Fd fragment consisting of the $V_H$ and $C_H1$ domains; (iv) a Fv fragment consisting of the $V_L$ and $V_H$ domains of a single arm of an antibody, (v) a single domain antibody (dAb) fragment, which consists of a $V_H$ domain; and (vi) an isolated complementarity determining region (CDR) capable of specifically binding to an antigen. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv (scFv)). Also, within the invention are antigen-binding molecules comprising a $V_H$ and/or a $V_L$. In the case of a $V_H$, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesion molecules can be obtained using standard recombinant DNA techniques, e.g., as described herein.

The term "recombinant antibody" refers to an antibody that is expressed from a cell or cell line comprising the nucleotide sequence(s) that encode the antibody, wherein said nucleotide sequence(s) are not naturally associated with the cell.

The term "variant" antibody as used herein refers to an antibody having an amino acid sequence which differs from the amino acid sequence of its "parent" antibody by addition, deletion and/or substitution of one or more amino acid residues relative to the parent antibody sequence. In a preferred embodiment, the variant antibody comprises at least one or more (for example, from one to about twelve, e.g., two, three, four, five, six, seven, eight, or nine, ten, eleven, or twelve; and in some embodiments, from one to about ten) amino acid additions, deletions, and/or substitutions relative to the parent antibody. In some embodiments, the amino acid additions, deletions, and/or substitutions are in the CDRs of the variant antibody. Identity or homology with respect to the variant antibody sequence is defined herein as the percentage of amino acid residues in the variant antibody sequence that are identical to the parent antibody residues, after aligning the sequences and introducing gaps, if necessary, to achieve the maximum percent sequence identity. The variant antibody retains the ability to bind to the same antigen, and preferably epitope, as that to which the parent antibody binds, and in some embodiments has at least one property or bioactivity that is superior to similar properties of the parent antibody. For example, a variant antibody may have, e.g., stronger binding affinity, longer half-life, lower IC50, or enhanced ability to inhibit the biological activity of the antigen as compared to the parent antibody. A variant antibody of particular interest herein is an antibody exhibiting at least about a 2-fold (preferably at least about a 5-fold, 10-fold or 20-fold) increase in biological activity as compared to the parent antibody.

The term "chimeric antibody" refers in its broadest sense to an antibody that contains one or more regions from one antibody and one or more regions from one or more other antibodies, typically an antibody that is partially of human origin and partially of non-human origin, i.e., derived in part from a non-human animal, for example a mouse, rat or other rodent, or a camelid such as a llama or alpaca. Chimeric antibodies are preferred over non-human antibodies in order to reduce the risk of a human anti-antibody response, e.g., a human anti-mouse antibody response in the case of a murine antibody. An example of a typical chimeric antibody is one in which the variable region sequences are murine while the constant region sequences are human. In the case of a chimeric antibody, the non-human parts may be subjected to further alteration in order to humanize the antibody.

The term "humanize" refers to the fact that where an antibody is wholly or partially of non-human origin, for example a murine or llama antibody obtained from immunization of mice or llamas, respectively, with an antigen of interest or a chimeric antibody based on such a murine or llama antibody, it is possible to replace certain amino acids, in particular in the framework regions and constant domains of the heavy and light chains, in order to avoid or minimize an immune response in humans. The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, e.g., by constructing expression vectors that express CDR sequences from the specific antibody grafted into framework sequences from a different antibody. As a result, it is possible to "humanize" a non-human antibody and still substantially maintain the binding specificity and affinity of the original antibody. Although it is not possible to precisely predict the immunogenicity and thereby the human anti-antibody response of a particular antibody, non-human antibodies tend to be more immunogenic than human antibodies. Chimeric antibodies, where the foreign (e.g. rodent or camelid) constant regions have been replaced with sequences of human origin, have been shown to be generally less immunogenic than antibodies of fully foreign origin, and the trend in therapeutic antibodies is towards humanized or fully human antibodies. Chimeric antibodies or other antibodies of non-human origin thus can be humanized to reduce the risk of a human anti-antibody response.

For chimeric antibodies, humanization typically involves modification of the framework regions of the variable region sequences. Amino acid residues that are part of complementarity determining regions (CDRs) most often will not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art; see, e.g., the review by Almagro & Fransson, *Front Biosci.* 13:1619-1633 (2008). One commonly used method is CDR grafting, which for, e.g., a murine-derived chimeric antibody involves identification of human germline gene counterparts to the murine variable region genes and grafting of the murine CDR sequences into this framework. CDR grafting may be based on the Kabat CDR definitions, although a more recent publication (Magdelaine-Beuzelin et al., *Crit Rev. Oncol Hematol.* 64:210-225 (2007)) has suggested that the IMGT® definition (the international ImMunoGeneTics information System®, www.imgt.org) may improve the result of the humanization (see Lefranc et al., *Dev. Comp Immunol.* 27:55-77 (2003)). In some cases, CDR grafting may reduce the binding specificity and affinity, and thus the biological activity, of a CDR-grafted non-human antibody as compared to the parent antibody from which the CDRs are obtained. Back mutations (sometimes referred to as "framework repair") may be introduced at selected positions of the CDR-grafted antibody, typically in the framework regions, in order to reestablish the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., *Proc Natl Acad Sci USA*, 94:412-417 (1997), and the stepwise in vitro affinity maturation method of Wu et al., *Proc Natl Acad Sci USA* 95:6037-6042 (1998).

The term "isolated protein", "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

As used herein, the term "germline" refers to the nucleotide and amino acid sequences of antibody genes and gene segments as they are passed from parents to offspring via germ cells. Germline sequences are distinguished from the nucleotide sequences encoding antibodies in mature B cells, which have been altered by recombination and hypermutation events during the course of B cell maturation. An antibody that "utilizes" a particular germline sequence has a nucleotide or amino acid sequence that aligns with that germline nucleotide sequence or with the amino acid sequence that it specifies more closely than with any other germline nucleotide or amino acid sequence.

The term "affinity" refers to a measure of the attraction between an antigen and a binding molecule, e.g., an antibody. The intrinsic attractiveness of the binding molecule for the antigen is typically expressed as the binding affinity equilibrium constant ($K_D$) of a particular binding molecule-antigen interaction. A binding molecule is said to specifically bind to an antigen when the $K_D$ is ≤1 mM, preferably ≤100 nM. A $K_D$ binding affinity constant can be measured, e.g., by surface plasmon resonance (BIAcore™) or Bio-Layer Interferometry, for example using the ProteOn™ XPR36 SPR system from Bio-Rad or the Octet™ system.

The term "$k_{off}$" refers to the dissociation rate constant of a particular binding molecule-antigen interaction. A $k_{off}$ dissociation rate constant can be measured by Bio-Layer Interferometry, for example using the Octet™ system.

The term "epitope" as used herein refers to a portion (determinant) of an antigen that specifically binds to a binding molecule (e.g., and antibody or a related molecule such as a bispecific binding molecule). Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. Further, the generation and characterization of antibodies or other binding molecules may elucidate information about desirable epitopes. From this information, it is then possible to competitively screen binding molecules for binding to the same or similar epitopes, e.g., by conducting competition studies to find binding molecules that compete for binding to the antigen.

One can determine whether an antibody or other binding molecule binds to the same epitope of or cross competes for binding to IL-17A, IL-17F, or TNFα with a tri-specific binding molecule of the invention by using methods known in the art. In one embodiment, one allows the tri-specific binding molecule of the invention to bind to IL-17A, IL-17F, or TNFα under saturating conditions and then measures the ability of the test antibody to bind to said target antigen. If the test antibody is able to bind to the target antigen at the same time as the reference tri-specific binding molecule, then the test antibody binds to a different epitope than the reference tri-specific binding molecule. However, if the test antibody is not able to bind to the target antigen at the same time, then the test antibody binds to the same epitope, an overlapping epitope, or an epitope that is in close proximity to the epitope bound by the tri-specific binding molecule. This experiment can be performed using ELISA, RIA, BIACORE™, Bio-Layer Interferometry or flow cytometry.

To test whether a tri-specific binding molecule of the invention cross-competes with another binding molecule, one may use the competition method described above in two directions, i.e., determining if the known binding molecule blocks the test binding molecule and vice versa. Such cross-competition experiments may be performed e.g. using an IBIS MX96 SPR instrument or the Octet™ system.

In one embodiment, the binding molecule of the invention is a monoclonal antibody. As used herein, the acronym "mAb" refers to a monoclonal antibody, i.e., an antibody synthesized and secreted by an individual clonal population of cells. The clonal population can be a clonal population of immortalized cells. In some embodiments, the immortalized cells in the clonal population are hybrid cells—hybridomas—typically produced by the fusion of individual B lymphocytes from an immunized animal with individual cells from a lymphocytic tumour. Hybridomas are an engineered cell type and do not occur in nature.

The class (isotype) and subclass of antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various classes and subclasses of immunoglobulins, and determining the class and subclass of the antibodies.

The term "pro-inflammatory molecule" includes, but is not limited to, lymphokines, monokines, traditional polypeptide hormones, growth hormones such as human growth hormone, N-methionyl human growth hormone and cattle growth hormone, parathyroid hormone, thyroxine, insulin, proinsulin, relaxin, prorelaxin, glycoprotein hormones such as follicle stimulating hormone (FSH), thyrotrophic hormone (TSH) and luteinizing hormone (LH), hepatic growth factor, fibroblast growth factor, prolactin, placental lactogen, factor and tumor necrosis factor, Mullerian inhibiting substance, gonadotropin-associated mouse peptide, inhibin, activin, vascular endothelial growth factor, integrin, thrombopoietin (TPO), nerve growth factor and platelet-derived growth factor, transforming growth factors (TGF), insulin-like growth factors I and II, erythropoietin (EPO), osteoinductive factors, interferons, colony-stimulating factors (CSF) such as CSF macrophages (M-CSF), CSF granulocyte-macrophage (GM-CSF) and CSF granulocyte (G-CSF), interleukins (IL) such as IL-1, IL-1a, IL-2, IL-3, IL-4, IL-5, IL-6, IL-7, IL-8, IL-9, IL-10, IL-11, IL15, IL-12, IL-17A, IL-22, and IL-23, tumor necrosis factors, and other polypeptide factors inducing leukemia inhibitory factor (LIF) and kit ligand (KL). As used herein, the term "pro-inflammatory molecule" includes proteins isolated from natural sources or from recombinant cell culture and biologically active equivalents to said proteins.

Tri-Specific Anti-TNF☐☐Anti-IL-17A/Anti-IL-17F Binding Molecules

The present invention provides tri-specific binding molecules directed against IL-17A, IL-17F, and a pro-inflammatory molecule that is not IL-17A or IL-17F (e.g., TNFα). In a particular embodiment, the tri-specific binding molecules are tri-specific antibodies or antigen-binding portions thereof. The binding molecules comprise domains that bind to IL-17A, IL-17F, and a pro-inflammatory molecule (e.g., TNFα). In some embodiments, the binding molecules comprise a first binding domain that binds to IL-17A and IL-17F and a second binding domain that binds to TNFα. In some embodiments, the binding domains for IL-17A and IL-17F may be separate.

In one embodiment, a tri-specific anti-TNFα/anti-IL-17A/anti-IL-17F binding molecule of the invention competes for binding to human IL-17A and/or IL-17F with, or binds to the same epitope(s) of said antigen(s) as, a VHH comprising:
SEQ ID NOs: 1-3; or
SEQ ID NO: 4.

In one embodiment, a tri-specific anti-TNFα/IL-17A/IL-17F binding molecule of the invention competes for binding to human TNFα with, or binds to the same epitope(s) of said antigen(s) as, an antibody comprising:
SEQ ID NOs: 10-15;
SEQ ID NOs: 8 and 9; or
SEQ ID NOs: 5 and 6.

In certain embodiments, a tri-specific anti-TNFα/IL-17A/IL-17F binding molecule of the invention competes for binding to human IL-17A and/or IL-17F with, or binds to the same epitope(s) of said antigen(s) as, a VHH comprising:
SEQ ID NOs: 1-3; or
SEQ ID NO: 4;
and competes for binding to human TNFα with, or binds to the same epitope(s) of said antigen(s) as, an antibody comprising:
SEQ ID NOs: 10-15;
SEQ ID NOs: 8 and 9; or
SEQ ID NOs: 5 and 6.

In one embodiment, the tri-specific binding molecule comprises an anti-IL-17A/anti-IL-17F VHH domain. In certain embodiments, the anti-IL-17A/anti-IL-17F VHH domain is humanized. In some embodiments, the anti-IL-17A/anti-IL-17F VHH domain comprises the heavy chain CDR1 (H-CDR1) amino acid sequence of SEQ ID NO: 1, the heavy chain CDR2 (H-CDR2) amino acid sequence of SEQ ID NO: 2, the heavy chain CDR3 (H-CDR3) amino acid sequence of SEQ ID NO: 3, or any combination thereof. In one embodiment, the VHH domain comprises the H-CDR1, H-CDR2, and H-CDR3 amino acid sequences of SEQ ID NOs: 1-3. In some embodiments, the VHH domain is at least 60% identical in sequence to SEQ ID NO: 4, e.g., at least 60%, 70%, or 80% identical to SEQ ID NO: 4. In some embodiments, the VHH domain is at least 90% identical in sequence to SEQ ID NO: 4, e.g., at least 91%, 92%, 93%, 94%, 95%, 96%, 97%, 98%, or 99% identical to SEQ ID NO: 4. In a particular embodiment, the VHH domain comprises or consists of the amino acid sequence of SEQ ID NO: 4.

In one embodiment, the tri-specific binding molecule comprises an anti-human TNFα antibody or an antigen-binding portion thereof. In certain embodiments, the anti-human TNF-alpha antibody is a humanized antibody or an antigen-binding portion thereof (e.g., a humanized Fab).

In some embodiments, the heavy chain of the anti-human TNFα antibody comprises the H-CDR1 amino acid sequence of SEQ ID NO: 10, the H-CDR2 amino acid sequence of SEQ ID NO: 11, the H-CDR3 amino acid sequence of SEQ ID NO: 12, or any combination thereof. In one embodiment, the heavy chain of the anti-human TNFα antibody comprises the H-CDR1, H-CDR2, and H-CDR3 amino acid sequences of SEQ ID NOs: 10-12. In some embodiments, the heavy chain of the anti-human TNFα antibody has a heavy chain variable domain (VH) that is at least 60% identical in sequence to SEQ ID NO: 8, e.g., at least 60%, 70%, or 80% identical to SEQ ID NO: 8. In some embodiments, the heavy chain of the anti-human TNFα antibody has a heavy chain variable domain (VH) that is at least 90% identical in sequence to SEQ ID NO: 8, e.g., at least 91%, 92%, 93%, 94%, 95%, 96%, 97%, 98%, or 99% identical to SEQ ID NO: 8. In a particular embodiment, the VH comprises or consists of the amino acid sequence of SEQ ID NO: 8. The VH may be joined to a heavy chain constant domain (CH) of isotype IgG, an IgM, an IgE, an IgA, or an IgD molecule. In certain embodiments, the CH is of isotype IgG, e.g., of isotype subtype IgG1, IgG2a or b, IgG3 or IgG4. In a particular embodiment, the CH is of isotype subtype IgG1.

In some embodiments, the heavy chain of the anti-human TNFα antibody (HC) is at least 60% identical in sequence to SEQ ID NO: 5, e.g., at least 60%, 70%, or 80% identical to SEQ ID NO: 5. In some embodiments, the heavy chain of the anti-human TNFα antibody (HC) is at least 90% identical in sequence to SEQ ID NO: 5, e.g., at least 91%, 92%, 93%, 94%, 95%, 96%, 97%, 98%, or 99% identical to SEQ ID NO: 5. In a particular embodiment, the HC comprises or consists of the amino acid sequence of SEQ ID NO: 5.

In some embodiments, the light chain of the anti-human TNFα antibody comprises the light chain CDR1 (L-CDR1) amino acid sequence of SEQ ID NO: 13, the light chain CDR2 (L-CDR2) amino acid sequence of SEQ ID NO: 14, the light chain CDR3 (L-CDR3) amino acid sequence of SEQ ID NO: 15, or any combination thereof. In one embodiment, the light chain of the anti-human TNFα antibody comprises the L-CDR1, L-CDR2, and L-CDR3 amino acid sequences of SEQ ID NOs: 13-15. In some embodiments, the light chain of the anti-human TNFα antibody has a light chain variable domain (VL) that is at least 60% identical in sequence to SEQ ID NO: 9, e.g., at least 60%, 70%, or 80% identical to SEQ ID NO: 9. In some embodiments, the light chain of the anti-human TNFα antibody has a light chain variable domain (VL) that is at least 90% identical in sequence to SEQ ID NO: 9, e.g., at least 91%, 92%, 93%, 94%, 95%, 96%, 97%, 98%, or 99% identical to SEQ ID NO: 9. In a particular embodiment, the VL comprises or consists of the amino acid sequence of SEQ ID NO: 9.

In some embodiments, the light chain of the anti-human TNFα antibody (LC) is at least 60% identical in sequence to SEQ ID NO: 6, e.g., at least 60%, 70%, or 80% identical to SEQ ID NO: 6. In some embodiments, the light chain of the anti-human TNFα antibody (LC) is at least 90% identical in sequence to SEQ ID NO: 6, e.g., at least 91%, 92%, 93%, 94%, 95%, 96%, 97%, 98%, or 99% identical to SEQ ID NO: 6. In a particular embodiment, the VL comprises or consists of the amino acid sequence of SEQ ID NO: 6.

In some embodiments, a tri-specific binding molecule of the invention comprises aa anti-IL-17A/anti-IL-17F binding domain (e.g., a VHH domain) joined directly or via a linker to the heavy or light chain of the anti-TNFα binding domain (e.g., an antibody or an antigen-binding portion thereof). In one embodiment, the binding molecule comprises an anti-IL-17A/anti-IL-17F VHH domain joined via a linker to the light chain of an anti-TNFα antibody to form a fusion molecule. In some embodiments, the linker is at least 60% identical in sequence to SEQ ID NO: 16, e.g., at least 60%, 70%, or 80% identical to SEQ ID NO: 16. In some embodiments, the linker is at least 90% identical in sequence to SEQ ID NO: 16, e.g., at least 91%, 92%, 93%, 94%, 95%, 96%, 97%, 98%, or 99% identical to SEQ ID NO: 16. In a particular embodiment, the linker comprises or consists of the amino acid sequence of SEQ ID NO: 16. In some embodiments, the fusion molecule is at least 60% identical in sequence to SEQ ID NO: 7, e.g., at least 60%, 70%, or 80% identical to SEQ ID NO: 7. In some embodiments, the fusion molecule is at least 90% identical in sequence to SEQ ID NO: 7, e.g., at least 91%, 92%, 93%, 94%, 95%, 96%, 97%, 98%, or 99% identical to SEQ ID NO: 7. In a particular embodiment, the fusion molecule comprises or consists of the amino acid sequence of SEQ ID NO: 7.

In some embodiments, the tri-specific binding molecule comprises an anti-TNFα binding domain comprising any one of the above-described heavy chains and any one of the above-described light chains, or antigen-binding portions thereof. In certain embodiments, the tri-specific binding molecule further comprises any one of the above-described anti-IL-17A/anti-IL-17F binding domains. In a particular embodiment, the tri-specific binding molecule comprises any one of the above-described fusion molecules in combination with any of the above-described anti-TNFα binding domain heavy chains.

The class of a tri-specific binding molecule obtained by the methods described herein may be switched with another class or subclass. In one aspect of the invention, a nucleic acid molecule encoding VL or VH is isolated using methods well-known in the art such that it does not include nucleic acid sequences encoding CL or CH. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH chain, as described above. For example, a binding molecule that was originally IgM may be class switched to IgG. Further, the class switching may be used to convert one IgG subclass to another, e.g., from IgG1 to IgG2. An exemplary method for producing a binding molecule of the invention with a desired isotype comprises the steps of isolating a nucleic acid molecule encoding the heavy chain of a binding molecule and a nucleic acid molecule encoding the light chain of a binding molecule, obtaining the variable domain of the heavy chain, ligating the variable domain of the heavy chain with the constant domain of a heavy chain of the desired isotype, expressing the light chain and the ligated heavy chain in a cell, and collecting the binding molecule with the desired isotype.

The tri-specific binding molecule of the invention can be an IgG, an IgM, an IgE, an IgA, or an IgD molecule, but is typically of the IgG isotype, e.g. of IgG subclass IgG1, IgG2a or b, IgG3 or IgG4. In one embodiment, the binding molecule is an antibody of the IgG subclass IgG1.

In one embodiment, the tri-specific binding molecule comprises an Fc region with at least one mutation. A number of different Fc mutations are known, where these mutations provide altered effector function. For example, in many cases it will be desirable to reduce or eliminate effector function, e.g. where ligand/receptor interactions are undesired or in the case of antibody-drug conjugates. Fc region amino acid positions that may be advantageous to mutate in order to reduce effector function include one or more of positions 228, 233, 234 and 235, where amino acid positions are numbered according to the Kabat numbering scheme. In some embodiments, the tri-specific binding molecule comprises an Fc region with one or more mutations that reduce ADCC or CDC in comparison to the same binding molecule without the mutation.

In certain embodiments, a tri-specific binding molecule of the invention may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another embodiment, a fusion antibody or immunoadhesin may be made that comprises all or a portion of a tri-specific binding molecule of the invention linked to another polypeptide. In certain embodiments, only the variable domains of the tri-specific binding molecule are linked to the polypeptide. In certain embodiments, a VH domain of a tri-specific binding molecule is linked to a first polypeptide, while a VL domain of the tri-specific binding molecule is linked to a second polypeptide that associates with the first polypeptide in a manner such that the VH and VL domains can interact with one another to form an antigen-binding site. In another preferred embodiment, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a multi-specific antibody.

To create a single chain antibody (scFv), the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH domains joined by the flexible linker. See, e.g., Bird et al., *Science* 242:423-426 (1988); Huston et al., *Proc. Natl. Acad. Sci. USA* 85:5879-5883 (1988); and McCafferty et al., *Nature* 348:552-554 (1990). The single chain antibody may be monovalent, if only a single VH and VL are used; bivalent, if two VH and VL are used; or polyvalent, if more than two VH and VL are used.

In other embodiments, other modified antibodies may be prepared using tri-specific binding molecule-encoding nucleic acid molecules. For instance, "kappa bodies" (Ill et al., *Protein Eng.* 10:949-57 (1997)), "minibodies" (Martin et al., *EMBO J.* 13:5303-9 (1994)), "diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

A tri-specific binding molecule of the invention can be derivatized or linked to another molecule (e.g., another peptide or protein). In general, binding molecules (e.g., antibodies or antigen-binding portions thereof) are derivatized such that IL-17A, IL-17F, and/or TNFα binding is not affected adversely by the derivatization or labeling. Accordingly, the binding molecules of the invention may include both intact and modified forms of the tri-specific binding molecules described herein. For example, a binding molecule of the invention can be functionally linked (by chemical coupling, genetic fusion, noncovalent association or otherwise) to one or more other molecular entities, such as another antibody, a detection agent, a pharmaceutical agent, and/or a protein or peptide that can mediate association of the binding molecule with another molecule (such as a streptavidin core region or a polyhistidine tag).

One type of derivatized binding molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

A tri-specific binding molecule of the invention can also be derivatized with a chemical group such as polyethylene glycol (PEG), a methyl or ethyl group, or a carbohydrate group. These groups may be useful to improve the biological characteristics of the binding molecule, e.g., to increase serum half-life.

A tri-specific binding molecule according to the present invention may also be labeled. As used herein, the terms "label" or "labeled" refers to incorporation of another molecule in the binding molecule. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the tri-specific binding molecules of the invention may be present in a neutral form (including zwitter ionic forms) or as a positively or negatively-charged species. In some embodiments, the antibodies may be complexed with a counterion to form a pharmaceutically acceptable salt.

The term "pharmaceutically acceptable salt" refers to a complex comprising one or more tri-specific binding molecules and one or more counterions, wherein the counterions are derived from pharmaceutically acceptable inorganic and organic acids and bases.

Pharmaceutically acceptable inorganic bases include metallic ions including, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic or manganous salts, potassium, rubidium, sodium, and zinc, e.g., in their usual valences.

Pharmaceutically acceptable acid addition salts of the tri-specific binding molecules of the present invention can be prepared from the following acids, including, without limitation, formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N, N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid) dihydrate, 4-(2-hydroxyethyl)-1-piperazinepropanesulfonic acid, N,N-bis(2-hydroxyethyl)glycine, N-(2-hydroxyethyl)piperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino)ethanesulfonic acid, 3-(cyclohexylamino)-2-hydroxy-1-propanesulfonic acid, 3-(cyclohexylamino)-1-propanesulfonic acid, N-(2-acetamido) iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

In some embodiments, bispecific antibody molecules of the present disclosure comprise an anti-TNFα antibody comprising two heavy chains and two light chains, or an antigen-binding portion thereof, and an anti-IL-17A/anti-IL-17F VHH connected (directly or through a linker) to the antibody. The anti-IL-17A/anti-IL-17F VHH may be connected by its N-terminus or C-terminus to the N-terminus or C-terminus of the heavy or light chain of the anti-TNFα antibody. In certain embodiments, the anti-IL-17A/anti-IL-17F VHH is connected to the N-terminus of the light chain of the anti-TNFα antibody. Any such fusion described herein may be made according to methods known in the art. See, e.g., Ahmad et al., *Clinical and Developmental Immunology* 2012, Article ID 980250 (2012). In certain embodiments, the anti-TNFα antibody is joined to the anti-IL-17A/anti-IL-17F VHH by a linker, more preferably by a peptide linker, and most preferably by a peptide linker that lacks a proteolytic cleavage site. In some embodiments, the amino acid residues of the linker are selected from G, A, S, P, E, T, D, and K. In some embodiments, the linker comprises or consists of the amino acid sequence of SEQ ID NO: 16.

Nucleic Acid Molecules and Vectors

The present invention also provides nucleic acid molecules and sequences encoding tri-specific binding molecules of the invention described herein. In some embodiments, different nucleic acid molecules encode the first domain and second domain amino acid sequences of the tri-specific binding molecule. Where the first domain and/or the second domain comprises a heavy chain and a light chain, in some embodiments, different nucleic acids encode the heavy chain and the light chain amino acid sequences. In other embodiments, the same nucleic acid molecule encodes the heavy chain and light chain amino acid sequences. In certain embodiments, a nucleic acid molecule may encode any combination of the amino acid sequences (e.g., heavy and light chain sequences) of the first and second domains. In a particular embodiment, a nucleic acid molecule may encode the amino acid sequence of the first binding domain and the light chain amino acid sequence of the second binding domain, optionally including any peptide linker sequence joining the two.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single and double stranded forms.

The invention also provides nucleotide sequences that are at least 70%, 75%, 80%, 85%, 90%, 95%, 97%, 98% or 99% identical to one or more of the above-recited nucleotide sequences or to a nucleotide sequence encoding an amino acid sequence selected from the group consisting of SEQ ID NOs: 1-16. In certain embodiments, the nucleotide sequences are at least 90%, 91%, 92%, 93%, 94%, 95%, 96%, 97%, 98%, or 99% identical to a nucleotide sequence encoding an amino acid sequence selected from the group consisting of SEQ ID NOs: 4-9. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In one aspect, the invention provides a nucleic acid molecule comprising a nucleotide sequence that encodes an amino acid sequence selected from SEQ ID NOs: 1-16. The nucleic acid molecule may also comprise any combination of said nucleotide sequences. In one embodiment, the nucleic acid molecule comprises a nucleotide sequence that encodes SEQ ID NO: 4. In another embodiment, the nucleic acid molecule comprises a nucleotide sequence that encodes SEQ ID NOs: 4 and 6. In another embodiment, the nucleic acid molecule comprises a nucleotide sequence that encodes SEQ ID NOs: 4, 6, and 16. In another embodiment, the nucleic acid molecule comprises a nucleotide sequence that encodes SEQ ID NO: 7. In another embodiment, the nucleic acid molecule comprises a nucleotide sequence that encodes SEQ ID NO: 5.

In any of the above embodiments, the nucleic acid molecules may be isolated.

In a further aspect, the present invention provides a vector suitable for expressing any of the nucleotide sequences described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The invention provides vectors comprising nucleic acid molecules that encode any of the amino acid sequences of tri-specific binding molecules or portions thereof (e.g., heavy and/or light chain sequences of the first and/or second binding domains) as described herein. The invention further provides vectors comprising nucleic acid molecules encoding fusion proteins, modified antibodies, antibody fragments, and probes thereof.

A nucleic acid molecule of the invention can be isolated from any source that produces a tri-specific binding molecule or a portion thereof. In certain embodiments, a nucleic acid molecule of the invention can be synthesized rather than isolated.

In some embodiments, a nucleic acid molecule of the invention can comprise a nucleotide sequence encoding a VH domain from the first or second domain of a tri-specific binding molecule of the invention joined in-frame to a nucleotide sequence encoding a heavy chain constant domain from any source. Similarly, a nucleic acid molecule of the invention can comprise a nucleotide sequence encoding a VL domain from the first or second domain of a tri-specific binding molecule of the invention joined in-frame to a nucleotide sequence encoding a light chain constant domain from any source.

In a further aspect of the invention, nucleic acid molecules encoding the variable domain of the heavy (VH) and/or light (VL) chains of the first or second binding domain may be "converted" to full-length antibody genes. In one embodiment, nucleic acid molecules encoding the VH or VL domains are converted to full-length antibody genes by insertion into an expression vector already encoding heavy chain constant (CH) or light chain constant (CL) domains, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domains to a nucleic acid molecule encoding a CH and/or CL domain using standard molecular biological techniques. Nucleic acid molecules encoding the full-length heavy and/or light chains may then be expressed from a cell into which they have been introduced.

The nucleic acid molecules may be used to recombinantly express large quantities of tri-specific binding molecules. The nucleic acid molecules also may be used to produce human antibodies, humanized antibodies, chimeric antibodies, bispecific antibodies, single chain antibodies, immunoadhesins, diabodies, mutated antibodies and antibody derivatives, as described herein.

In another embodiment, a nucleic acid molecule of the invention is used as a probe or PCR primer for a specific amino acid sequence. For instance, the nucleic acid can be used as a probe in diagnostic methods or as a PCR primer to amplify regions of DNA that could be used, e.g., to isolate additional nucleic acid molecules encoding portions (e.g., variable domains) of tri-specific binding molecules. In some embodiments, the nucleic acid molecules are oligonucleotides. In some embodiments, the oligonucleotides are from highly variable domains of the tri-specific binding molecule. In some embodiments, the oligonucleotides encode all or a part of one or more of the CDRs of the tri-specific binding molecule of the invention as described herein.

In another embodiment, the nucleic acid molecules and vectors may be used to make mutated tri-specific binding molecules. The antibodies may be mutated in the variable domains of the heavy and/or light chains of the first and/or second binding domain, e.g., to alter a binding property of the tri-specific binding molecule. For example, a mutation may be made in one or more of the CDR regions to increase or decrease the $K_D$ of the tri-specific binding molecule, to increase or decrease $k_{off}$, or to alter the binding specificity of the antibody, with regard to L-17A, IL-17F, and/or TNFα. In another embodiment, one or more mutations are made at an amino acid residue that is known to be changed compared to the germline in an antibody corresponding to the first or second binding domain of the tri-specific binding molecule of the invention. The mutations may be made in a CDR region or framework region of a variable domain, or in a constant domain. In a preferred embodiment, the mutations are made in a variable domain. In some embodiments, one or more mutations are made at an amino acid residue that is known to be changed compared to the germline in a CDR region or framework region of a variable domain of a tri-specific binding molecule of the invention.

In another embodiment, the framework region(s) are mutated so that the resulting framework region(s) have the amino acid sequence of the corresponding germline gene. A mutation may be made in a framework region or constant domain to increase the half-life of the tri-specific binding molecule. See, e.g., WO 00/09560. A mutation in a framework region or constant domain also can be made to alter the immunogenicity of the tri-specific binding molecule, and/or to provide a site for covalent or non-covalent binding to another molecule. According to the invention, a tri-specific binding molecule may have mutations in any one or more of the CDRs or framework regions of a variable domain or in a constant domain.

In some embodiments, the tri-specific binding molecules of the invention are expressed by inserting DNAs encoding partial or full-length sequences of the first and second binding domains (e.g., heavy and light chain sequences where the binding domain comprises a heavy and light chain sequence), obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The DNAs may be ligated into a vector such that transcriptional and translational control sequences within the vector serve their intended function of regulating the transcription and translation of the DNAs. The expression vector and expression control sequences may be chosen to be compatible with the expression host cell used. DNAs encoding partial or full-length sequences of the first and second binding domains (e.g., heavy and light chain sequences where the binding domain comprises a heavy and light chain sequence) can be inserted into separate vectors can be inserted into separate vectors. In one embodiment, any combination of the above DNAs is inserted into the same expression vector. The DNAs may be inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can easily be inserted and expressed, as described above. The HC- and LC-encoding genes in such vectors may contain intron sequences that will result in enhanced overall antibody protein yields by stabilizing the related mRNA. The intron sequences are flanked by splice donor and splice acceptor sites, which determine where RNA splicing will occur. Location of intron sequences can be either in variable or constant regions of the antibody chains, or in both variable and constant regions when multiple introns are used. Polyadenylation and transcription termination may occur at native chromosomal sites downstream of the coding regions. The recombinant expression vector also can encode a signal peptide that facilitates secretion of an antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing binding molecules such as antibodies in plants, including a description of promoters and vectors, as well as transformation of plants, are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

The term "expression control sequence" as used herein means polynucleotide sequences that are necessary to affect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Host Cells and Methods of Tri-Specific Binding Molecule Production

An additional aspect of the invention relates to methods for producing the tri-specific binding molecules of the invention. One embodiment of this aspect of the invention relates to a method for producing a tri-specific binding molecule as defined herein, comprising providing a recombinant host cell capable of expressing the tri-specific binding molecule, cultivating said host cell under conditions suitable for expression of the tri-specific binding molecule, and isolating the resulting tri-specific binding molecule. Tri-specific binding molecules produced by such expression in such recombinant host cells are referred to herein as "recombinant tri-specific binding molecules." Where the tri-specific binding molecules are antibodies, they are referred to as "recombinant antibodies." The invention also provides progeny cells of such host cells, and tri-specific binding molecules produced by same.

The term "recombinant host cell" (or simply "host cell"), as used herein, means a cell into which a recombinant expression vector has been introduced. The invention provides host cells that may comprise, e.g., a vector according to the invention described above. The invention also provides host cells that comprise, e.g., a nucleotide sequence encoding the heavy chain or an antigen-binding portion thereof, a nucleotide sequence encoding the light chain or an antigen-binding portion thereof, or both, of the first binding domain and/or the second binding domain of a tri-specific binding molecule of the invention. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding tri-specific binding molecules of the invention and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740, 461, and 4,959,455. Methods of transforming plant cells are well known in the art, including, e.g., Agrobacterium-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding tri-specific binding molecules are introduced into mammalian host cells, the binding molecules are produced by culturing the host cells for a period of time sufficient to allow for expression of the binding molecule in the host cells or, more preferably, secretion of the binding molecule into the culture medium in which the host cells are grown. Tri-specific binding molecules can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of tri-specific binding molecules of the invention from production cell lines can be enhanced using a number of known techniques. For example, the glutamine synthetase gene expression system (the GS system) is a common approach for enhancing expression under certain conditions. The GS system is discussed in whole or part in connection with EP patents 0 216 846, 0 256 055, 0 323 997 and 0 338 841.

It is likely that tri-specific binding molecules expressed by different cell lines or in transgenic animals will have different glycosylation patterns from each other. However, all tri-specific binding molecules encoded by the nucleic acid molecules provided herein, or comprising the amino acid sequences provided herein, are part of the instant invention, regardless of the glycosylation state of the binding molecules, and more generally, regardless of the presence or absence of post-translational modification(s).

The tri-specific binding molecules can be prepared using a variety of methods. For example, the domains binding to IL-17A, IL-17F, and/or TNFα, or any combination thereof, can be prepared separately (e.g. using chemical protein synthesis, recombinant expression methods, hybridoma technology, etc.) and then chemically attached to each other, either directly or through a linker. Means of chemically conjugating molecules (e.g., antibodies or antigen-binding portions thereof) are well known to those of skill in the art. Polypeptides typically contain a variety of functional groups; e.g., carboxylic acid (COOH) or free amine (—NH2) groups, that are available for reaction with suitable functional groups on the corresponding polypeptide or on a linker. The antibodies can also be derivatized to expose or attach additional reactive functional groups, and can involve attachment of one or more linker molecules such as those available from Pierce Chemical Company, Rockford Ill. The linkers used in the tri-specific binding molecules of the invention may be any of a variety of suitable linkers known in the art.

In certain embodiments of the invention, the domains binding to IL-17A, IL-17F, and/or TNFα, or any combination thereof, are produced by expression of recombinant antibodies or antigen-binding portions in host cells. The sequences encoding any combination of the binding domains can be connected (directly or through a linker). The resulting nucleic acid molecules encoding the domains binding to IL-17A, IL-17F, and TNFα are inserted into expression vectors and introduced into host cells. The resulting tri-specific binding molecules are then expressed, isolated and purified from the expression system.

In certain embodiments of the invention, binding domains of the tri-specific binding molecule can be paired together with a novel linker molecule designed to protect against proteolytic degradation of the binding molecule. Such a linker typically lacks a proteolytic cleavage site.

Pharmaceutical Compositions

Another aspect of the invention is a pharmaceutical composition comprising as an active ingredient (or as the sole active ingredient) a tri-specific binding molecule of the invention. The pharmaceutical composition may comprise any tri-specific binding molecule as described herein. In some embodiments, the compositions are intended for amelioration, prevention, and/or treatment of a disorder that can be affected by activity of IL-17A, IL-17F, TNFα, and/or an autoimmune or inflammatory disease.

Generally, the tri-specific binding molecules of the invention are suitable to be administered as a formulation in association with one or more pharmaceutically acceptable excipient(s) e.g. as described below.

Pharmaceutical compositions of the invention may comprise at least one tri-specific binding molecule, and one or more additional binding molecules (e.g., antibodies) that target one or more relevant cell surface receptors, e.g., a cell surface receptor involved in an autoimmune or inflammatory response.

The term "excipient" is used herein to describe any ingredient other than the compound(s) of the invention. The choice of excipient will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in *Remington's Pharmaceutical Sciences*, 19th Edition (Mack Publishing Company, 1995). Pharmaceutical compositions are preferably manufactured under GMP (good manufacturing practices) conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the tri-specific binding molecule of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Intratumoral delivery, e.g. intratumoral injection, may also be advantageous. Regional perfusion is also contemplated. Preferred embodiments include the intravenous and the subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the tri-specific binding molecule in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin, and/or by using modified-release coatings (e.g., slow-release coatings).

The tri-specific binding molecules of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of a binding molecule of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the tri-specific binding molecule of the invention per actuation and the actuation volume may for example vary from 1 μL to 100 μL.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of a binding molecule of the invention. The overall daily dose will typically be administered in a single dose or, more usually, as divided doses throughout the day.

The tri-specific binding molecules of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

In one embodiment, the tri-specific binding molecules of the invention are formulated in a composition comprising histidine and acetate at a concentration of 1 to 100 mM, in a buffer with pH 5.0 to 6.5.

Therapeutic Uses of Tri-Specific Binding Molecules of the Invention

In one aspect, the tri-specific binding molecules of the invention are used in the treatment of a disorder that can be affected by activity of IL-17A, IL-17F, and/or TNFα. For example, a physician can treat an autoimmune or inflammatory disorder by administering a tri-specific binding molecule of the present invention, alone or in combination with other therapeutic agents (sequentially or concurrently). The tri-specific binding molecule modulates the activity of IL-17A, IL-17F, and/or TNFα, resulting in reduction of an autoimmune or inflammatory response. Disorders that can be treated by the tri-specific binding molecules and methods of the present invention may include any of the following: rheumatoid arthritis, osteoarthritis, juvenile chronic arthritis, septic arthritis, Lyme osteoarthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, plaque psoriasis, atopic dermatitis, scleroderma, reaction "graft versus host" organ transplant rejection, acute or chronic immune disease associated with organ transplantation, sarcoidosis, Kawasaki disease, Graves disease, nephrotic syndrome, chronic fatigue syndrome, Wegener's granulomatosis, Henoch-Schonlein purpura, microscopic renal vasculitis, chronic active hepatitis, uvenita, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, adult (acute) respiratory distress syndrome, alopecia, alopecia areata, seronegative arthropathy, arthropathy, Reiter's disease, psoriatic arthropathy associated with ulcerative colitis arthropathy, atopic allergy, autoimmune bullous diseases, pemphigus vulgaris, sheet-like pemphigus, pemphigoid disease, linear IgA, an autoimmune hemolytic anemia, Coombs-positive hemolytic anemia, acquired pernicious anemia, juvenile pernicious anemia, arthritis, primary sclerosing hepatitis A, cryptogenic autoimmune hepatitis, fibrosis lung disease, cryptogenic fibrosis alveolitis, post-inflammatory interstitial lung disease, interstitial pneumonitis, chronic eosinophilic pneumonia, post-infectious interstitial lung disease, gouty arthritis, autoimmune hepatitis, autoimmune hepatitis type I (classical autoimmune hepatitis or lupoid), autoimmune hepatitis type II osteoarthritis, primary sclerosing cholangitis, psoriasis type I, type II psoriasis, idiopathic leucopenia, autoimmune neutropenia, renal NOS-disease, glomerulonephritis, microscopic renal vasculitis, discoid lupus erythematosus, idiopathic or NOS-male infertility, autoimmunity to sperm, multiple sclerosis (all subtypes), sympathetic ophthalmia, pulmonary hypertension secondary to connective tissue disease, syndrome Goodpasture, pulmonary manifestations of polyarthritis nodosa, acute rheumatic fever, rheumatoid spondylitis, ankylosing spondylitis, Still's disease, systemic sclerosis, syndrome Shengrena, Sjögren's syndrome, Takayasu's arteritis, autoimmune thrombocytopenia, idiopathic thrombocytopenia, autoimmune thyroid disease, hyperthyroidism, goiter autoimmune hypothyroidism (Hashimoto's disease), autoimmune atrophic hypothyroidism, primary myxedema, phacogenic uveitis, primary vasculitis, vitiligo, acute liver disease, chronic liver disease, allergies, asthma, psychiatric disorders (including depression and schizophrenia), mediated type Th2 and Th1 type diseases, conjunctivitis, allergic contact dermatitis, allergic rhinitis, a deficiency of alpha-1-antitrypsin, amyotrophic lateral sclerosis, anemia, cystic fibrosis, associated with cytokine therapy disorders, demyelinating disease, dermatitis, iridocyclitis/uveitis/optic neuritis, damage in ischemia-reperfusion injury, ischemic stroke, juvenile rheumatoid arthritis, autoimmune enteropathy, autoimmune hearing loss, autoimmune lymphoproliferative syndrome, autoimmune myocarditis, autoimmune premature ovarian failure, and blepharitis. The tri-specific binding molecule may also treat any combination of the above disorders.

In certain embodiments, a tri-specific binding molecule of the invention is used to treat a disorder selected from (but not limited to) rheumatoid arthritis (RA), osteoarthritis, rheumatoid arthritis osteoporosis, inflammatory fibrosis (e.g., scleroderma, pulmonary fibrosis and cirrhosis), gingivitis, periodontosis or periodontal diseases, inflammatory bowel diseases (e.g., Crohn's disease, ulcerative colitis and inflammatory bowel disease), asthma (including allergic asthma), allergies, chronic obstructive pulmonary disease (COPD), multiple sclerosis, psoriasis, and cancer.

In a particular embodiment, a tri-specific binding molecule of the invention is used to treat rheumatoid arthritis, psoriasis, or psoriatic arthritis.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

"Therapeutically effective amount" refers to that amount of the therapeutic agent being administered which will relieve to some extent one or more of the symptoms of the disorder being treated.

The tri-specific binding molecules of the invention may be administered alone or in combination with one or more other drugs or antibodies (or as any combination thereof). The pharmaceutical compositions, methods and uses of the invention thus also encompass embodiments of combinations (co-administration) with other active agents, as detailed below.

As used herein, the terms "co-administration", "co-administered" and "in combination with," referring to the tri-specific binding molecules with one or more other therapeutic agents, is intended to mean, and does refer to and include the following:

simultaneous administration of such combination of tri-specific binding molecule of the invention and therapeutic agent(s) to a patient in need of treatment, when such components are formulated together into a single dosage form which releases said components at substantially the same time to said patient, substantially simultaneous administration of such combination of tri-specific binding molecule of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination of tri-specific binding molecule of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of tri-specific binding molecule of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The tri-specific binding molecules of the invention may be administered without additional therapeutic treatments, i.e., as a stand-alone therapy. Alternatively, treatment with the tri-specific binding molecules of the invention may include at least one additional therapeutic treatment (combination therapy). In some embodiments, the tri-specific binding molecule may be co-administered or formulated with another medication/drug for the treatment of an autoimmune or inflammatory disorder.

In some embodiments, a tri-specific binding molecule of the invention is administered in combination with an anti-inflammatory agent. Anti-inflammatory agents that may be administered with the tri-specific binding molecules of the invention include, but are not limited to, corticosteroids (e.g. betamethasone, budesonide, cortisone, dexamethasone, hydrocortisone, methylprednisolone, prednisolone, prednisone, and triamcinolone), nonsteroidal anti-inflammatory drugs (e.g., balsalazide, celecoxib, diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, olsalazine, oxaprozin, phenylbutazone, piroxicam, salsalate, sulindac, tenoxicam, tiaprofenic acid, and tolmetin), as well as acetaminophen, antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives (e.g. sulfasalazone and mesalamine), thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In some embodiments, a tri-specific binding molecule of the invention is administered in combination with an immunosuppressive agent such as, but not limited to, steroids, cyclosporine, cyclosporine analogs, cyclophosphamide methylprednisone, prednisone, azathioprine, FK-506, 15-deoxyspergualin, natalizumab, and other immunosuppressive agents that act by suppressing the function of responding T cells.

In some embodiments, a tri-specific binding molecule of the invention is administered in combination with an immunosuppressant such as, but not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, AVONEX™ (interferon-beta 1A), and RAPAMUNE™ (sirolimus). In one embodiment, immunosuppressants may be used to prevent rejection of organ or bone marrow transplantation.

In some embodiments, a tri-specific binding molecule of the invention is administered in combination with a TNF antagonist. TNF antagonists that may be administered with the binding molecules of the invention include, but are not limited to, infliximab (REMICADE™), adalimumab (HUMIRA™), certolizumab pegol (CIMZIA™), golimumab (SIMPONI™), etanercept (ENBREL™), xanthine derivatives (e.g. pentoxifyline) and bupropion (WELLBURTIN™, ZYBAN™). In certain embodiments, the TNF antagonist is a TNFα antagonist.

In some embodiments, a tri-specific binding molecule of the invention is administered in combination with an antagonist from the list including, but not limited to, IL-6R antagonists (e.g., tocilizumab and serulumab), IL-6 antagonists, IL-1a or IL-1b antagonists, IL-23 antagonists, IL-22 antagonists, and GM-CSF antagonists.

In some embodiments, a tri-specific binding molecule of the invention is administered in combination with an IL-17A and/or IL-17F antagonist. In certain embodiments, said antagonist is an anti-IL-17A and/or anti-IL-17F antibody or an antigen-binding portion thereof.

Pharmaceutical articles comprising a tri-specific binding molecule of the invention and at least one other agent (e.g., an immunosuppressive or anti-inflammatory agent) may be used as a combination treatment for simultaneous, separate or successive administration in treatment of an autoimmune or inflammatory disorder.

It is understood that the tri-specific binding molecules of the invention may be used in a method of treatment as described above, may be for use in a treatment as described above, and/or may be for use in the manufacture of a medicament for a treatment as described above.

Dose and Route of Administration

The tri-specific binding molecules of the invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the tri-specific binding molecules are being administered as a stand-alone treatment or in combination with one or more additional anti-autoimmune or anti-inflammatory treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of this invention may be based on a variety of factors, including the type of disease, the age, weight, sex, medical condition of the patient, the severity of the condition, the route of administration, and the particular tri-specific binding molecule employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

Examples of suitable routes of administration are provided above.

It is contemplated that a suitable dose of a tri-specific binding molecule of the invention will be in the range of 0.1-100 mg/kg, such as about 0.5-50 mg/kg, e.g., about 1-20 mg/kg. The tri-specific binding molecule may for example be administered in a dosage of at least 0.25 mg/kg, e.g., at least 0.5 mg/kg, such as at least 1 mg/kg, e.g., at least 1.5 mg/kg, such as at least 2 mg/kg, e.g., at least 3 mg/kg, such as at least 4 mg/kg, e.g., at least 5 mg/kg; and e.g., up to at most 50 mg/kg, such as up to at the most 30 mg/kg, e.g., up to at the most 20 mg/kg, such as up to at the most 15 mg/kg. Administration will normally be repeated at suitable intervals, e.g., once every week, once every two weeks, once every three weeks, or once every four weeks, and for as long as deemed appropriate by the responsible doctor, who may optionally increase or decrease the dosage as necessary.

An effective amount for autoimmune or inflammatory disorder therapy may be measured by its ability to stabilize disease progression and/or ameliorate symptoms in a patient, and preferably to reverse disease progression. The ability of a tri-specific binding molecule of the invention to inhibit an autoimmune or inflammatory disorder may be evaluated by in vitro assays, e.g., as described in the examples, as well as in suitable animal models that are predictive of the efficacy in such disorders. Suitable dosage regimens will be selected in order to provide an optimum therapeutic response in each particular situation, for example, administered as a single bolus or as a continuous infusion, and with possible adjustment of the dosage as indicated by the exigencies of each case.

Diagnostic Uses and Compositions

The tri-specific binding molecules of the present invention also are useful in diagnostic processes (e.g., in vitro, ex vivo). For example, the tri-specific binding molecules can be used to detect and/or measure the level of IL-17A, IL-17F, and/or TNFα in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassay, and immunohistology. The invention further encompasses kits (e.g., diagnostic kits) comprising the tri-specific binding molecules described herein.

In order that this invention may be better understood, the following examples are set forth. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

EXAMPLES

Example 1: Creation and Optimization of Tri-Specific Anti-IL-17A/Anti-IL-17F/Anti-TNFα Antibodies Trispecific anti-IL-17A/anti-IL-17F/anti-TNFα antibodies were created and optimized as shown in FIG. 1.

Example 2: Production of Recombinant Antigens and Antibodies in Suspension Culture of Mammalian Cells Antibodies and antigens were produced in CHO-K1 cells constitutively expressing EBNA 1 (Epstein-Barr virus nuclear antigen 1), according to published protocols (Longo et al., *Methods Enzymol* 529:227-240 (2013)). The cells were cultivated in suspension on orbital shakers using a serum-free media produced by Life Technologies Corporation, according to the manufacturer's instructions. For transient expression, cells were transfected at a concentration of 2×10E6/ml with a linear polyethyleneimine (PEI MAX, Polysciences). The DNA/PEI ratio was 1:3. 5-7 Days after transfection, the culture medium was centrifuged at 2000 g for 20 minutes and filtered through a 0.22 μm filter. The target proteins were extracted from the culture fluid by affinity chromatography.

Recombinant protein IL-17A containing six amino acids at the C-terminus of the protein and FLAG-peptide (FIG. 2) was extracted and purified from the culture fluid using Profinity IMAC Ni-charged resin (Bio-Rad Company). Prior to purification, $NiCl_2$ was added to the culture fluid to a concentration of 1 mM. 5 ml of Profinity IMAC Ni-charged resin were then added to the culture fluid and stirred on a shaker for 1 h at room temperature. The sorbent (5 ml) was transferred to a Thermo Scientific polypropylene column and washed with 5 column volumes of PBS to remove non-specific binding components. Bound antigen was eluted using 0.3 M imidazole, pH 8, 150 mm NaCl. The protein then was transferred to PBS (pH 7.4) by dialysis using SnakeSkin Dialysis Tubing technology, filtered (0.22 μm), transferred to tubes, and stored at −70° C. Purity of the resulting protein solution was assessed by SDS-gel electrophoresis (FIG. 3).

Figure 4:
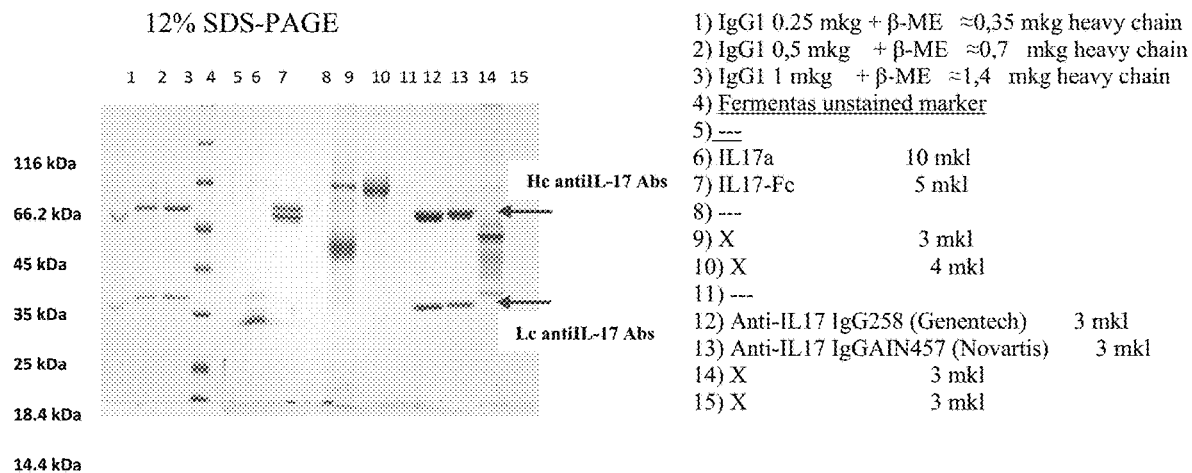
FIG. 4 is a gel showing purified control anti-IL-17A antibodies.
Figure 5:
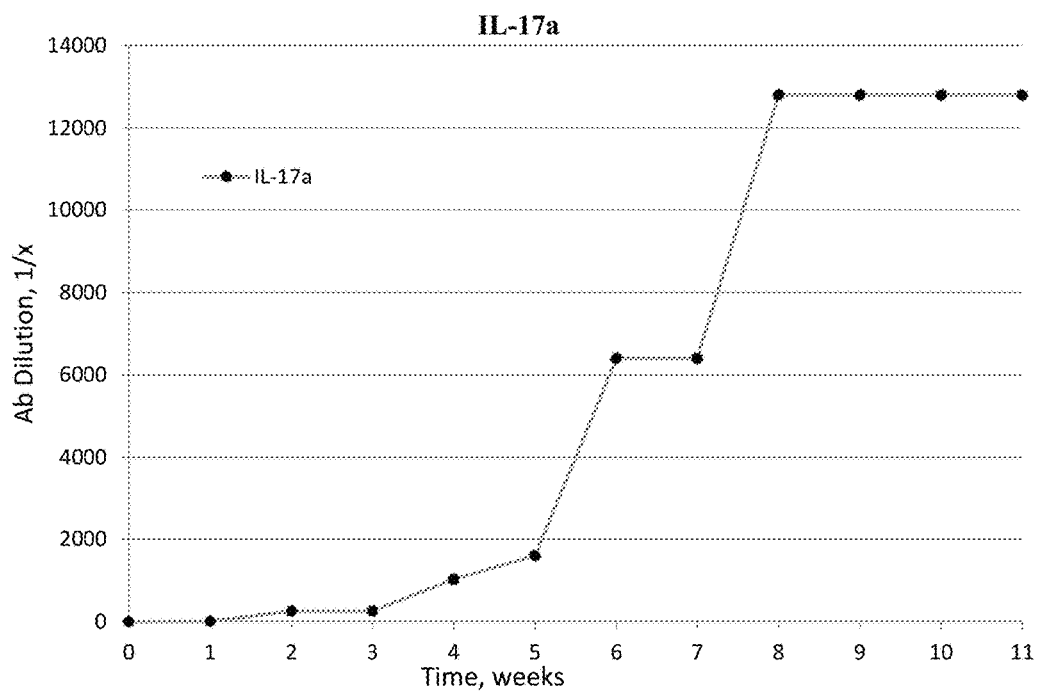
FIG. 5 is a graph showing a titer of anti-human IL-17A antibodies produced by immunization of *Lama glama*.

Test and control IgG1 antibodies were purified on a HiTrap Protein FF 1 ml column (GE Healthcare) according to the procedure described above for the IL-17A-Fc antigen. Purity of the resulting protein solution was assessed by SDS-gel electrophoresis (FIG. 4).

According to electrophoresis purity data under denaturing conditions, the recombinant antigen products and IL-17A-H6F and IL-17A-Fc are suitable for immunization and further research. Furthermore, control preparation AIN457 (Novartis; reproduced (U.S. Pat. No. 7,807,155 B2)) of satisfactory purity can be used in studies.

Example 3: Immunization of Llamas with Human Il-17a and Creation of Llama Fab Phase Antibody Library Llamas (*Lama glama*) were immunized 5 times successively by subcutaneous injection of the antigenic material mixed with an equal volume of complete (during the first injection) or incomplete (for the remaining injections) Freund's adjuvant. A mixture of the recombinant protein was used as the antigen (0.2 mg of each protein per 1 injection), one of which was human IL-17A-H6F (Example 2). A second injection (the immunization step) was performed 3 weeks after the first, and then at intervals of two weeks, the immunization was carried out three more times. Blood samples (50 ml) were taken 5 days after each injection, starting with the third.

The collected llama blood after immunization was diluted 2 times with PBS solution containing 1 mM EDTA. 35 ml of diluted blood was layered on the medium solution Histopaque®-1077 (Sigma) at a density of 1.077 g/ml, volume of 15 ml, and then centrifuged for 20 min at 800 g. Mononuclear cells (lymphocytes and monocytes) were selected from the interphase zone of the plasma/Histopaque medium and then washed with PBS solution containing 1 mM EDTA.

The resulting serum immunoglobulin titer against IL-17A, certified according to the standard protocol, was not less than 1/10000, which is satisfactory for the construction of antibody libraries (5).

Mononuclear cell total RNA was extracted using the llama RNeasy Mini Kit according to the suggested protocol (QIAGEN). RNA concentration was determined by Nanovue (GE Healthcare) and the quality of extracted RNA was checked by electrophoresis on a 1.5% agarose gel.

The reverse transcription reaction was performed using a MMLV RT kit (Evrogen) according to the recommended protocol using reverse transcriptase and random-MMuLV hexameric oligonucleotides as primers.

Figure 6:
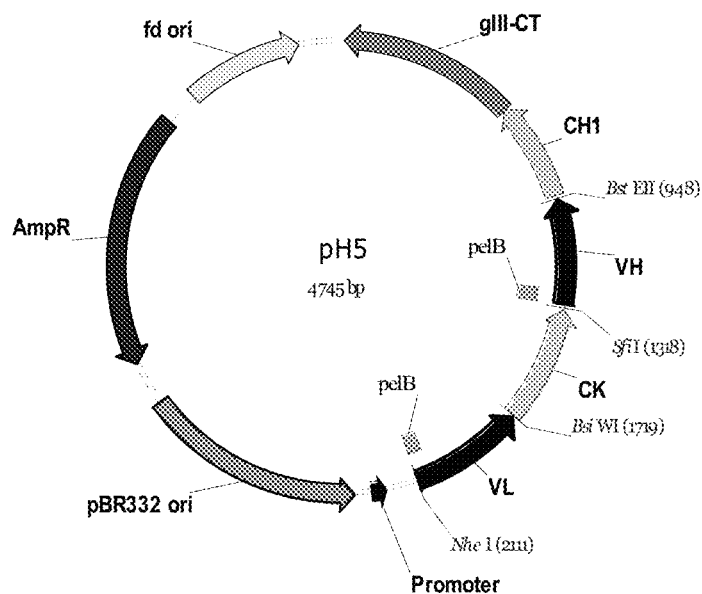
FIG. 6 is a map showing the pH5 plasmid for phage display of antibody Fab fragments.

Reverse transcription products were used as a template in a two-stage PCR to produce variable domain genes flanked by restriction sites using a set of oligonucleotides and published protocols (de Haard et al., *J Biol Chem* 274(26): 18218-30 (1999); De Genst et al., *Dev Comp Immunol* 30(1-2):187-98 (2006)). Then, the compound of the genes of the variable light and heavy chain domains of one fragment was carried out by sequential restriction, ligation, and amplification. The genes of heavy chains were combined with kappa genes and separately with lambda genes of light chains. Thus, the estimated number of molecules of the matrix in all reactions was not less than $10^{11}$. The resulting DNA product VL-CK-VH was treated with restriction enzymes NheI/Eco91I and ligated into the original phagemid pH5. FIG. 6 shows the resulting structure of the phasmids. The ligation products were transformed into electrocompetent SS320 cells obtained according to known protocols (Bond et al., *J Mol Biol* 332(3):643-55 (2003)). The repertoire of kappa derivatives of the Fab library was 5.1*10E8 and of lambda derivatives of the Fab library was −3.7*10E8, respectively.

Example 4: Selection of Fab Libraries of Phage Antibodies

Specific anti-IL-17A phage Fabs were isolated from the Fab-display library on recombinant human IL-17A (R&D Systems) by performing a series of selection cycles, as previously described (Marks et al., J Mol Biol 222(3):581-597 (1991); de Haard et al., *J Biol Chem* 274(26):18218-30 (1999)). To carry out the selection by panning, human IL-17A in 50 mM carbonate buffer (pH 9.5) was adsorbed overnight at 4° C. on the surface of sorbent tubes High Sorb (Nunc). The tubes were washed with PBS (pH 7.4), then blocked with PBS solution (pH 7.4)—skim milk (0.5% wt./Vol.) for 1 h. Next, 2.4 ml of phage solution in PBS (pH 7.4)—skim milk (0.5% wt./Vol.) at a concentration of 1012 phage particles in 1 ml were added to a test tube with antigen and incubated for 1 hour with stirring. Nonbinding phage was removed during a series of wash cycles using PBS solution (pH 7.4)—Tween 20 (0.1% vol./vol.). The number of washes was increased from the first round to the third round to 20-30-40 times, respectively. The remaining bound phage particles were eluted with 100 ml of a Gly-HCl (pH 2.5) solution for 15 min with stirring, and then neutralized with 1 M Tris-HCl (pH 7.6). Bacteria strain *E. coli* TG1 was infected with obtained phages, then phages were isolated and used in the next cycle of selection.

Figure 7:
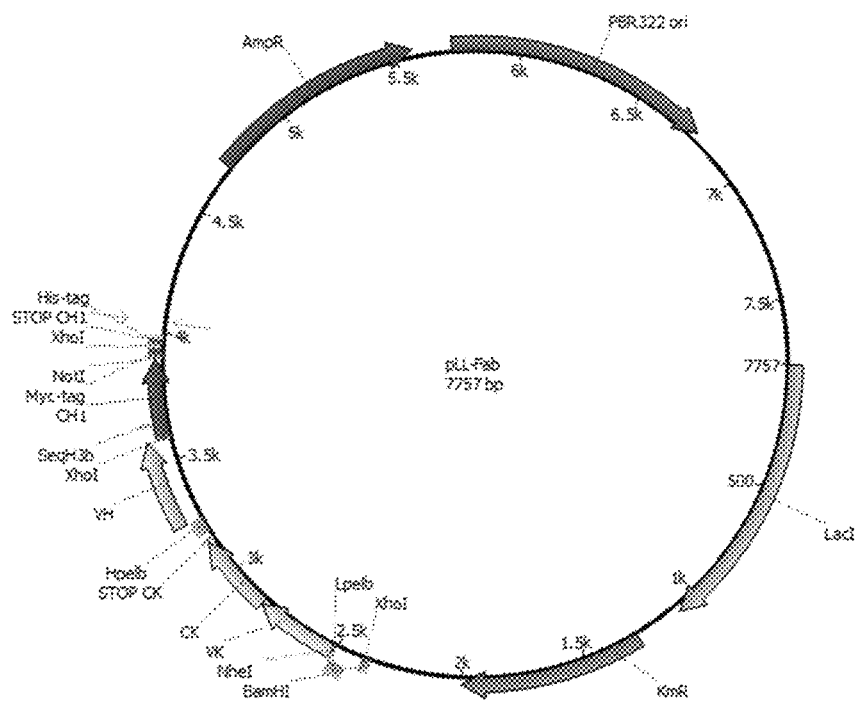
FIG. 7 is a map showing the pLL-Fab plasmid for secretory expression of antibody Fab fragments in *E. coli*.
Figure 8:
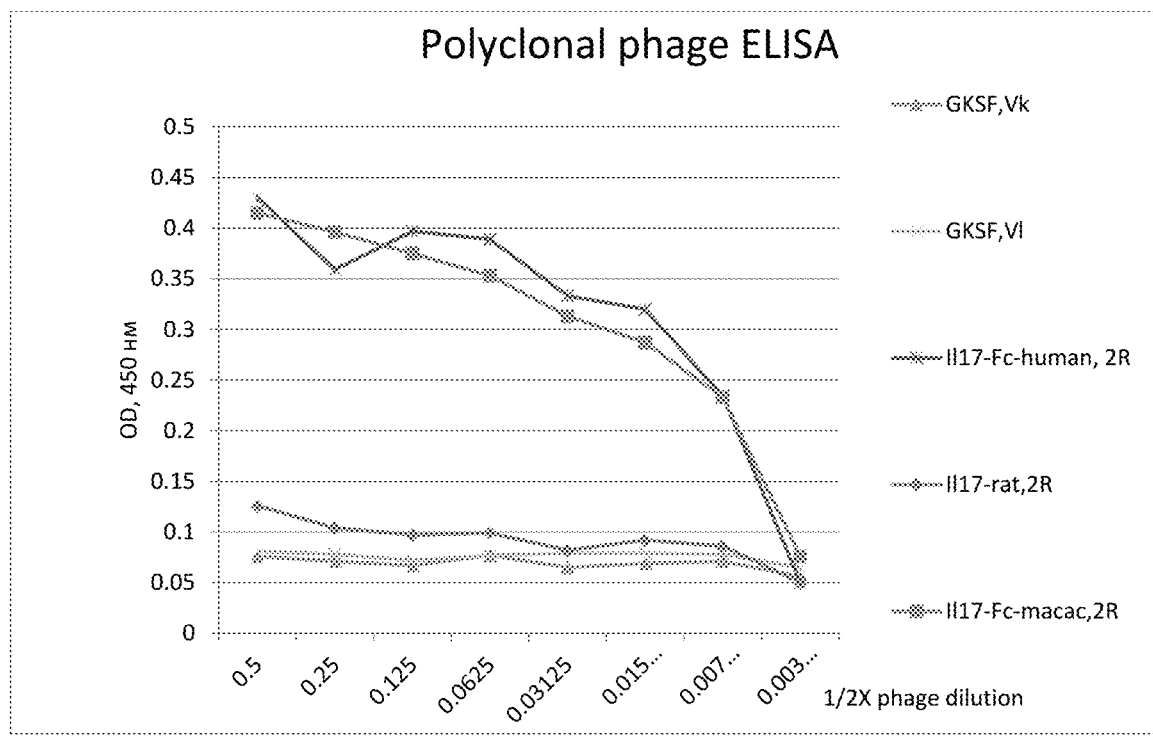
FIG. 8 is a graph showing the binding of polyclonal phage with specific and nonspecific antigens after selection of anti-IL17-A fragments from an immune phage library.

After the second and third round of selection on IL-17A, EIA analysis of the polyclonal phage product showed a significant enrichment (FIG. 8). The resulting pool of clones enriched by human Fab specific to anti-IL-17A was recloned to the expression plasmid pLL (FIG. 7), containing myctag and His6 tag at the C-terminus of the heavy chain CH1 gene.

Example 5: Analysis of the Specific Binding of Fab to Human IL-17a

EIA (ELISA) was used to measure binding of selected Fab fragments with human IL-17A. As a positive control, a Fab antibody AIN457 with a published sequence (Novartis)

was used. For the specific binding assay, wells on ELISA plates (Nunc Immuno Maxisorp) were coated with 50 µl IL-17A (0.5 µg/ml in 1× coating carbonate buffer), then sealed and incubated overnight at 4° C. All subsequent steps were performed by standard EIA protocol using an automated high-performance platform based on GenetixQ-pix2xt (Molecular Device) robotic systems and Tecan Freedom EVO 200 (Tecan). To block non-specific binding, blocking buffer (BB) was added (200 µl 0.5% skim milk in PBS). Plates were incubated on a shaker for one hour at room temperature. After washes with PBS-Tween, 50 µl per well of the test cell supernatant containing the analyzed Fab was added, mixed with an equal volume of blocking buffer. Plates were again incubated with shaking for one hour at room temperature, then each well of the plates was washed five times with PBS-Tween buffer. After washing, 50 µl/well of human anti-Fab HRP-conjugated secondary antibody (Pierce-Thermo Scientific) was added in a ratio of 1:5000 in PBS-Tween. Plates were shaken on a rotary shaker (50 min, room temperature) and washed five times with PBS-Tween buffer, as described above. The colorimetric signal was developed by adding TMB (100 µl/well) until saturation (on average 3-5 minutes), then further development was stopped by adding the terminating solution (100 µl/well, 10% sulfuric acid). The color signal was measured at a wavelength of 450 nm, using a suitable plate reader (Tecan-Sunrise; Tecan). The extent of antibody binding was proportional to color signal production. Clones in which the signal exceeded background color more than 5 times were tested in a competitive EIA analysis to detect antagonistic Fabs that block the interaction between IL-17A ligand and receptor.

Example 6: Competitive EIA Analysis of Blocking of the Interaction Between IL-17A Ligand and IL-17R Receptor Competitive ELISA was used to analyze the antagonistic ability of previously selected anti-human IL-17A Fabs. As a positive control, we used antagonist Fab antibodies AIN457 (Novartis). 50 µl of receptor IL-17ARA-Fc (R&D Systems) was immobilized to wells of ELISA plates (Nunc Immuno Maxisorp), at a concentration of 1 mg/ml in 1× coating carbonate buffer, and incubated overnight at 4° C. All subsequent steps were performed by standard EIA protocol using an automated high-performance platform based on GenetixQ-pix2xt (Molecular Device) robotic systems and Tecan Freedom EVO 200 (Tecan). To block non-specific binding, blocking buffer (BB) was added (200 µl 0.5% of skimmed milk in PBS). Plates were incubated on a shaker for one hour at room temperature.

Simultaneously, 50 µl of the test cell supernatant containing the analyzed Fab was mixed in a 96-well plate with 50 µl of IL-17A-His6-Flag at a concentration of 0.4 µg/ml in 1% milk PBS-Tween. It was then incubated for 1 hour at 37° C. with stirring on a shaker at 500 rot/min.

After washing blocking buffer from the plates containing IL-17ARA-Fc receptor, the reaction mixture described above was transferred at 90 µl per well. The plates were incubated again with shaking for 45 minutes at room temperature, then each well of the plates was washed five times with PBS-Tween buffer. 50 µl/well of mouse anti-FLAG M2 antibody (Sigma) was added at a concentration of 1 µg/ml. The plates were incubated for 45 min at room temperature, then each well of the plates was washed 5 times with PBS-Tween buffer. 50 µl/well of anti-mouse-IgG HRP-conjugated secondary antibody (Pierce-Thermo Scientific) diluted at the rate of 1:5000 in PBS-Tween was added. Plates were shaken on a rotary shaker for 45 minutes at room temperature and washed 5 times with PBS-Tween buffer, as described above. The colorimetric signal was developed by adding TMB (100 µl/well) until saturation (on average 3-5 minutes), then further development was stopped by adding a terminating solution (10% sulfuric acid, 100 µl/well). The color signal was measured at a wavelength of 450 nm, using a suitable plate reader (Tecan-Sunrise; Tecan). The extent of antibody binding was proportional to the color signal production.

Clones that showed blockage at the level of the control Fab antibody AIN457 were noted as positive and used for further analysis. Genes of the variable domains of positive clones were sequenced according to standard protocols using the Applied Biosystems 3130 Genetic Analyzer (Applied Biosystems) and analyzed. Clones containing VHH variable domains were selected for further research. It was also found that one clone, 3VHHFab, appeared in combination with twenty-three different light chain domain sequences, which may indicate its relative structural tolerance and may suggest that that VHH domain, but not the light chain, contributes to interaction with IL-17A.

Example 7: Comparative Screening of Anti-IL-17A VHHFab Candidates By Kinetic Dissociation Constant $k_{off}$ ($k_{dis}$)

Comparative screening of $k_{off}$ for anti-IL-17A Fab candidates was performed using the device Octet Red 96 (Pall-ForteBio). Anti FABCH1 biosensors were rehydrated for 30 minutes in running buffer containing 10 mM PBS, pH 7.2-7.4, 0.1% Tween-20, and 0.1% BSA. E. coli 10×-work buffer was added to the test samples to a final concentration of 1×. Anti FABCH1 biosensors were then immersed in the samples of candidate Fab fragments and E. coli for 4 hours at 12° C. Sensors with immobilized Fab fragments on the surface were transferred into wells with a running buffer, where baseline was specified (60 sec.). Then sensors were transferred into wells with a solution of analyte (IL-17A, 30 µg/ml) for association of the antigen-antibody complex (300 sec.). Sensors were then returned to wells containing running buffer for a subsequent dissociation step (300 sec.). After each experiment, used sensors were regenerated for use in the following experiment by placing them in a three-fold buffer for regeneration (Gly-HCl, pH 1.7). Analysis of the curves was performed using the Octet Data Analysis software (version 7.0) according to standard procedure using the interaction model 1:1.

The results of $k_{off}$-screening of anti-IL-17A Fab candidates are presented in Table 1. All of the unique VHHFabs demonstrated specific high affinity binding with human IL-17A, while 3VHHFab demonstrated very fast $k_{on}$ and very slow $k_{dis}$ (1/sec.), extending beyond the sensitivity of the instrument.

TABLE 1

VHHFab Affinity for Human IL-17A and Specificity for Human IL-17F.

| | $K_D$ (M) | $k_{on}$ (l/Msec) | $k_{dis}$ (1/sec) | Binding to human IL-17F* |
|---|---|---|---|---|
| 1VHH | 2.485E−08 | 2.498E−04 | 6.206E−04 | − |
| 2VHH | 1.352E−08 | 1.628E−05 | 2.201E−03 | − |
| 3VHH VK4B11 | − | − | <2.272E−06 | +++ |

− no signal in the EIA with excess of not more than 50% above the background,
+++ strong signal exceeding more than 10 times over the background.

Thus, based on the analysis data, the VHH monodomain of 3VHHVK4B11 showed maximum binding affinity in comparison to the other two candidates.

Example 8: Specific Binding of VHHFab to Human IL-17F

ELISA assays were performed on the three aforementioned VHHFabs according to the standard ELISA protocol described in Example 5, but for human IL-17F (R&D Systems). Fab antibody AIN457 (published sequence; Novartis) was used as a positive control. The results of the qualitative analysis of the interaction of the three VHHFab candidates are presented in Table 1. The VHH monodomain hereinafter designated as VHH17 (SEQ ID NO: 1; FIG. 9,) with the mutations described below, was selected for further work on the basis of affinity and cross reactivity tests for 3VHHVK4B11 Fab.

Example 9: Scanning Mutagenesis of CDRs of the Anti-IL-17A VHH17 Domain

Mutations to individual positions of the VHH17 domain CDRs were inserted by means of the NNK randomization technique using Q5® Site-Directed Mutagenesis Kit (NEB) in accordance with the manufacturer's protocol. Plasmid pET22b-VHH17 was used as a matrix. PCR products were fractionated on low-melting agarose gels and purified on appropriate columns. After ligation, DNA was transformed into *E. coli* expression strain BL21(DE3). The individual clones obtained by expression in 96-well plates, as described above. Supernatants containing mutant VHH17 were analyzed by ELISA under the conditions described above and using the high-performance Genetix Q-pix2xt and Tecan Freedom EVO200 systems. The concentration of immobilized IL-17A was 0.2 μg/ml. Bound VHH17 monodomains were stained with 1:5000 diluted mouse anti-myc-tag 9E10 and anti-mouse IgG (HRP) conjugate (Pierce) and TMB+ $H_2O_2/H_2SO_4$ dye; absorption was measured at a wavelength of 450 nm.

The results obtained by scanning mutagenesis are presented in Table 2. The table shows CDR substitutions that correspond to ≤30% reduction of mutant VHH17/human Il-17A binding signal when compared to the wild type sequence. In one aspect, the invention provides tri-specific binding molecules comprising these mutations and any combinations thereof.

TABLE 2

VHH17 scanning mutagenesis

| Mutation position | Positive amino acids in mutants |
|---|---|
| HCDR3 | |
| V94 | S, T, A, K, D, G |
| R95 | K |
| R96 | Y, H, W, K, D, G |
| R97 | A, L, M, S, H, V |
| F98 | — |
| D99 | E, G, A, R, V, K, Q |
| G100 | N, S |
| T100a | G, P, V, R, S, N, K |
| S100b | V, M, T, L, T, A, H, G, I , C |
| Y100c | W, S |
| Y100d | R, L, W, K, A, G, Q, I, V |
| T100e | A, L, S |
| G100f | A, L, T, P, N, Q, F, I, D |
| D107 | — |
| HCDR2 | |

TABLE 2-continued

VHH17 scanning mutagenesis

| Mutation position | Positive amino acids in mutants |
|---|---|
| A50 | G, L |
| S52 | — |
| P52a | A |
| S53 | — |
| G54 | — |
| G55 | S, R, P, D, I, T, E, K, A, L |
| D56 | — |
| R57 | — |
| I58 | — |
| HCDR1 | |
| S32 | N, K, R, E, W, M, Q, D, F, V, L, A |
| P33 | S |
| M34 | I |
| G35 | L, A, I, S, R, V, N, Q, M |

This screening identified amino acid positions in the CDRs of VHH17 that are tolerant of amino acid substitutions. It has been demonstrated that the present panel of amino acid substitutions does not significantly change the binding affinity of VHH17 affinity for human IL-17A. Thus, this substitution panel can be used to improve various properties of the candidate.

Example 10: Engineering and Generating Anti-IL-17A/Anti-IL-17F and Anti-TNFα Tri-Specific Antibodies: VHH-IgG1 (LALA)

The genes for the heavy and light chain variable domains of an antibody against human TNFα (RU 2303604) were synthesized in the original codon composition and cloned into pEE-Hc (IgG1) and pEE-Lc plasmids for the heavy and light chain, respectively. This allows joint transient expression in CHO-EBNA cells to produce IgG1 isotype monoclonal antibodies. These constructions were validated by sequencing and were named pEE-aTNF-IgG1Hc for the heavy chain and pEE-aTNFLc for the light chain (FIG. 9 shows the amino acid sequences of the variable domains).

To obtain a "no effect" LALA variant of anti-TNFα IgG1 (Woodle et al., *Transplantation* 68(5):608-16 (1999)) with the variable domains shown in FIG. 9, amino acid substitutions L234A/L235A (Kabat nomenclature) were introduced using oligonucleotide-directed mutagenesis in the pEE-aTNF-IgG1Hc construct via PfuUltraHS polymerase (Stratagene) according to the published protocol (Q5® Site-Directed Mutagenesis Kit (NEB)). PCR products were fractionated on a low melting point agarose gel and purified on columns. After the ligation reaction, the DNA was transformed into *E. coli*. The target sequence was validated by sequencing and designated hereinafter as pEE-aTNF-IgG1HcLALA.

In addition, using as a base the high affinity VHH sequences against IL-17A and IL-17F detected in Example 8, the VHH17 gene was synthesized (SEQ ID NO: 4; FIG. 9). An original set of mutations specific to human VH germline was introduced (Q5V, S11L, D61A, Y77N, R93V) as well as the combination of mutations E44G/R45T at the site of inter-subunit contact between the heavy and light chain variable domains (VH and VL). As shown previously (RU 2014138740), this provides stability of the VHH derivative in combination with an antibody light chain.

Further, according to standard genetic engineering procedures, the VHH17 gene (SEQ ID NO: 1) was cloned at the N-terminus of the light chain pEE-aTNFLc construct, separated from the light chain by a specific 13-amino acid flexible linker necessary for correct independent folding of both polypeptides within fusion molecules and independent binding with different antigens. The resulting construct was named pEE-VHH17-77N-aTNFLc.

Different amino acid substitutions were introduced through oligonucleotide-directed mutagenesis in calculated positions in the CDRs of heavy chain pEE-aTNF-IgG1HcLALA and light chain pEE-VHH17-77N-aTNFLc (see the Table in FIG. 10) (nomenclature Kabat) using PfuUltraHS polymerase (Stratagene) according to the published protocol (Q5® Site-Directed Mutagenesis Kit (NEB)) following the procedure described above. The mutations in the clones selected for further work are indicated in FIG. 10.

Constructs containing the heavy and light chain mutations were combined pairwise to obtain various paired combinations and to hold transient accumulation as described in Example 2. This resulted in generation of 1 variant (MabC) with no mutations in the CDRs of the anti-TNFα domain, and 32 variants of the trispecific antibody (Mab1-32; FIG. 11). The productivity of all the variants was close to or above 100 mg/l, which is satisfactory for further research of their properties.

Example 11: Comparative Analysis of Neutralization of Tumor-Alpha Necrosis Factor By Tri-Specific Anti-IL-17A/Anti-IL-17F/Anti-TNFα Binding Molecules Test solutions of antibodies were titrated in a 96-well plate from a concentration of 500 ng/ml in increments of 2, 100 µl of solution per well. A solution of recombinant human TNFα at a concentration of 500 µg/ml was prepared and then 50 µl added to each well with the test samples. Plates were incubated for 1 hour at 37° C. in a $CO_2$ incubator.

WEHI-13VAR cells were suspended at a concentration of $1×10^6$ cells/ml and introduced into each well at 50 µl with the test solutions. The plates were incubated at 37° C. in a $CO_2$ incubator for 20-24 hours. The number of living cells was measured using the vital stain Alamar Blue. After completion of incubation, 20 µl of Alamar Blue reagent was added to each well of analyte plate, then plates were shaken for 5 minutes at room temperature on an orbital shaker. The plates were incubated at 37° C. for 16-20 hours. Fluorescence readings were evaluated in relative fluorescence units at excitation/emission wavelengths of 544/590 nm using a Fluoroskan Ascent FL device. For data analysis, Microsoft Excel was used to plot dependency diagrams for the fluorescence signal and the concentration of the test and standard samples.

Figure 13:
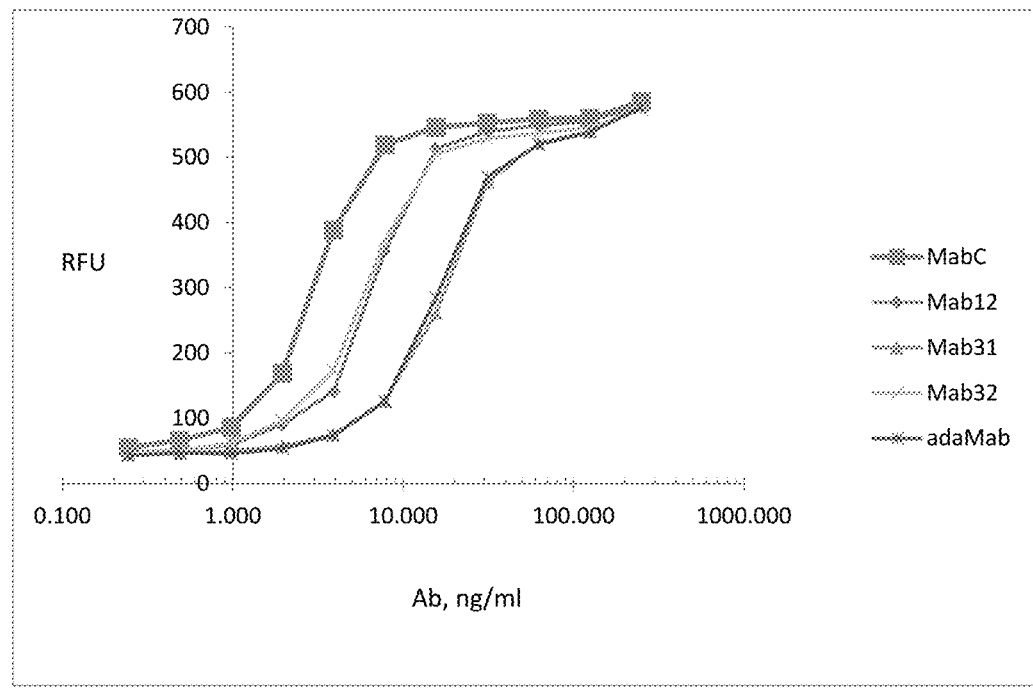
FIG. 13 shows a graph of the anti-TNFα activity of the three anti-IL-17A/anti-IL-17F/anti-TNFα tri-specific antibody variants (Mab12, Mab31, and Mab32) in a cytotoxic TNFα-dependent assay using WEHI-13VAR cells.

The table in FIG. 12 shows the results of comparative analysis of the antagonistic activity of the 32 mutants tri-specific antibodies compared to the non-mutated variant MabC and the monospecific anti-TNFα antibody adalimumab. On the basis of this analysis, the six best variants were selected and tested to identify the best three: Mab12 (ED50=4 ng/ml), Mab31 (ED50=20 ng/ml), and Mab32 (ED50=4 ng/ml). FIG. 13 shows a diagram of the comparative analysis of these variants relative to controls. On the basis of this analysis, Mab12 variant has been selected for follow-up, and was named BCD-121.

Figure 14:
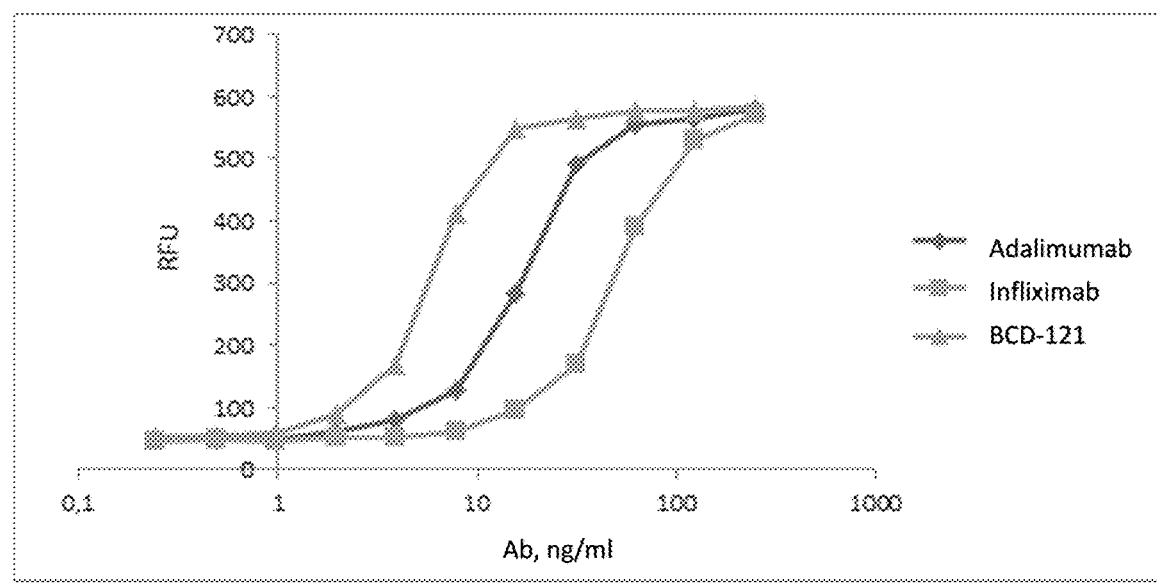
FIG. 14 shows a graph of anti-TNFα activity for anti-IL-17A/anti-IL-17F/anti-TNFα tri-specific antibody BCD-121 and the two commercial monospecific anti-TNFα antibodies adalimumab and infliximab in a TNFα-dependent cytotoxicity assay using WEHI-13VAR cells.

Further, using the same method, trispecific candidate BCD-121 was compared to the two anti-TNFα monospecific antibodies infliximab and adalimumab. The results confirmed that BCD-121 demonstrates greater antagonistic activity than adalimumab (5-fold excess) and infliximab (10-fold excess), with an EC50 of 6 ng/ml (FIG. 14).

Figure 15:
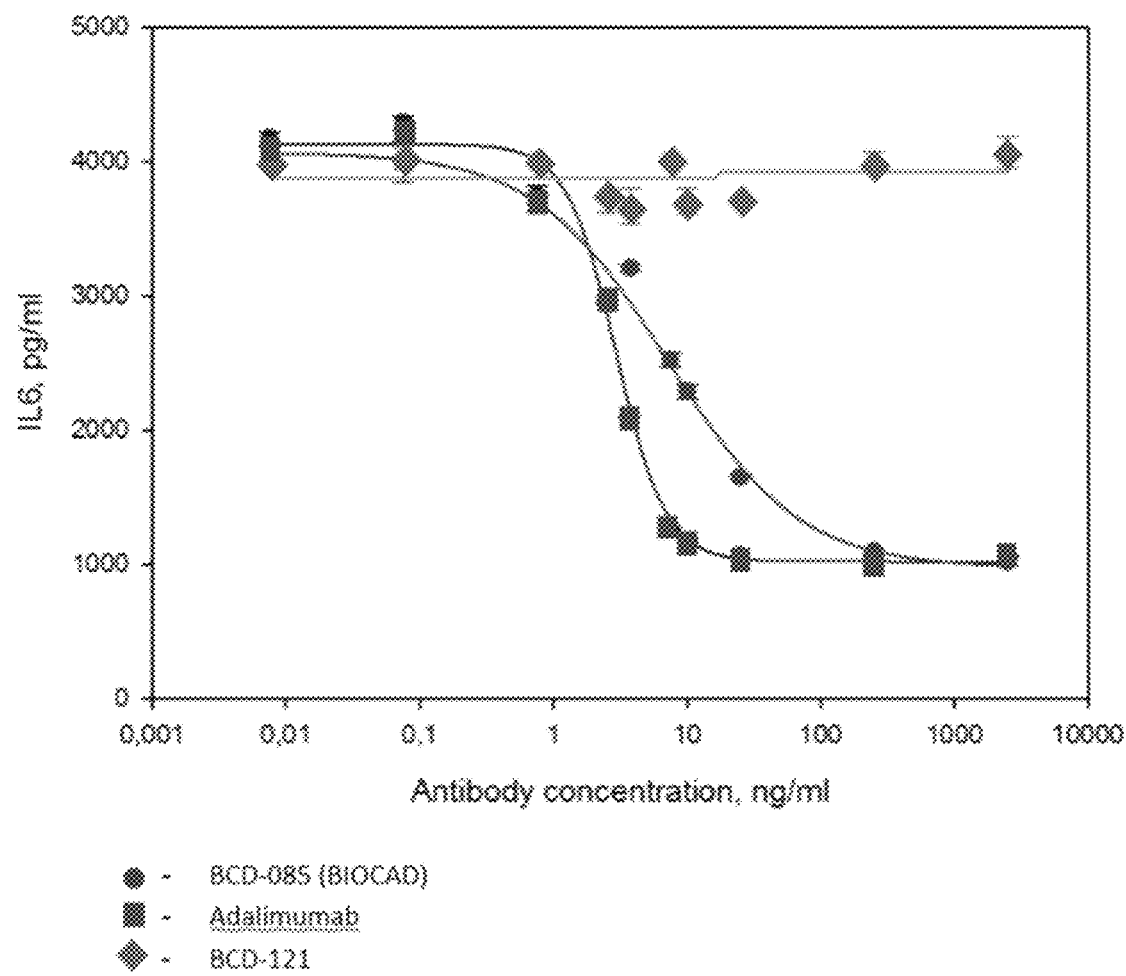
FIG. 15 is a graph showing the ability of BCD-121 to block function of IL-17A-dependent IL-6 production in HT1080 cells as compared to a positive control (monospecific anti-IL-17A antibody BCD-085) and a negative control (anti-TNFα antibody adalimumab).

Example 12: Comparative Analysis of the Inhibition of IL-17A-Dependent IL-6 Production By Trispecific Anti-IL-17A/Anti-IL-17F/Anti-TNFα Binding Molecules The neutralizing activity of trispecific candidate BCD-121 (see Example 10) was analyzed using the ability of IL-17A to induce the production of IL-6 by human HT1080 cell lines (ATCC: CCL-121) in the presence of human recombinant IL-17A and TNFα. Cells were grown in DMEM medium supplemented with 10% inactivated fetal serum, glutamine, and gentamycin. The cells were added to 96-well flat bottom cell culture plates at $5×10^4$ per well and were left for 5 hours to attach. A mixture of recombinant IL-17A at 40 ng/ml was incubated with dilutions of antibodies for one hour at 37° C. The cytokine/antibody mixture was then added to the cells and left overnight. The production of IL-6 in the HT1080 cells culture was proportional to the added quantity of IL-17A. The amount of released IL-6 in cell supernatants was determined by ELISA using "DuoSet ELISA Development System Human IL6" (R&D System, Cat. No. DY206). The results are shown in FIG. 15. Reproduced anti-TNFα monospecific antibody adalimumab was used as a negative control and anti-IL-17A monospecific antibody BCD-085 was used as a positive control (BIOCAD). As can be seen from the graph, while adalimumab did not inhibit IL-6 production, and BCD-085 inhibited IL-6 production with an $IC_{50}$ of about 9.2 ng/mL, BCD-121 antibody advantageously inhibited IL-6 production with an $IC_{50}$ of 3.5 ng/mL. Thus, candidate antibody BCD-121 is the most potent antagonist of IL-6 production in this assay.

Example 13: Comparative Analysis of Inhibition of Dual IL-17A/TNFα-Dependent IL-6 Production By Tri-Specific Anti-IL-17A/Anti-IL-17F/Anti-TNFα Binding Molecule BCD-121

Figure 16:
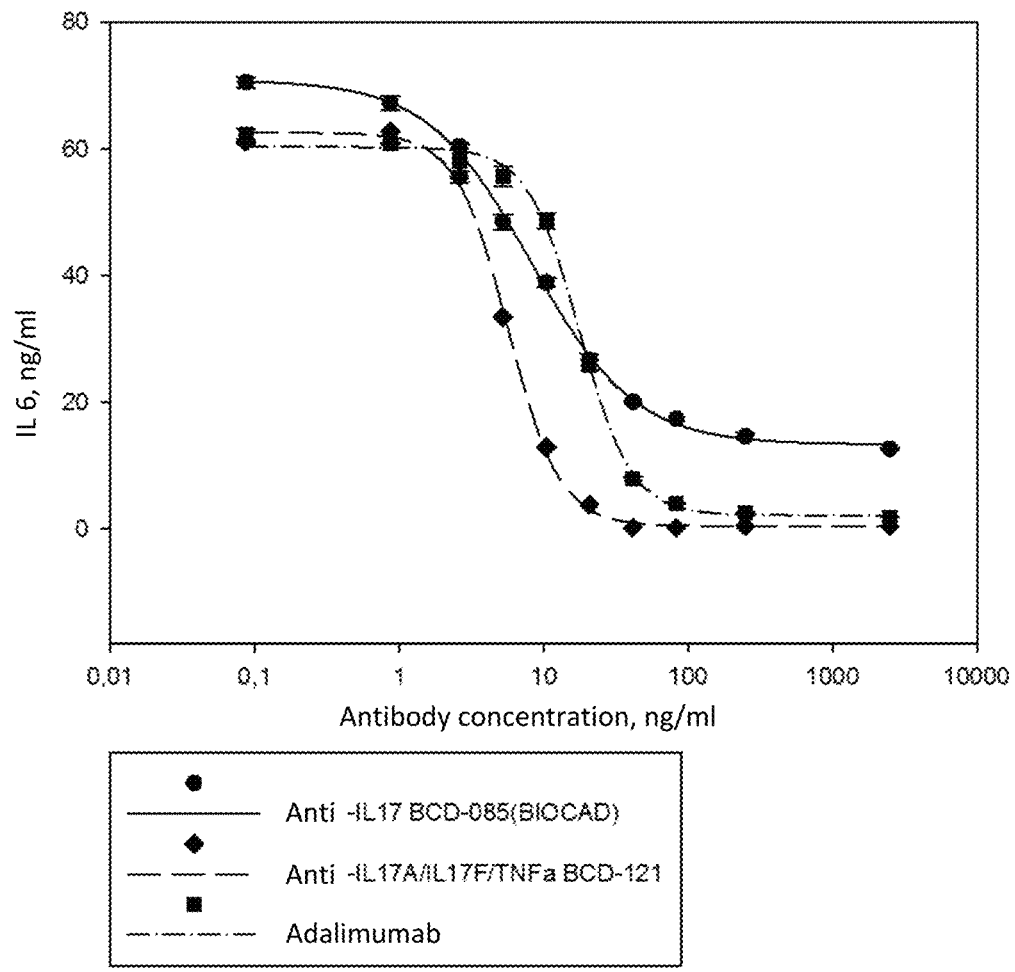
FIG. 16 is a graph showing the ability of BCD-121 to block dual IL-17A/TNFα-dependent IL-6 production in HT1080 cells as compared to a positive control (monospecific anti-IL-17A antibody BCD-085) and a negative control (reproduced anti-TNFα antibody adalimumab).

The ability of IL-17A or dual IL-17A/TNFα to induce the production of IL-6 by human HT1080 cell lines (ATCC: CCL-121) was used to analyze the neutralizing activity of tri-specific binding molecule candidate BCD-121 (see Example 10) in the presence of human recombinant IL-17A and TNFα. Cells were grown in DMEM medium supplemented with 10% inactivated fetal serum, glutamine and gentamycin. $5×10^4$ per well of cells were added to 96-well flat bottom cell culture plates. The cells were left for five hours to attach. A mixture of recombinant IL-17A at 40 ng/ml and TNFα at 20 ng/ml was incubated with dilutions of antibodies for one hour at 37° C. Then, the mixtures of cytokines and antibodies were added to the cells and left overnight. The production of IL-6 in HT1080 cell culture was proportional to the quantity of IL-17A added. The amount of released IL-6 in cell supernatants was determined by ELISA using "DuoSet ELISA development system human IL6" (R&D System, Cat. No. DY206). The results are shown in FIG. 16. Reproduced anti-TNFα monospecific antibody adalimumab and anti-IL-17A monospecific antibody BCD-085 (BIOCAD) were used as controls. As can be seen from the graph, the BCD-121 tri-specific antibody demonstrated an advantageous effect in comparison with the monospecific antibodies, showing an IC50 value of about 25 pM and an almost undetectable amount of IL-6 at the lower plateau. By contrast, the control antibody Aadalimumab had an IC50 value of about 100 pM. BCD-085 showed a similar IC50 value of about 25 pM, but had a lower threshold plateau 20 times greater than BCD-121. Thus, BCD-121 is the most potent antagonist of IL-6 production in the assay used.

Example 14: Analysis of Antibody-Dependent Cellular Cytotoxicity (ADCC) of the Tri-Specific Anti-IL-17A/Anti-IL-17F/Anti-TNFα Binding Molecule BCD-121 in Jurkat-tmTNFα Cells For use in the quantitative assay below, Jurkat-tmTNFα c1.8 cell culture was collected from flasks and centrifuged for 5 minutes at 200 g. The supernatant was decanted, and washed once more in a medium for quantitative determination.

The cell pellet was suspended in 5 ml of medium for quantitative determination. Cell viability and number were determined. A cell suspension for seeding white 96-well culture plates was prepared at $3 \times 10^5$ cells/ml.

The test sample was diluted into the wells of a 96-well plate. In wells with test samples, the Jurkat-tmTNFα c1.8 cell suspension was added, and the plate was incubated in a $CO_2$ incubator for 15-30 minutes.

A suspension of PBMC cells was prepared with a concentration of $7.5 \times 10^6$ cells/ml and added into the wells with test samples. The plate was incubated for four hours at 37° C. in a $CO_2$ incubator.

Assay Buffer was mixed with AAF-Glo™Substrate from the set "CytoTox-Glo™ Cytotoxicity Assay," then added to each well with test samples. The plate was incubated for 15 minutes at room temperature. Luminescence was measured on a Fluoroskan Ascent FL device. By this method, the activity of intracellular proteases is determined; the luminescence signal is proportional to the number of lysed cells.

Figure 17:
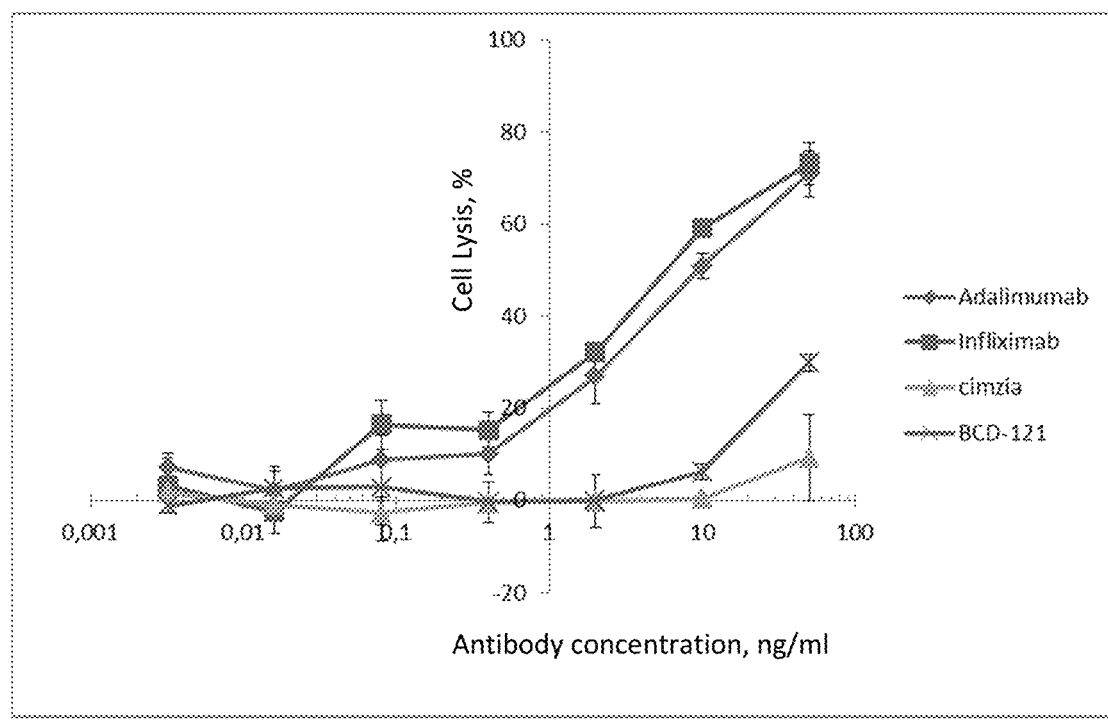
FIG. 17 is a graph showing antibody-dependent cellular cytotoxicity (ADCC) from antibody BCD-121 as compared to three commercial monospecific anti-TNFα antibodies (adalimumab, infliximab, and cimzia) based on Jurkat-tm TNFα c 1.8 cell culture.

As shown in FIG. 17, BCD-121 demonstrated approximately 100-fold less ADCC activity compared to IgG1-derived antibodies adalimumab and infliximab, and is comparable in the level of this activity to cimzia (Fab-PEG).

Example 15: Analysis of Complement-Dependent Cytotoxicity (CDC) of the Tri-Specific Anti-IL-17A/Anti-IL-17F/Anti-TNFα Binding Molecule BCD-121 in Jurkat-tmTNFα Cells Test solutions of antibodies were titrated from a concentration of 15 μg/ml in increments of 2 in 96-well plates, 50 μl per well. Human complement was dissolved 1:3 in chilled medium for analysis (RPMI with 1% BSA) and 50 μl added into wells with test samples. 50 μl of Jurkat-tmTNFα cell suspension was added to each well with samples at the concentration of $1 \times 10^6$ cells/ml ($5 \times 10^4$ cells per well). The plates were shaken for 3 min on an orbital shaker at room temperature and placed for 2-3 hours in a $CO_2$ incubator at 37 C. The number of living cells was measured using the vital stain Alamar Blue. After completion of incubation, 15 μl of Alamar Blue reagent were added to each well of analyte plate, then the plates were shaken for 5 minutes at room temperature on an orbital shaker. The plates were incubated at 37° C. for 18 to 24 hours. Fluorescence readings were evaluated in relative fluorescence units at excitation/emission wavelengths of 544/590 nm using a Fluoroskan Ascent FL device.

Figure 18:
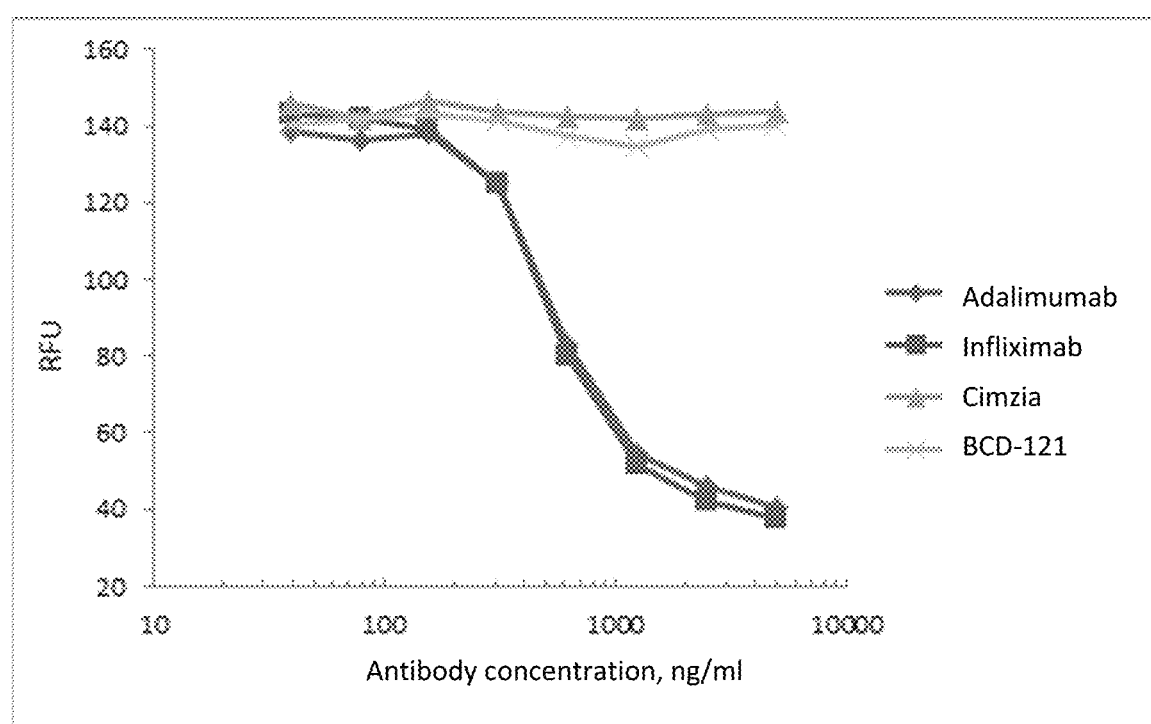
FIG. 18 is a graph showing complement-dependent cytotoxicity (CDC) from antibody BCD-121 as compared to three commercial monospecific anti-TNFα antibodies (adalimumab, infliximab, and cimzia) based on Jurkat-tm TNFα c 1.8 cell culture.

As seen in FIG. 18, BCD-121 does not have CDC activity in Jurkat-tm TNFα c1.8 cells in comparison with IgG1-derived antibodies adalimumab and infliximab, and is comparable in the level of this activity to cimzia (Fab-PEG).

Figure 19:
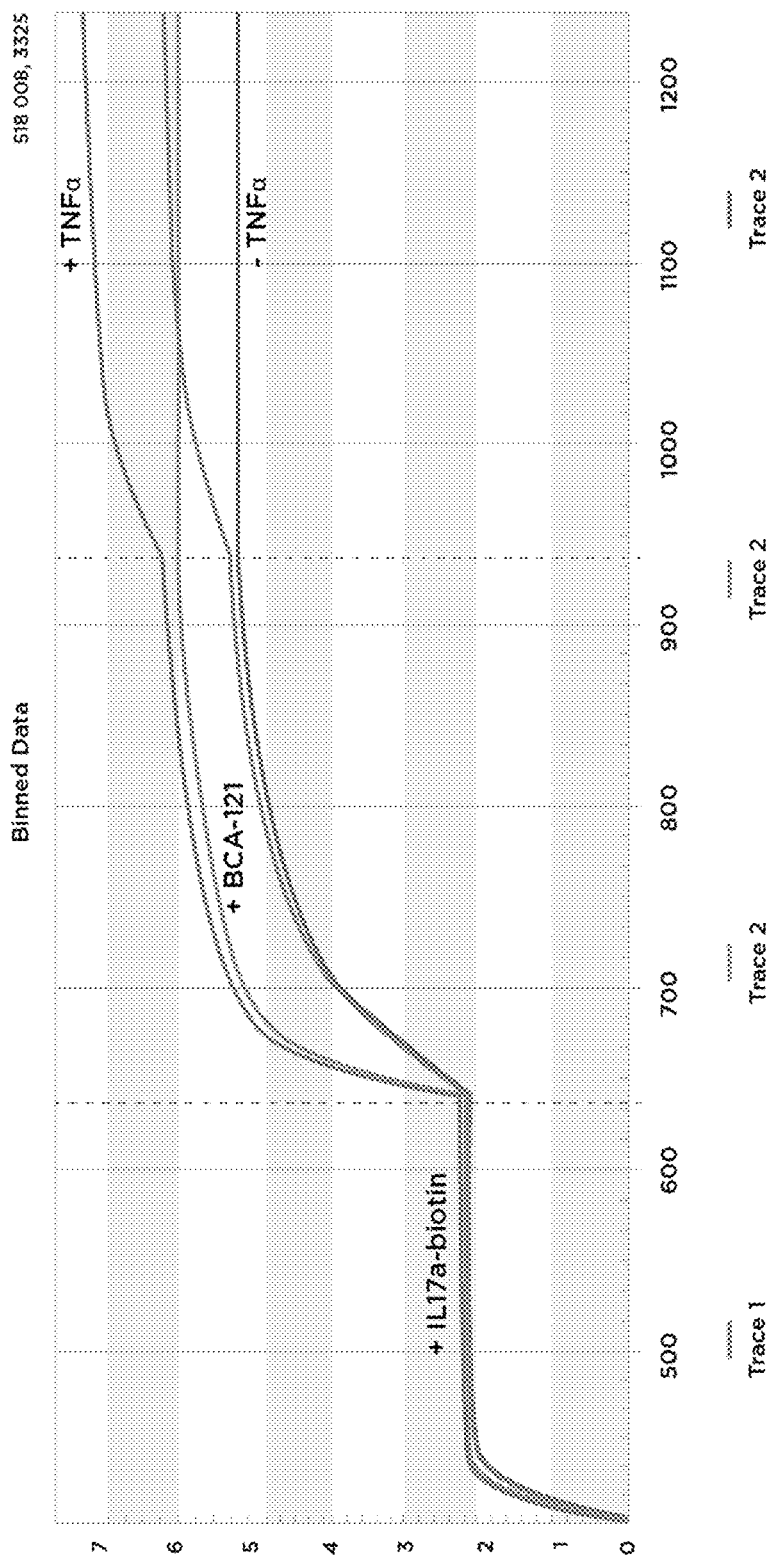
FIG. 19 is a sensogram of simultaneous "sandwich" binding of BCD-121 to both IL-17A and human TNFα using Octet RED96.

Example 16: Analysis of Simultaneous Interactions of BCD-121 with Human IL-17A and Human TNFα Using the OctetRED96 Device Analysis of simultaneous binding of BCD-121 to human IL-17A and human TNFα was carried out using the classic "Sandwich" analysis method by the Octet Red96 device (Pall-ForteBio) (FIG. 19). Analysis was performed at 30° C. using PBS containing 0.1% Tween-20 and 0.1% BSA as running buffer. During the experiment, the first antigen (IL-17A-biotin) was immobilized on streptavidin-coated sensors at a concentration of 20 μg/ml and a volume of 200 μl/well. Further sensors were immersed in an antibody solution of 200 μl/well of antibody at a concentration of 20 μg/ml. Sensors subsequently were immersed in TNFα solution at 200 μl/well at a concentration of 1 mg/ml and into saline containing no protein.

Binding curves minus baseline signal were analyzed using Octet Data Analysis (Version 7.0) according to the standard procedure.

The sensogram shown in FIG. 19 indicates that the tri-specific binding molecule BCD-121 can simultaneously bind IL-17A and TNFα.

Example 17: Analysis of BCD-121 Binding with Orthologous IL-17A and TNFα Ligands Using the Biacore T200 Device The analysis was conducted using the Sandwich approach using IL-17A and TNFα preparations produced by Sino Biologics. After activation of the chips, individual ligand was nonspecifically (by NH2 groups) immobilized on the biosensor surface at a concentration of 20 μg/ml. Loading of the antibody was then performed at a concentration from 1 to 25 μg/ml. Thereafter, the sensors were immersed in the running buffer for the complex dissociation step. The flow rate was 10 μl/min.

Analysis of the obtained data was performed using BIA Evolution 3.1 software and the Heterogeneous Ligand model.

Table 3 shows data on the interaction of BCD-121 with orthologous IL-17A and TNFα ligands from human and primate. BCD-121 demonstrates very high affinity (below pM) for all of the ligands.

TABLE 3

Affinity of BCD-121 to IL-17A, IL-17F and TNFα

|  | IL-17A human KD, M | IL-17A cyno KD, M | IL-17F human KD, M (OctetRED96) |
|---|---|---|---|
| BCD-121 | <<1.0E−12* | ~1.0E−12 | ~4.0E−9 |
|  | TNFα human KD, M | TNFα cyno KD, M | TNFα multta KD, M |
| BCD-121 | <<1.0E−12* | <<1.0E−12* | ~1.0E−12 |

*below the threshold sensitivity of the Biacore T200 device

Example 18: Enzyme Immunoassay of the Interaction Between BCD-121 and Various IL-17 Family Antigens (A, B, C, D, E, F and A/F)

ELISA was used to measure the comparative binding of BCD-121 to human IL17 family antigens. For the binding analysis, the wells of ELISA plates (medium binding from Greiner bio one) were individually coated with 50 μl of human IL-17A, IL-17B, IL-17C, IL-17D, IL-17E, IL-17F, or IL-17A/F (R&D Systems) at a concentration of 1 μg/ml (in 1× coating carbonate buffer), hermetically sealed, and incubated overnight at 4 C. All subsequent steps were performed by standard EIA protocol. To block non-specific binding blocking, buffer BB was added (200 μl of 0.5% skim milk in PBS). Plates were incubated on a shaker for one hour at room temperature. After washes with PBS-Tween, 50 μl of the test antibodies were added to each well at a concentration of 5 μg/ml in PBS-Tween. Plates were again incubated with shaking for one hour at room temperature, then each well of the plates was washed three times with PBS-Tween buffer. After washing, human anti-Fab HRP-conjugated secondary antibody (from Pierce-ThermoScientific) was added (50 μl/well) at a ratio of 1:5000 in PBS-Tween. Plates were shaken on a rotary shaker (50 min, room temperature) and washed three times with PBS-Tween buffer, as described above. The colorimetric signal was developed by addition of TMB (50 μl/well) until saturation (on average 3-5 minutes), then further development was stopped by adding the terminating solution (30 l/well 10% sulfuric acid). The color signal was measured at 450 nm using a suitable plate-reader (Tecan-Sunrise; Tecan). The extent of antibody binding was proportional to color signal production.

Figure 20:
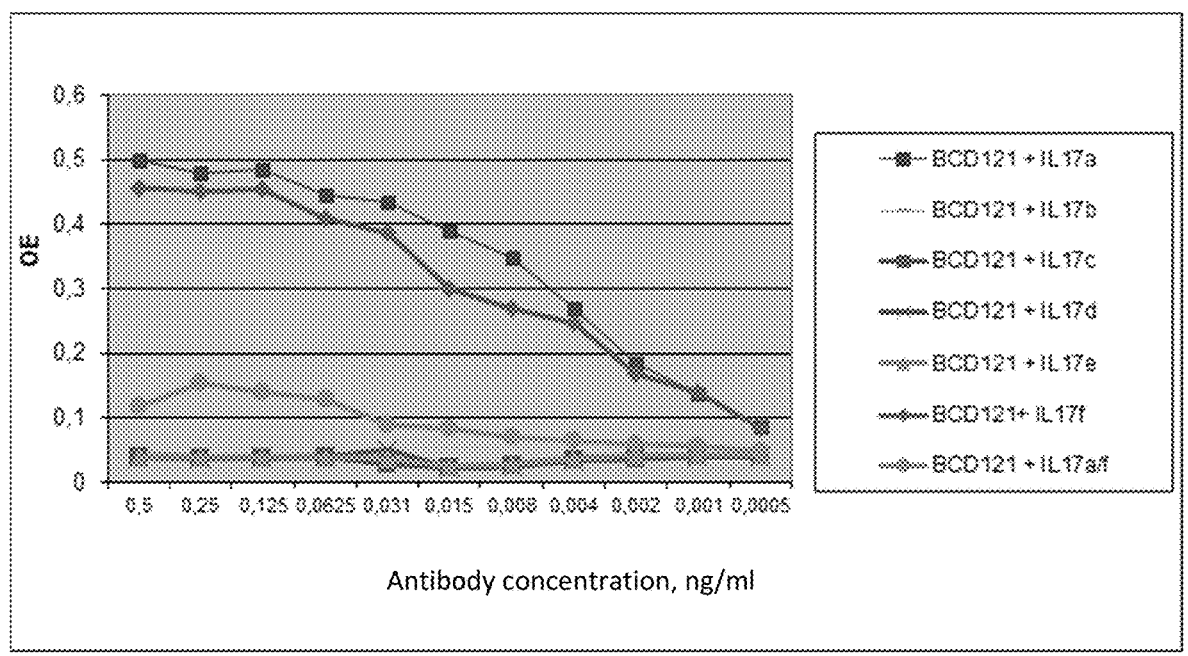
FIG. 20 is a graph showing ELISA results for BCD-121 antibody binding to different ligands in the human IL-17 family.

The result of the interaction of BCD-121 with members of the human IL-17 family is presented in FIG. 20. As can be seen from the curve of optical absorption concentration for BCD-121, the tri-specific binding molecule specifically interacts with IL-17A and IL-17F with high affinity, and with their natural heterodimer IL-17A/F with low affinity. BCD-121 is not cross-reactive with other members of the family.

Example 19: Enzyme Immunoassay of the Interaction of BCD-121 with Guinea Pig, Rabbit, and Mouse TNFα

An ELISA assay was performed using a similar protocol to that described in Example 16. Human, guinea pig, rabbit, and mouse TNFα antigens are from R&D Systems.

Figure 21:
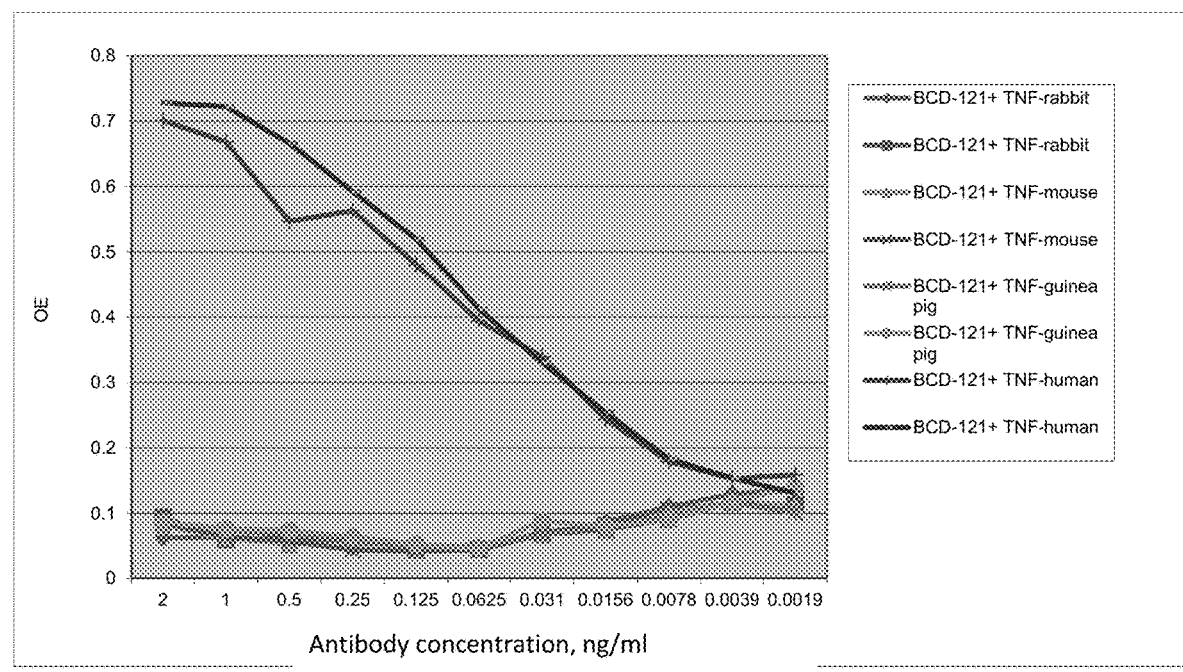
FIG. 21 is a graph showing ELISA results for BCD-121 antibody binding to different orthologous TNFα proteins.

The result of interaction of BCD-121 with human, guinea pig, rabbit, and mouse TNFα is shown in FIG. 21. As can be seen from the curve for optical absorption-concentration of BCD-121, the tri-specific binding molecule reacts specifically and with high affinity only to human TNFα. BCD-121 is not cross-reactive with TNFα orthologs (except primate TNFα orthologs, as shown in Example 17).

Example 20: Determination of Thermal Stability By Assessing the Protein Aggregation Point Using the Dynamic Light Scattering Method (DLS)

Determination of the aggregation point of the samples (1 mg/ml) was performed on the Zetasizer Nano ZSP device. 0.5 ml of solution was placed in a dust-free quartz cuvette, which was gradually heated in the device from 50 to 85° C. in 1.5° C. steps. Each temperature was maintained for 30 seconds with constant measuring of scattered light intensity. The intensity of the scattered light was detected at an angle θ=173°.

Figure 22:
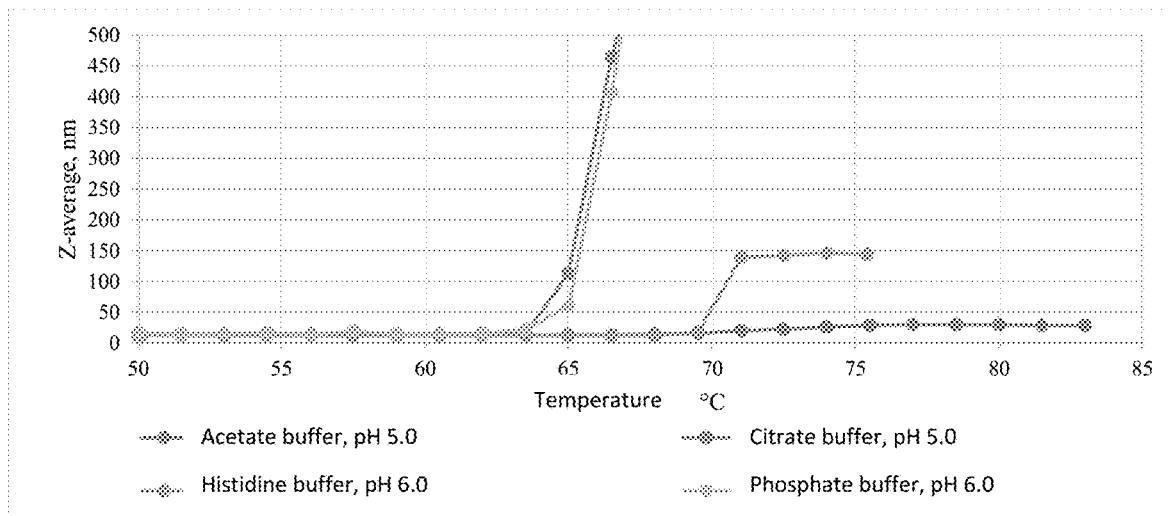
FIG. 22 is a graph showing the thermal stability of BCD-121 protein aggregation using dynamic light scattering (DLS). The graph shows the average particle size (Z-average) versus temperature for four buffers.

Data obtained using the dynamic light scattering method is shown in FIG. 22 and Table 4 for protein aggregation points in four different buffers.

TABLE 4

BCD-121 Aggregation Point Measured by Dynamic Light Scattering

| | Incurred samples | Aggregation point |
|---|---|---|
| BCD-121 | Acetate buffer, pH 5.0 | 69.5° C. |
| | Citrate buffer, pH 5.0 | 66.5° C. |
| | Histidine buffer, pH 6.0 | 69.5° C. |
| | Phosphate buffer, pH 6.0 | 65.0° C. |

Example 21: Determination of Thermal Stability During Long-Term Exposure By the Thermostress 50° C. Method Samples of protein at a concentration of ~5 mg/ml were divided into 3 portions of 200 μl each and placed in separate tubes: 1 tube for each composition was stored in the refrigerator at +4° C., and the other two were set in a test tube heater and incubated at 50° C. for 6 and 24 hours, respectively. After warming, the tubes were removed from the heater, allowed to stand at room temperature for 15 min, centrifuged at 8000 rpm for 5 minutes, and the supernatants transferred for gel filtration with a UV detector.

Figure 23:
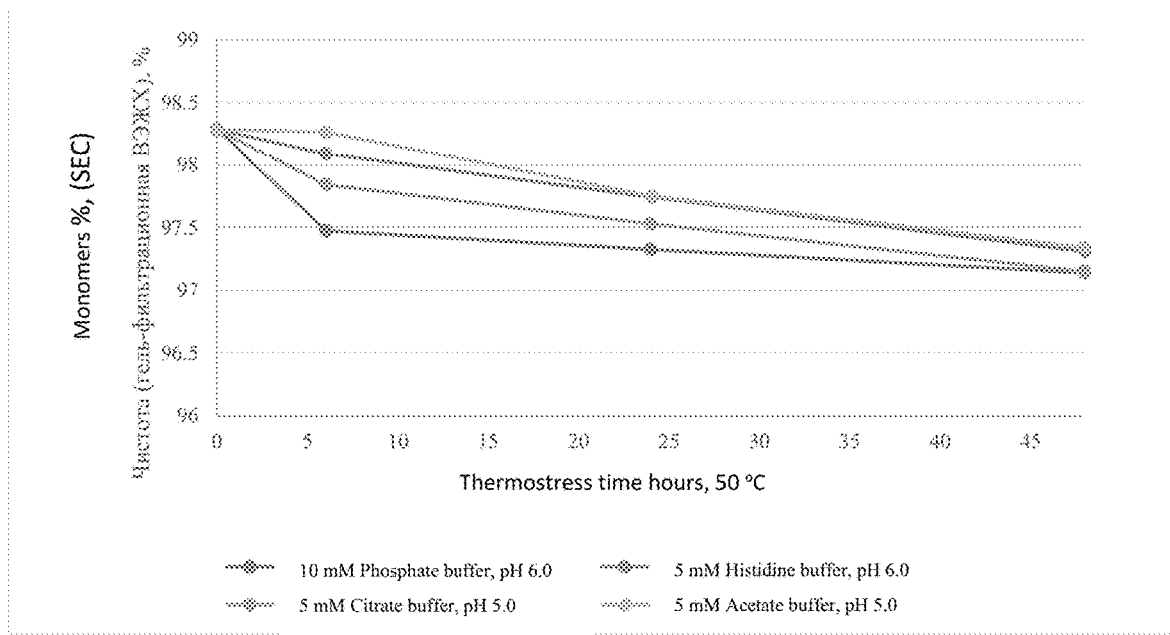
FIG. 23 is a graph showing the thermal stability of BCD-121 during long-term exposure using Thermostress 50° C. in four different buffer solutions.

The research standard for size exclusion chromatography was used (Bio-rad; cat. number 151-1901). The data for BCD-121 stability in various buffers under prolonged heating at 50° C. is shown in the table in FIG. 23.

The results show that all tested buffers provide satisfactory BCD-121 thermostress stability.

Example 22: Creation of Stable Cell Lines for Production of BCD-121

A stable producer cell line for BCD-121 was obtained by transfection with electroporation using the Neon Transfection System (Life Technologies) slurry parental cell line CHO-S vector constructions, containing the light and heavy antibody chains in an optimized ratio. Clonal lines with high productivity (up to 1000 mg/L) were obtained using a ClonePix robot platform (Molecular Devices) and the preliminary stages of minipool selection were performed using antibiotics in various culture formats. Productivity analysis was performed using the analytical system Octet RED96 (Pall Life Sciences). DOE on the selection of basic medium and cultivation schemes was implemented using the automated system Biomek FX robotics (Beckman Coulter). For culturing the producer cells, a serum-free medium and fittings were used, which did not contain animal protein. Accumulation of BCD-121 for preclinical research was carried out in a HyClone single-use bioreactor (Thermo Fisher Scientific) with a working volume of 50 l.

Example 23: Isolation of BCD-121 from the Productive Stable Cell Line Environment Clarification of the culture liquid containing BCD-121 was performed on a deep-bed filter Millistak COHC (Merck-Millipore). Primary antibody purification was performed on affinity resin with protein A, using a specific target protein, and the antibody was eluted with glycine buffer at pH3.3-3.8. The eluate was incubated at an acidic pH for 30-60 minutes for viral inactivation and then neutralized with a solution of 1 M Tris-OH. Final chromatographic purification was performed on the sorbent CHT™ Ceramic Hydroxyapatite (Bio-Rad) to remove residual DNA, protein producing cells, cleaved ligand affinity sorbent aggregates, and antibody fragments. For this method, protein solution was applied to the sorbent prepared at pH 7.5, followed by a specific elution gradient with sodium chloride. The purified protein was filtered for viruses using a set of Viresolve PRO filters (Merck Millipore). The protein was concentrated in a tangential flow on the tapes with a cut-off limit of 50 kDa followed by diafiltration against a final buffer containing acetate buffer (pH5.0), sorbitol, and polysorbate-80. Protein concentration in the final solution was at least 70 mg/ml.

Figure 24:
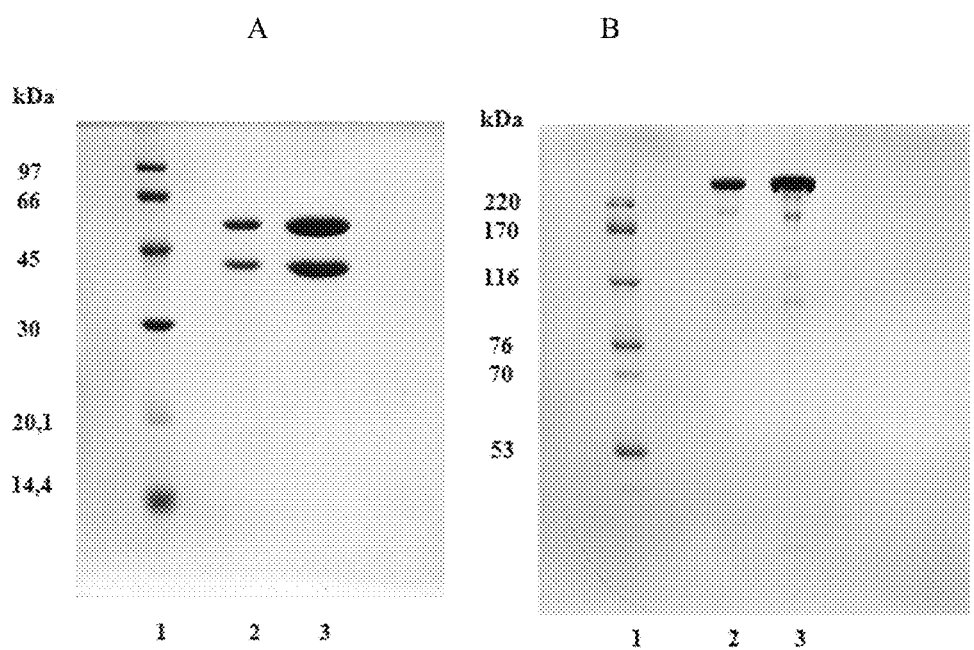
FIG. 24 shows a purity analysis of BCD-121 obtained from the culture medium of a stable cell line producer according to an optimized purification scheme. Panel A: reducing conditions (+β-ME). Panel B: non-reducing conditions (−β-ME). Lanes 2 and 3: 10 and 40 μg applied, respectively.
Figure 25:
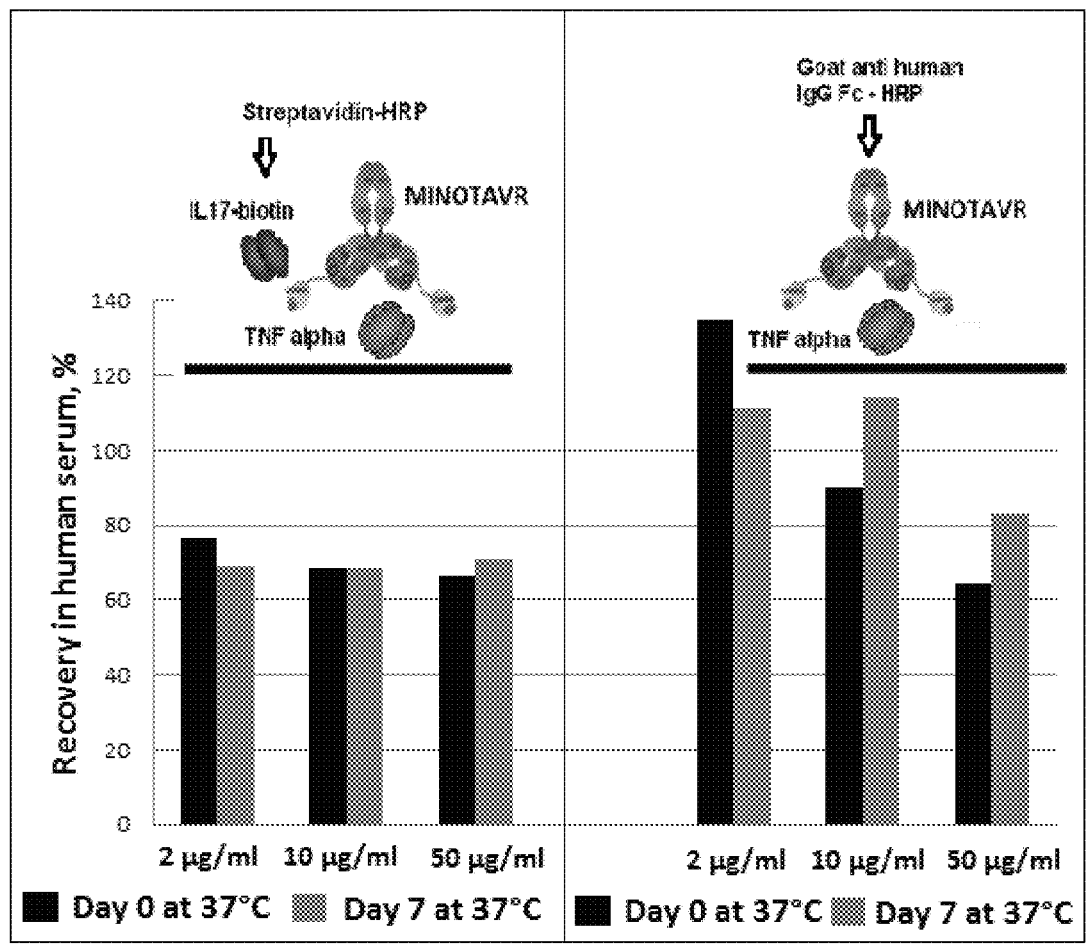
FIG. 25 is a graph demonstrating BCD-121 stability in pure human serum by ELISA.

Purification results are presented in FIG. 24. Vertical electrophoresis using a polyacrylamide gel with SDS under reducing and non-reducing conditions demonstrated the purity of the product, which is sufficient for use in a pharmaceutical composition.

Example 24: Enzyme Immunoassay Showing BCD-121 Stability in Pure Human Serum To estimate the stability of BCD-121 in pure human serum, the tri-specific antibody was added at concentrations of 2, 10, and 50 µg/ml to a pure human serum mix obtained from seven healthy donors, preserved with 0.01% of thimerosal, and stored for 7 days at 37° C. After 7 days, the concentration of BCD-121 was measured by ELISA in two assay formats: immobilized TNFα and biotinilated IL17 with Streptavidin-HRP conjugate detection and immobilized TNFα with Goat Anti-human IgG Fc—HRP conjugate detection. Serum samples in which BCD-121 was added to concentrations of 2, 10, and 50 µg/ml immediately before ELISA measurement were used as a control. Measurement was performed as follows: control and stored serum samples with 2, 10, or 50 µg/ml of BCD-121 were diluted to 100 ng/ml (20, 100, and 500-fold, respectively) and actual concentration was measured against a standard calibration curve (from 6.25 to 200 ng/ml) dissolved in PBS-Tween. All ELISA steps were performed by standard EIA protocol. 100 µl of diluted samples or calibration standards were added to microwells precoated by TNFα. The concentration of coated TNFα was 2 µg/ml in 20 mM carbonate buffer at pH 9.5. A blocking buffer (BB: 200 µl of 0.5% skim milk in PBS) was then added to the plates. The plates were incubated on a shaker for one hour at room temperature. After washes with PBS-Tween, 100 µl of the biotinilated IL17 (3 µg/ml) or Goat Anti-human IgG Fc—HRP (from Sigma, in a ratio 1:20000) were added per well with concentration in PBS-Tween. The plates were again incubated with shaking for one hour at room temperature, then each well of the plates was washed three times with PBS-Tween buffer. 100 µl of Streptavidin-HRP conjugate at a ratio of 1:20000 (Sigma) was additionally added into wells in which biotinilated IL17 was previously added. After subsequent incubation for one hour and washing, the colorimetric signal was developed by addition of TMB (100 µl/well) until saturation (on average 10-15 minutes), then further development was stopped by adding the terminating solution (50 µl/well 10% sulfuric acid). The color signal was measured at 450 nm using a suitable plate-reader (Tecan-Sunrise; Tecan). The amount of BCD-121 binding was proportional to color signal production. The calibration curve concentration was multiplied by the dilution factor and expressed as % of theoretically added in serum BCD-121 concentration.

Example 25: Evaluating the Effectiveness of the BCD-121 Anti-IL-17A/Anti-IL-17F/Anti-TNFα Binding Molecule In Vivo The research below was conducted on male cynomolgus monkeys (*Macaca fascicularis*) using a model of collagen-induced arthritis. The total number of animals in the experiment was 20, in five groups of four monkeys each. In the experiment, four doses of the product were used: 0.2 mg/kg; 1.0 mg/kg; 5.0 mg/kg; and 10.0 mg/kg. Control group animals received a placebo. Administration of the product and placebo started after preliminary sensitization with collagen. During this study, the animals of all groups were measured to calculate the articular surface of the APW. At the end of the study, metacarpophalangeal and metatarsophalangeal-phalangeal joints were taken to assess the severity of destructive changes. The schematic for the experimental groups is shown in Table 5 below.

TABLE 5

| Group Number | Number of animals | Product | Route of administration | Dose |
|---|---|---|---|---|
| 1 | 4 (♂) | BCD-121 | subcutaneous | 0.2 mg/kg |
| 2 | 4 (♂) | | | 1.0 mg/kg |
| 3 | 4 (♂) | | | 5.0 mg/kg |
| 4 | 4 (♂) | | | 10.0 mg/kg |
| 5 | 4 (♂) | Placebo | | — |

For arthritis induction, an emulsion of bovine type II collagen (Sigma) was administered to the animals three times.

The First Administration of Collagen:

The total amount of administered collagen was 2 mg per experimental animal. For this purpose, 2 mg of collagen were dissolved in 0.7 ml of 0.1 M acetic acid. 0.7 ml of complete Freund's adjuvant was added to this solution.

Animals were kept for 28 days after the first administration of collagen.

The Second Administration of Collagen:

The total amount of administered collagen was 3 mg per experimental animal. For this purpose, 3 mg of collagen were dissolved in 1 ml of 0.1 M acetic acid. 1 ml of complete Freund's adjuvant was added to this solution.

Animals were kept for 21 days after the second administration of collagen.

The Third Administration of Collagen

The total amount of administered collagen was 3 mg per experimental animal. For this purpose, 3 mg of collagen were dissolved in 1 ml of 0.1 M acetic acid. 1 ml of complete Freund's adjuvant was added to this solution.

Measuring of the size of the joints was carried out by dividers at the following time points:

Before the first administration of collagen;

At the time of the second administration of collagen; and

Weekly after the second administration immediately before the administration of the collagen for 7 weeks.

During the measurement process the longitudinal and transverse axis of the joint was estimated. This procedure has been carried out for all the metacarpophalangeal and metatarsophalangeal joints except the thumb. Calculation of the area was carried out by the formula:

$$JA = \text{the value for the longitudinal axis} \times \text{the value for the transverse axis} \times 3.14 \times 0.25.$$

The data for 16 joints of each animal was used to calculate the percent of inflammation area (PIA). This calculation was carried out by the formula:

$$JA \text{ value on the day of the experiment} \times 100$$

the average value for JA before the induction of arthritis

Figure 26:
FIG. 26 is a graph showing the pharmacodynamic properties of BCD-121 in a M. fascicularis collagen-induced arthritis (CIA) model.

The results, shown in FIG. 26, demonstrate the dose-dependent anti-inflammatory effect of BCD-121 in a monkey CIA model.

Example 26: Evaluation of Toxicokinetics of the BCD-121 Anti-IL-17A/Anti-IL-17F/Anti-TNFα Binding Molecule The toxicokinetics assay was performed on cynomolgus macaques (cynomolgus). The research used three dose levels of the BCD-121 product. The schematic of the experimental groups is shown in Table 6 below.

TABLE 6

| Group Number | Number of animals | Product | Route of administration | Dose |
|---|---|---|---|---|
| 1 | 3 (♂) | BCD-121 | subcutaneous | Minimal |
| 2 | 3 (♂) | BCD-121 | | Medium |
| 3 | 3 (♂) | BCD-121 | | Maximal |
| 4 | 3 (♂) | Placebo | | — |

In the course of the study, the following parameters were evaluated:

Clinical examination results;
Animal's weight (before administration and on days 7, 14, 21, 28, 35 and 42 of the experiment);
Body temperature (before administration and 1, 2, 4, 6, and 24 hours after administration on days 7, 14, 21, 28, 35, and 42 of the experiment);
Urinalysis (before administration and on days 7, 14, 21, 28, 35, and 42 of the experiment);
Clinical blood analysis on parameters: number of erythrocytes, number of leucocytes, hemoglobin concentration (before administration and on days 7, 14, 21, 28, 35, and 42 of the experiment);
Biochemical analysis of serum ratios: LDH, total bilirubin, total protein, glucose, aspartate aminotransferase, and alanine aminotransferase (before administration and on days 7, 14, 21, 28, 35, and 42 of the experiment); and
Drug concentration in the blood serum of primates (0.5, 1, 3, 6, 24, 30, 48, 72, 96, 120, 144, 168, 192, 264, 336, 408, 504, 624, 720, 816, 912 and 1008 hours after administration).

The level of the drug in blood serum was assessed using ELISA and horseradish peroxidase as indicator enzyme.

Wells of 96-well microtiter plates ("Costar", Cat. No. 3590) were sensitized with recombinant human TNFα (R&D Systems, Cat N 210-TA/CF) based on 250 ng/100 μl of 20 mM Tris HCI buffer solution, pH 9.0, per well and incubated for 16-18 hours at 4° C. Antigens which were not bound were removed from the wells. In order to block non-specific binding sites, 200 μl of 20 mM Tris HCI buffer solution, pH 7.2-7.4 (TB), containing 1.0% BSA, 0.14 M NaCI and 0.05% Tween-20 (blocking buffer—BB) were introduced into each well and then the wells were incubated for 30 minutes at 37° C. BB solution was removed, and 100 μl of test serum diluted 1000-10 000-fold with BB were introduced into each well. Simultaneously 100 μl of BB containing different concentrations of BCD-121 in the range of 3.9-250 ng/ml were introduced into each well. The plates were incubated for 30 minutes at 37° C. The well contents were removed, the wells were washed 3 times each with 200 μl of TB containing 0.05 Tween-20, 100 μl of BB containing antibodies against human IgG Fc-fragment labelled with horseradish peroxidase («Sigma», USA, Cat. No. A0170 at working dilution) were introduced into each well and the wells were incubated for 30 minutes at 37° C. The well contents were removed, the wells were washed 4 times each with 200 μl of TB containing 0.05 Tween-20, and 100 μl of 0.1 M sodium acetate buffer solution, pH 5.0, containing 0.1 mg/ml tetramethylbenzidine and 0.003% $H_2O_2$ were introduced into each well. To quench the reaction, 50 μl of 2M $H_2SO_4$ were introduced into each well, then absorbance was measured in the wells using a plate spectrophotometer at 450 nm.

To determine the concentration of BCD-121 in test samples, the calibration curve of the relationship between absorbance and concentration of BCD-121 in reference standards was plotted, and using the absorbance value obtained with the test sample, the concentration of BCD-121 was determined.

Figure 27:
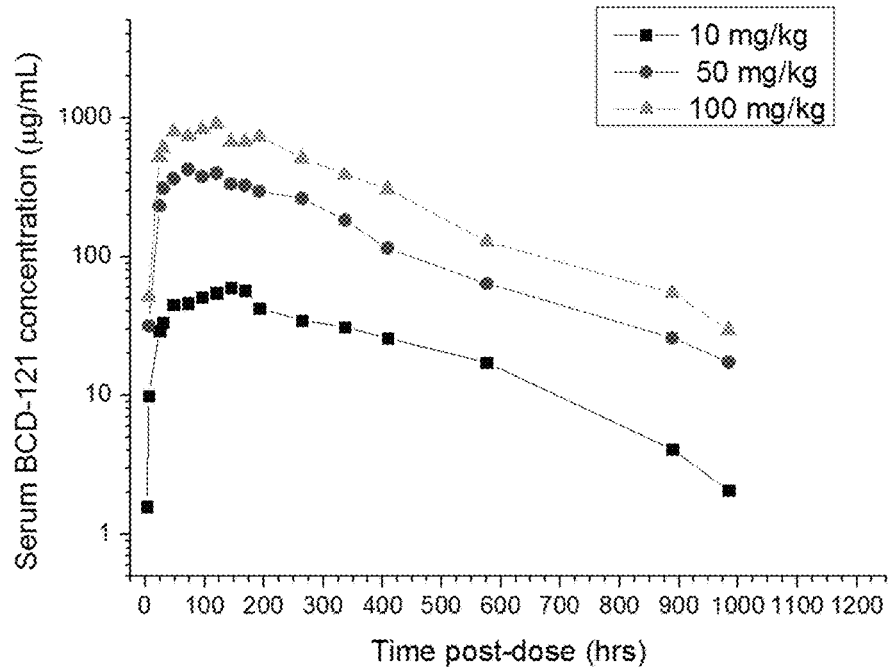
FIG. 27 is a graph showing the pharmacokinetic profile by ELISA of BCD-121 in monkeys following a single SC administration at a dose of 10, 50 or 100 mg/kg.
Figure 28:
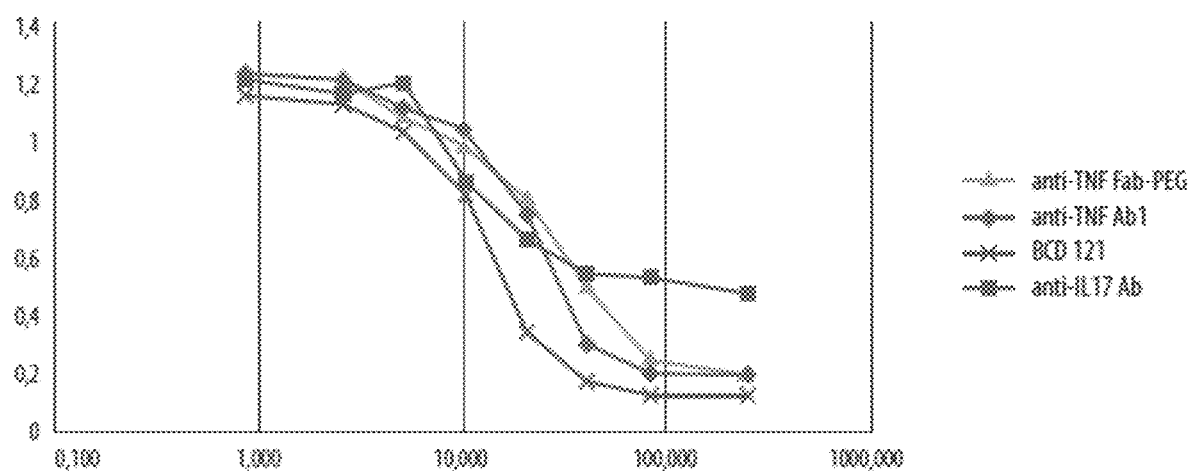
FIG. 28 is a graph showing that BCD-121 can dual block the ability of IL-17A and TNFα to induce production of IL-6 in HT1080 cells. BCD-121 more potently blocks IL-6 release than a monospecific anti-TNF Ab1, an anti-TNF Fab-PEG, or an anti-IL17 Ab (monoclonal antibody against IL-17), with an IC50 of 20 ng/ml.
Figure 29:
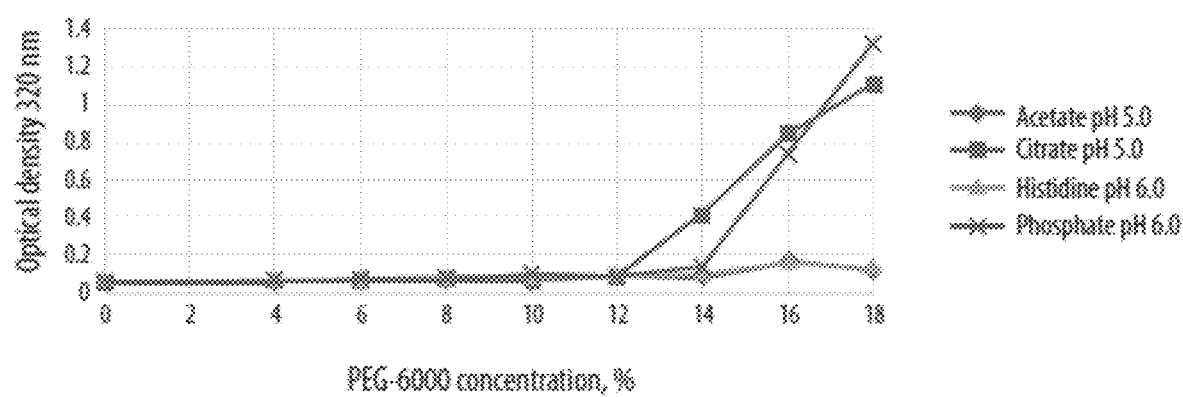
FIG. 29 is a graph showing a shaking stress aggregation assay (20 at 500 rpm) by Zetasizer nano ZSP. The data shows that BCD-121 is a highly soluble tri-specific molecule that can be used in high-concentration formulations for subcutaneous injection (above 100 mg/ml).

The lower limit of reliable BCD-121 detection was 2 ng/ml. The concentration of BCD-121 in test sera (X), in μg/ml, was calculated according to the following formula:

$$X = A \times F$$

where, A—concentration of BCD-121 table in test sample determined using calibration curve, ng/ml;
F—dilution of initial serum;
Results of the PK profile demonstrated expected levels of BCD-121 (FIG. 27). The terminal disposition half-life was calculated above 12 days. The obtained PK profile of BCD-121 in monkeys was similar to that of native human IgG antibody and had a typical dose-dependent character.

Example 27: Evaluation of Toxicity of Repeated Subcutaneous Administration in Cynomolgus Monkeys for One Month Followed By a Period Free from Administration for One Month A toxicity assay of repeated subcutaneous administration of BCD-121 for one month followed by a one month recovery period was carried out on Javanese macaques. Three dose levels were used in the experiment. The schematic of the experimental groups is shown in Table 7 below.

TABLE 7

| Group Number | Number of animals | Product | Route of administration | Dose |
|---|---|---|---|---|
| 1 | 3 (♂)<br>3 (♀) | BCD-121 | subcutaneous | Minimal |
| 2 | 3 (♂)<br>3 (♀) | BCD-121 | | Medium |
| 3 | 3 (♂) *<br>3 (♀) *<br>3 (♂)<br>3 (♀) | BCD-121 | | Maximal |
| 4 | 3 (♂)<br>3 (♀) | Placebo | | — |

In the course of the study, the following parameters were evaluated:

Clinical examination results;
Animal weight (before administration and then weekly);
Body temperature (before administration and then weekly until termination of the experiment);
Influence on the cardiovascular system for which the bioelectric activity of the heart was evaluated using a Poly-Spectrum system; evaluation was made before administration and then on weeks 3, 5, and 7 of the experiment;
Urinalysis (before administration and on weeks 3, 5, and 7 of the experiment);
Clinical blood analysis on parameters: number of erythrocytes, number of leucocytes, hemoglobin concentration, number of lymphocytes, number of monocytes, neutrophils, eosinophils, and basophiles, and platelet count (before administration, then once a week, starting from the first week of the experiment);

Assessment of the impact on the blood clotting system in terms of: activated partial thromboplastin time, fibrinogen concentration, and prothrombin time (before administration, then on weeks 3, 5, and 7 of the experiment);

Biochemical analysis of serum ratios: sodium, potassium, creatinine, urea, alkaline phosphatase, LDH, total bilirubin, total protein, glucose, triglycerides, aspartate aminotransferase, alanine aminotransferase, total cholesterol (before administration and on weeks 3, 5, and 7 of the experiment);

At the end of the administration period, satellite animals of group 3* were euthanized and subsequently pathologically examined; at the end of the study, animals of group 3 and the control group underwent the same;

As a part of the toxicity research, the influence of local-irritating drugs was also evaluated, for which the soft tissue at the site of injection was selected and histological examination was performed.

Example 28: Investigation of Immunotoxicity of the BCD-121 Anti-IL-17A/Anti-IL-17F/Anti-TNFα Binding Molecule An immunotoxicity assay of repeated subcutaneous administration for 1 month followed by a one-month recovery period was carried out on Javanese macaques. Three dose levels were used in the experiment. The schematic of the experimental groups is shown in Table 8 below.

TABLE 8

| Group Number | Number of animals | Product | Route of administration | Dose |
|---|---|---|---|---|
| 1 | 3 (♂) 3 (♀) | BCD-121 | subcutaneous | Minimal |
| 2 | 3 (♂) 3 (♀) | BCD-121 | | Medium |
| 3 | 3 (♂) 3 (♀) | BCD-121 | | Maximal |
| 4 | 3 (♂) 3 (♀) | Placebo | | — |

In the course of the study, the following parameters were evaluated:

Subpopulation composition of lymphocytes, which was assessed before administration and then at weeks 2, 4 and 6 of the experiment;

Immunoglobulin classes ratio, which was evaluated before administration and at weeks 2, 4 and 6 of the experiment;

Effect on phagocytosis was assessed before administration and then at weeks 2, 4 and 6 of the experiment.

Example 29: Evaluation of Immunogenicity at Repeated Subcutaneous Administration of the BCD-121 Anti-IL-17A/Anti-IL-17F/Anti-TNFα Binding Molecule An immunotoxicity assay of repeated subcutaneous administration for 1 month followed by a one-month recovery period was carried out on Javanese macaques. Three dose levels were used in the experiment. The schematic of the experimental groups is shown in Table 9 below.

TABLE 9

| Group Number | Number of animals | Product | Route of administration | Dose |
|---|---|---|---|---|
| 1 | 3 (♂) 3 (♀) | BCD-121 | subcutaneous | Minimal |
| 2 | 3 (♂) 3 (♀) | BCD-121 | | Medium |
| 3 | 3 (♂) 3 (♀) | BCD-121 | | Maximal |

The immunogenicity assay is performed on the level of antibody binding, for which blood serum is selected and isolated before administration and then at weeks 3, 5, and 7 of the experiment.

Example 30: Pharmacokinetics Assay During Repeated Subcutaneous Administration of the BCD-121 Anti-IL-17A/Anti-IL-17F/Anti-TNFα Binding Molecule A pharmacokinetics assay of repeated subcutaneous administration for one month followed by a one-month recovery period was performed on Javanese macaques. Three dose levels were used. The schematic of the experimental groups is shown in Table 10 below.

TABLE 10

| Group Number | Number of animals | Product | Route of administration | Dose |
|---|---|---|---|---|
| 1 | 3 (♂) 3 (♀) | BCD-121 | subcutaneous | Minimal |
| 2 | 3 (♂) 3 (♀) | BCD-121 | | Medium |
| 3 | 3 (♂) 3 (♀) | BCD-121 | | Maximal |

To estimate the product level, blood sampling was performed on days 0, 1, 2, 8, 9, 15, 16, 22, 23, 29, 36, and 43 of the experiment.

TABLE 11

| SEQ ID NO Chart ||
|---|---|
| SEQ ID NO: | Description |
| 1 | VHH17 CDR1 amino acid sequence |
| 2 | VHH17 CDR2 amino acid sequence |
| 3 | VHH17 CDR3 amino acid sequence |
| 4 | VHH17 amino acid sequence |
| 5 | anti-TNFα HC amino acid sequence |
| 6 | anti-TNFα LC amino acid sequence |
| 7 | VHH17 + anti-TNFα LC amino acid sequence |
| 8 | anti-TNFα VH amino acid sequence |
| 9 | anti-TNFα VL amino acid sequence |
| 10 | anti-TNFα HC-CDR1 amino acid sequence |
| 11 | anti-TNFα HC-CDR2 amino acid sequence |
| 12 | anti-TNFα HC-CDR3 amino acid sequence |
| 13 | anti-TNFα LC-CDR1 amino acid sequence |
| 14 | anti-TNFα LC-CDR2 amino acid sequence |
| 15 | anti-TNFα LC-CDR3 amino acid sequence |
| 16 | peptide linker |
| 17 | parent VHH amino acid sequence |
| 18 | parent anti-TNFα VH amino acid sequence |
| 19 | VKY92F amino acid sequence |
| 20 | VKY94F amino acid sequence |
| 21 | VKS50A amino acid sequence |

TABLE 11-continued

SEQ ID NO Chart

| SEQ ID NO: | Description |
|---|---|
| 22 | VKS50D amino acid sequence |
| 23 | VKS50G amino acid sequence |
| 24 | VKN33D amino acid sequence |
| 25 | VKN33A amino acid sequence |
| 26 | VHG33A amino acid sequence |
| 27 | VHG33S amino acid sequence |

TABLE 11-continued

SEQ ID NO Chart

| SEQ ID NO: | Description |
|---|---|
| 28 | VHN35A amino acid sequence |
| 29 | VHN35H amino acid sequence |
| 30 | VHN35S amino acid sequence |
| 31 | VHN52T amino acid sequence |
| 32 | VHN52Q amino acid sequence |

The invention claimed is:

1. A tri-specific binding molecule comprising a first binding domain that binds to human IL-17A and human IL-17-F and a second binding domain that binds to human TNFα, wherein said first binding domain comprises H-CDR1, H-CDR2, H-CDR3 sequences:
   a) wherein H-CDR1 comprises an amino acid sequence corresponding to SEQ ID NO: 1, H-CDR2 comprises an amino acid sequence corresponding to SEQ ID NO: 2 and H-CDR3 comprises an amino acid sequence corresponding to SEQ ID NO: 3; or
   b) a variant of a), comprising one amino acid substitution selected from the group consisting of:
   the amino acid at the $6^{th}$ position of SEQ ID NO: 1 is S, N, K, R, E, W, M, Q, D, F, V L or A;
   the amino acid at the $7^{th}$ position of SEQ ID NO: 1 is P or S;
   the amino acid at the $8^{th}$ position of SEQ ID NO: 1 is M or I;
   the amino acid at the $9^{th}$ position of SEQ ID NO: 1 is G, L, A, I, S, R, V, N, Q or M;
   the amino acid at the $1^{st}$ position of SEQ ID NO: 2 is A, G or L;
   the amino acid at the $4^{th}$ position of SEQ ID NO: 2 is P or A;
   the amino acid at the $7^{th}$ position of SEQ ID NO: 2 is G, S, R, P, D, I, T, E, K, A or L;
   the amino acid at the $1^{st}$ position of SEQ ID NO: 3 is V, S, T, A, K, D or G;
   the amino acid at the 2nd position of SEQ ID NO: 3 is R or K;
   the amino acid at the $3^{rd}$ position of SEQ ID NO: 3 is R, Y, H, W, K, D or G;
   the amino acid at the $4^{th}$ position of SEQ ID NO: 3 is R, A, L, M, S, H or V;

the amino acid at the 6$^{th}$ position of SEQ ID NO: 3 is D, E, G, A, R, V, K or Q;

the amino acid at the 7$^{th}$ position of SEQ ID NO: 3 is G, N or S;

the amino acid at the 8$^{th}$ position of SEQ ID NO: 3 is T, G, P, V, R, S, N or K;

the amino acid at the 9$^{th}$ position of SEQ ID NO: 3 is S, V, M, T, L, T, A, H, G, I or C;

the amino acid at the 10$^{th}$ position of SEQ ID NO: 3 is Y, W or S;

the amino acid at the 11$^{th}$ position of SEQ ID NO: 3 is Y, R, L, W, K, A, G, Q, I or V; and the amino acid at the 12$^{th}$ position of SEQ ID NO: 3 is T, A, L or S;

said second binding domain comprises a heavy chain comprising H-CDR1, H-CDR2, H-CDR3 sequences, wherein H-CDR1 comprises an amino acid sequence corresponding to SEQ ID NO: 10, H-CDR2 comprises an amino acid sequence corresponding to SEQ ID NO: 11 and H-CDR3 comprises an amino acid sequence corresponding to of SEQ ID NO: 12; and a light chain comprising L-CDR1, L-CDR2, L-CDR3 sequences, wherein L-CDR1 comprises an amino acid sequence corresponding to SEQ ID NO: 13, L-CDR2 comprises an amino acid sequence corresponding to SEQ ID NO: 14 and L-CDR3 comprises an amino acid sequence corresponding to SEQ ID NO: 15.

2. The binding molecule according to claim 1, wherein said binding molecule is an antibody or an antigen-binding fragment thereof.

3. The binding molecule according to claim 1, wherein said first binding domain competes for binding with or binds to the same epitope as a binding domain comprising the amino acid sequence of SEQ ID NO: 4.

4. The binding molecule according to claim 1, wherein said first binding domain is at least 90% identical to SEQ ID NO: 4.

5. The binding molecule according to claim 1, wherein said first binding domain comprises the amino acid sequence of SEQ ID NO: 4.

6. The binding molecule according to claim 1, wherein said first binding domain is humanized.

7. The binding molecule according to claim 1, wherein said second binding domain competes for binding with or binds to the same epitope as a binding domain comprising one of:
a) heavy chain variable domain comprising the amino acid sequence of SEQ ID NO: 8 and a light chain variable domain comprising the amino acid sequence of SEQ ID NO: 9; and
b) heavy chain comprising the amino acid sequence of SEQ ID NO: 5 and a light chain comprising the amino acid sequence of SEQ ID NO: 6.

8. The binding molecule according to claim 1, wherein said second binding domain comprises at least one of: a heavy chain variable domain at least 90% identical to SEQ ID NO: 8; and a variable domain at least 90% identical to SEQ ID NO: 9.

9. The binding molecule according to claim 1, wherein said second binding domain comprises at least one of: a heavy chain variable domain comprising the amino acid sequence of SEQ ID NO: 8; and a light chain variable domain comprising the amino acid sequence of SEQ ID NO: 9.

10. The binding molecule according to claim 1, wherein said second binding domain comprises a heavy chain variable domain consisting of the amino acid sequence of SEQ ID NO: 8 and a light chain variable domain consisting of the amino acid sequence of SEQ ID NO: 9.

11. The binding molecule according to claim 1, wherein the second binding domain is one of: a chimeric antibody; a humanized antibody; a human antibody; a single chain antibody; Fv; Fab; F(ab')2; Fd; single chain Fv molecule (scFv); diabody; and single domain antibody (dAb).

12. The binding molecule according to claim 1, wherein said second binding domain comprises at least one of: a heavy chain at least 90% identical to SEQ ID NO: 5; and a light chain at least 90% identical to SEQ ID NO: 6.

13. The binding molecule according to claim 1, wherein said second binding domain comprises a heavy chain comprising at least one of: the amino acid sequence of SEQ ID NO: 5; and a light chain comprising the amino acid sequence of SEQ ID NO: 6.

14. The binding molecule according to claim 1, wherein said second binding domain comprises a heavy chain consisting of the amino acid sequence of SEQ ID NO: 5 and a light chain consisting of the amino acid sequence of SEQ ID NO: 6.

15. A tri-specific binding molecule comprising a first binding domain that binds to human IL-17A and human IL-17F and a second binding domain that binds to human TNFα, wherein said first binding domain comprises the amino acid sequence of SEQ ID NO: 4 and said second binding domain comprises a heavy chain comprising the amino acid sequence of SEQ ID NO: 5 and a light chain comprising the amino acid sequence of SEQ ID NO: 6.

16. A tri-specific binding molecule that binds to human IL-17A, human IL-17F, and human TNFα, wherein said binding molecule comprises amino acid sequences corresponding to SEQ ID NOs: 5 and 7.

17. The binding molecule according to claim 1, wherein said first binding domain and said second binding domain are joined by a peptide linker of greater than five amino acids.

18. The binding molecule according to claim 17, wherein the amino acid residues of the peptide linker are selected from G, A, S, P, E, T, D, and K.

19. The binding molecule according to claim 17, wherein the peptide linker comprises the amino acid sequence of SEQ ID NO: 16.

20. The binding molecule according to claim 1, wherein said binding molecule is an antibody of isotype IgG or an antigen-binding fragment thereof.

21. The binding molecule according to claim 20, wherein said antibody is of isotype subtype IgG1.

22. A pharmaceutical composition comprising the binding molecule according to claim 1 and a pharmaceutically acceptable excipient.

23. The tri-specific binding molecule according to claim 1, wherein H-CDR1 comprises an amino acid sequence corresponding to SEQ ID NO: 1, H-CDR2 comprises an amino acid sequence corresponding to SEQ ID NO: 2 and H-CDR3 comprises an amino acid sequence corresponding to SEQ ID NO: 3.

* * * * *

SEQUENCE LISTING

<160> NUMBER OF SEQ ID NOS: 32

<210> SEQ ID NO 1
<211> LENGTH: 9
<212> TYPE: PRT
<213> ORGANISM: Artificial Sequence
<220> FEATURE:
<223> OTHER INFORMATION: VHH17 CDR1

<400> SEQUENCE: 1

Gly Thr Phe Ala Thr Ser Pro Met Gly
1               5

<210> SEQ ID NO 2
<211> LENGTH: 17
<212> TYPE: PRT
<213> ORGANISM: Artificial Sequence
<220> FEATURE:
<223> OTHER INFORMATION: VHH17 CDR2

<400> SEQUENCE: 2

Ala Ile Ser Pro Ser Gly Gly Asp Arg Ile Tyr Ala Asp Ser Val Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: VHH17 CDR3

<400> SEQUENCE: 3

Val Arg Arg Arg Phe Asp Gly Thr Ser Tyr Tyr Thr Gly Asp Tyr Asp
1               5                   10                  15

Ser

<210> SEQ ID NO 4
<211> LENGTH: 125
<212> TYPE: PRT
<213> ORGANISM: Artificial Sequence
<220> FEATURE:
<223> OTHER INFORMATION: VHH17

<400> SEQUENCE: 4

Glu Val Gln Leu Val Gln Ser Gly Gly Gly Leu Val Gln Ala Gly Gly
1               5                   10                  15

Ser Leu Arg Leu Ser Cys Ala Ala Ser Gly Gly Thr Phe Ala Thr Ser
            20                  25                  30

Pro Met Gly Trp Leu Arg Gln Ala Pro Gly Lys Gly Thr Glu Phe Val
        35                  40                  45

```
Ala Ala Ile Ser Pro Ser Gly Gly Asp Arg Ile Tyr Ala Asp Ser Val
     50              55                  60

Lys Gly Arg Phe Thr Ile Ser Arg Asp Asn Ala Gly Asn Phe Ile Tyr
 65                  70                  75                  80

Leu Gln Met Asn Ser Leu Lys Pro Glu Asp Thr Ala Val Tyr Tyr Cys
                 85                  90                  95

Ala Val Arg Arg Arg Phe Asp Gly Thr Ser Tyr Tyr Thr Gly Asp Tyr
            100                 105                 110

Asp Ser Trp Gly Gln Gly Thr Leu Val Thr Val Ser Ser
            115                 120                 125
```

<210> SEQ ID NO 5
<211> LENGTH: 448
<212> TYPE: PRT
<213> ORGANISM: Artificial Sequence
<220> FEATURE:
<223> OTHER INFORMATION: anti-TNFa HC

<400> SEQUENCE: 5

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Val Phe Thr Asp Tyr
             20                  25                  30

Gly Met Ser Trp Val Arg Gln Ala Pro Gly Lys Gly Leu Glu Trp Met
         35                  40                  45

Gly Trp Ile Asn Thr Tyr Ile Gly Glu Pro Ile Tyr Ala Asp Ser Val
     50                  55                  60

Lys Gly Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 6
<211> LENGTH: 214
<212> TYPE: PRT
<213> ORGANISM: Artificial Sequence
<220> FEATURE:
<223> OTHER INFORMATION: anti-TNFa LC

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
                20                  25                  30

Val Ala Trp Tyr Gln Gln Lys Pro Gly Lys Ala Pro Lys Ala Leu Ile
            35                  40                  45

Tyr Ser Ala Ser Phe Leu Tyr Ser Gly Val Pro Tyr Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Phe Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 7
<211> LENGTH: 352
<212> TYPE: PRT
<213> ORGANISM: Artificial Sequence
<220> FEATURE:
<223> OTHER INFORMATION: VHH17 + anti-TNFa LC

<400> SEQUENCE: 7

Glu Val Gln Leu Val Gln Ser Gly Gly Gly Leu Val Gln Ala Gly Gly
1               5                   10                  15

Ser Leu Arg Leu Ser Cys Ala Ala Ser Gly Gly Thr Phe Ala Thr Ser
            20                  25                  30

Pro Met Gly Trp Leu Arg Gln Ala Pro Gly Lys Gly Thr Glu Phe Val
        35                  40                  45

Ala Ala Ile Ser Pro Ser Gly Gly Asp Arg Ile Tyr Ala Asp Ser Val
    50                  55                  60

Lys Gly Arg Phe Thr Ile Ser Arg Asp Asn Ala Gly Asn Phe Ile Tyr
65                  70                  75                  80

Leu Gln Met Asn Ser Leu Lys Pro Glu Asp Thr Ala Val Tyr Tyr Cys
                85                  90                  95

Ala Val Arg Arg Arg Phe Asp Gly Thr Ser Tyr Tyr Thr Gly Asp Tyr
            100                 105                 110

Asp Ser Trp Gly Gln Gly Thr Leu Val Thr Val Ser Ser Gly Gly Gly
        115                 120                 125

Ser Gly Gly Gly Ser Glu Gly Ala Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Lys Ala Ser Gln Asn Val Gly Thr Asn Val Ala Trp Tyr Gln Gln
                165                 170                 175

Lys Pro Gly Lys Ala Pro Lys Ala Leu Ile Tyr Ser Ala Ser Phe Leu
            180                 185                 190

Tyr Ser Gly Val Pro Tyr Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr Asn Ile Phe Pro Leu Thr Phe Gly Gln Gly Thr
225                 230                 235                 240

Lys Val Glu Ile Lys Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
    290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
            340                 345                 350

<210> SEQ ID NO 8
<211> LENGTH: 118
<212> TYPE: PRT
<213> ORGANISM: Artificial Sequence
<220> FEATURE:
<223> OTHER INFORMATION: anti-TNFa VH

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Ser Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115
```

<210> SEQ ID NO 9
<211> LENGTH: 107
<212> TYPE: PRT
<213> ORGANISM: Artificial Sequence
<220> FEATURE:
<223> OTHER INFORMATION: anti-TNFa VL

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Phe Pro Leu
                85                  90                  95

Thr Phe Gly Gln Gly Thr Lys Val Glu Ile Lys
            100                 105
```

<210> SEQ ID NO 10
<211> LENGTH: 5
<212> TYPE: PRT
<213> ORGANISM: Artificial Sequence
<220> FEATURE:
<223> OTHER INFORMATION: anti-TNFa HC-CDR1

<400> SEQUENCE: 10

```
Asp Tyr Gly Met Ser
1               5
```

```
<210> SEQ ID NO 11
<211> LENGTH: 17
<212> TYPE: PRT
<213> ORGANISM: Artificial Sequence
<220> FEATURE:
<223> OTHER INFORMATION: anti-TNFa HC-CDR2

<400> SEQUENCE: 11

Trp Ile Asn Thr Tyr Ile Gly Glu Pro Ile Tyr Ala Asp Ser Val Lys
1               5                   10                  15
Gly

<210> SEQ ID NO 12
<211> LENGTH: 9
<212> TYPE: PRT
<213> ORGANISM: Artificial Sequence
<220> FEATURE:
<223> OTHER INFORMATION: anti-TNFa HC-CDR3

<400> SEQUENCE: 12

Gly Tyr Arg Ser Tyr Ala Met Asp Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: anti-TNFa LC-CDR1

<400> SEQUENCE: 13

Lys Ala Ser Gln Asn Val Gly Thr Asn Val Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: anti-TNFa LC-CDR2

<400> SEQUENCE: 14

Ser Ala Ser Phe Leu Tyr Ser
1               5

<210> SEQ ID NO 15
<211> LENGTH: 9
<212> TYPE: PRT
<213> ORGANISM: Artificial Sequence
<220> FEATURE:
<223> OTHER INFORMATION: anti-TNFa LC-CDR3

<400> SEQUENCE: 15

Gln Gln Tyr Asn Ile Phe Pro Leu Thr
1               5

<210> SEQ ID NO 16
<211> LENGTH: 13
<212> TYPE: PRT
<213> ORGANISM: Artificial Sequence
<220> FEATURE:
<223> OTHER INFORMATION: peptide linker

<400> SEQUENCE: 16

Gly Gly Gly Ser Gly Gly Gly Ser Glu Gly Ala Gly Ser
1               5                   10
```

```
<210> SEQ ID NO 17
<211> LENGTH: 125
<212> TYPE: PRT
<213> ORGANISM: Artificial Sequence
<220> FEATURE:
<223> OTHER INFORMATION: parent VHH

<400> SEQUENCE: 17

Gln Val Gln Leu Gln Gln Ser Gly Gly Ser Val Gln Ala Gly Gly
1               5                   10                  15

Ser Leu Arg Leu Ser Cys Ala Ala Ser Gly Gly Thr Phe Ala Thr Ser
            20                  25                  30

Pro Met Gly Trp Leu Arg Gln Ala Pro Gly Lys Glu Arg Glu Phe Val
        35                  40                  45

Ala Ala Ile Ser Pro Ser Gly Gly Asp Arg Ile Tyr Asp Asp Ser Val
    50                  55                  60

Lys Gly Arg Phe Thr Ile Ser Arg Asp Asn Ala Gly Tyr Phe Ile Tyr
65                  70                  75                  80

Leu Gln Met Asn Ser Leu Lys Pro Glu Asp Thr Ala Arg Tyr Tyr Cys
                85                  90                  95

Ala Val Arg Arg Phe Asp Gly Thr Ser Tyr Tyr Thr Gly Asp Tyr
            100                 105                 110

Asp Ser Trp Gly Gln Gly Thr Leu Val Thr Val Ser Ser
        115                 120                 125

<210> SEQ ID NO 18
<211> LENGTH: 118
<212> TYPE: PRT
<213> ORGANISM: Artificial Sequence
<220> FEATURE:
<223> OTHER INFORMATION: parent anti-TNFa VH

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: VKY92F

<400> SEQUENCE: 19

Asp Ile Gln Met Thr Gln Ser Pro Ser Ser Leu Ser Ala Ser Val Gly
```

```
                1               5                  10                 15
Asp Arg Val Thr Ile Thr Cys Lys Ala Ser Gln Asn Val Gly Thr Asn
                    20                  25                 30

Val Ala Trp Tyr Gln Gln Lys Pro Gly Lys Ala Pro Lys Ala Leu Ile
            35                  40                 45

Tyr Ser Ala Ser Phe Leu Tyr Ser Gly Val Pro Tyr Arg Phe Ser Gly
        50                  55                 60

Ser Gly Ser Gly Thr Asp Phe Thr Leu Thr Ile Ser Ser Leu Gln Pro
65                  70                  75                 80

Glu Asp Phe Ala Thr Tyr Tyr Cys Gln Gln Phe Asn Ile Tyr Pro Leu
                85                  90                 95

Thr Phe Gly Gln Gly Thr Lys Val Glu Ile Lys
                100                 105

<210> SEQ ID NO 20
<211> LENGTH: 107
<212> TYPE: PRT
<213> ORGANISM: Artificial Sequence
<220> FEATURE:
<223> OTHER INFORMATION: VKY94F

<400> SEQUENCE: 20

Asp Ile Gln Met Thr Gln Ser Pro Ser Ser Leu Ser Ala Ser Val Gly
1               5                  10                 15

Asp Arg Val Thr Ile Thr Cys Lys Ala Ser Gln Asn Val Gly Thr Asn
                    20                  25                 30

Val Ala Trp Tyr Gln Gln Lys Pro Gly Lys Ala Pro Lys Ala Leu Ile
            35                  40                 45

Tyr Ser Ala Ser Phe Leu Tyr Ser Gly Val Pro Tyr Arg Phe Ser Gly
        50                  55                 60

Ser Gly Ser Gly Thr Asp Phe Thr Leu Thr Ile Ser Ser Leu Gln Pro
65                  70                  75                 80

Glu Asp Phe Ala Thr Tyr Tyr Cys Gln Gln Tyr Asn Ile Phe Pro Leu
                85                  90                 95

Thr Phe Gly Gln Gly Thr Lys Val Glu Ile Lys
                100                 105

<210> SEQ ID NO 21
<211> LENGTH: 107
<212> TYPE: PRT
<213> ORGANISM: Artificial Sequence
<220> FEATURE:
<223> OTHER INFORMATION: VKS50A

<400> SEQUENCE: 21

Asp Ile Gln Met Thr Gln Ser Pro Ser Ser Leu Ser Ala Ser Val Gly
1               5                  10                 15

Asp Arg Val Thr Ile Thr Cys Lys Ala Ser Gln Asn Val Gly Thr Asn
                    20                  25                 30

Val Ala Trp Tyr Gln Gln Lys Pro Gly Lys Ala Pro Lys Ala Leu Ile
            35                  40                 45

Tyr Ala Ala Ser Phe Leu Tyr Ser Gly Val Pro Tyr Arg Phe Ser Gly
        50                  55                 60

Ser Gly Ser Gly Thr Asp Phe Thr Leu Thr Ile Ser Ser Leu Gln Pro
65                  70                  75                 80

Glu Asp Phe Ala Thr Tyr Tyr Cys Gln Gln Tyr Asn Ile Tyr Pro Leu
                85                  90                 95
```

```
Thr Phe Gly Gln Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: VKS50D

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Asp Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: VKS50G

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Gly Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: VKN33D

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asp
```

```
            20                  25                  30
Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 25
<211> LENGTH: 107
<212> TYPE: PRT
<213> ORGANISM: Artificial Sequence
<220> FEATURE:
<223> OTHER INFORMATION: VKN33A

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 26
<211> LENGTH: 118
<212> TYPE: PRT
<213> ORGANISM: Artificial Sequence
<220> FEATURE:
<223> OTHER INFORMATION: VHG33A

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Ala Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110
```

Leu Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: VHG33S

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Ser Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 28
<211> LENGTH: 118
<212> TYPE: PRT
<213> ORGANISM: Artificial Sequence
<220> FEATURE:
<223> OTHER INFORMATION: VHN35A

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Ala Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 29
<211> LENGTH: 118
<212> TYPE: PRT
<213> ORGANISM: Artificial Sequence
<220> FEATURE:
<223> OTHER INFORMATION: VHN35H

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met His Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: VHN52T

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Thr Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: VHN52Q

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

```
Gly Trp Ile Gln Thr Tyr Ile Gly Glu Pro Ile Tyr Ala Asp Ser Val
    50              55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
                100                 105                 110

Leu Val Thr Val Ser Ser
        115

<210> SEQ ID NO 32
<211> LENGTH: 163
<212> TYPE: PRT
<213> ORGANISM: Artificial Sequence
<220> FEATURE:
<223> OTHER INFORMATION: IL-17A-His6 FLAG

<400> SEQUENCE: 32

Asp Ile Val Lys Ala Gly Ile Thr Ile Pro Arg Asn Pro Gly Cys Pro
1               5                   10                  15

Asn Ser Glu Asp Lys Asn Phe Pro Arg Thr Val Met Val Asn Leu Asn
                20                  25                  30

Ile His Asn Arg Asn Thr Asn Thr Asn Pro Lys Arg Ser Ser Asp Tyr
                35                  40                  45

Tyr Asn Arg Ser Thr Ser Pro Trp Asn Leu His Arg Asn Glu Asp Pro
    50                  55                  60

Glu Arg Tyr Pro Ser Val Ile Trp Glu Ala Lys Cys Arg His Leu Gly
65                  70                  75                  80

Cys Ile Asn Ala Asp Gly Asn Val Asp Tyr His Met Asn Ser Val Pro
                85                  90                  95

Ile Gln Gln Glu Ile Leu Val Leu Arg Arg Glu Pro Pro His Cys Pro
                100                 105                 110

Asn Ser Phe Arg Leu Glu Lys Ile Leu Val Ser Val Gly Cys Thr Cys
            115                 120                 125

Val Thr Pro Ile Val His His Val Ala Ala Ala Gly Gly Gly Glu Ser
        130                 135                 140

His His His His His His Gly Asp Ile Leu Asp Tyr Lys Asp Asp Asp
145                 150                 155                 160

Asp Lys Val
```